(12) United States Patent
Simon et al.

(10) Patent No.: US 8,030,442 B2
(45) Date of Patent: *Oct. 4, 2011

(54) TREATMENT OF INJURY TO THE BRAIN BY INHIBITION OF ACID SENSING ION CHANNELS

(75) Inventors: Roger P. Simon, Portland, OR (US); Zhi-Gang Xiong, Beaverton, OR (US)

(73) Assignee: Morehouse School of Medicine, Atlanta, GA (US)

( * ) Notice: Subject to any disclaimer, the term of this patent is extended or adjusted under 35 U.S.C. 154(b) by 785 days.

This patent is subject to a terminal disclaimer.

(21) Appl. No.: 11/943,546

(22) Filed: Nov. 20, 2007

(65) Prior Publication Data

US 2008/0279965 A1 Nov. 13, 2008

Related U.S. Application Data

(63) Continuation-in-part of application No. 11/724,859, filed on Mar. 16, 2007, which is a continuation of application No. PCT/US2005/033171, filed on Sep. 16, 2005.

(60) Provisional application No. 60/860,522, filed on Nov. 21, 2006, provisional application No. 60/611,241, filed on Sep. 16, 2004.

(51) Int. Cl.
*A61K 38/00* (2006.01)
*C07K 14/00* (2006.01)

(52) U.S. Cl. .................. 530/300; 424/78.08; 514/2

(58) Field of Classification Search .................. None
See application file for complete search history.

(56) References Cited

U.S. PATENT DOCUMENTS

2007/0232540 A1* 10/2007 Simon et al. .............. 514/12
2008/0279965 A1 11/2008 Simon et al.

FOREIGN PATENT DOCUMENTS

| WO | 01/85931 | 11/2001 |
| WO | 2006/034035 | 3/2006 |

OTHER PUBLICATIONS

International Search Report (PCT/US05/33171)—Aug. 18, 2006.
Aarts, et al., (2004), "Treatment of Ischemic Brain Damage by Perturbing NMDA Receptor-PSD-95 Protein Interations", vol. 298, Science Magazine, pp. 846-850.
Xiong, et al., (2004), "Neuroprotection in Ischemia: Blocking Calcium-Permeable Acid-Sensing Ion Channels", Cell, vol. 118, pp. 687-698.
Bladin, et al., (2000) "Seizures After Stroke—A Prospective Multicenter Study", Arch Neurol. vol. 57, pp. 1617-1622.
Anderson, et al., (2002), "Protection of Focal Cerebral Ischemia by Alkalinazation of Systematic pH", Neurosurgery 51:1258-1266.

* cited by examiner

*Primary Examiner* — Anand Desai
(74) *Attorney, Agent, or Firm* — Ping Wang; Andrews Kurth, LLP

(57) ABSTRACT

Methods and compositions that inhibit acid sensing ion channels are provided for the prevention and treatment of brain injury, including injury caused by stroke or seizure. The methods and compositions of the invention are additionally effective for the reduction of acidosis in the brain.

22 Claims, 39 Drawing Sheets

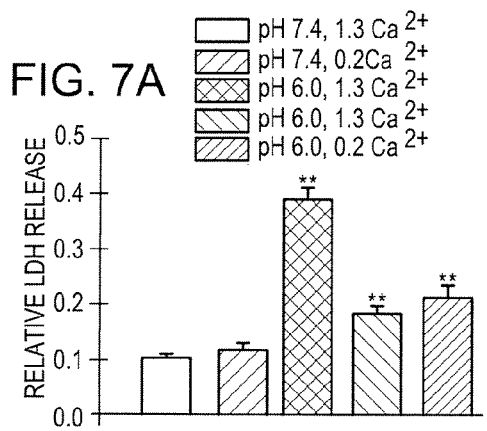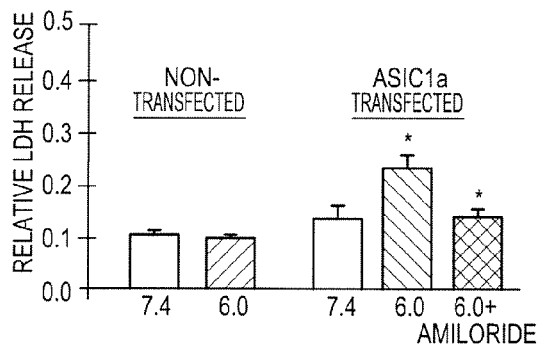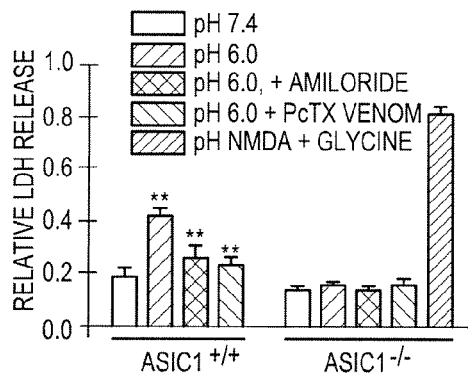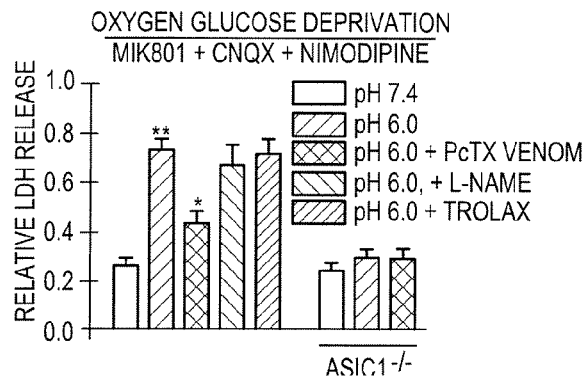

FIG. 11

| | VARIANT | IDENTIFIER | POSITION<br>--------1--------2--------3-------4 |
|---|---|---|---|
| 50 | FULL LENGTH PcTx1 | (SEQ ID: 1): | EDCIPKWKGCVNRHGDCCEGLECWKRRRSFEVCVPKTPKT |
| 70 | N-TERMINAL DEL. | (SEQ ID: 2): | CIPKWKGCVNRHGDCCEGLECWKRRRSFEVCVPKTPKT |
| 72 | C-TERMINAL DEL. | (SEQ ID: 3): | EDCIPKWKGCVNRHGDCCEGLECWKRRRSFEVCVPKT |
| 74 | FULL C-TERMINAL DEL. | (SEQ ID: 4): | EDCIPKWKGCVNRHGDCCEGLECWKRRRSFEVC |
| 76 | N & C-TERMINAL DEL. | (SEQ ID: 5): | CIPKWKGCVNRHGDCCEGLECWKRRRSFEVC |

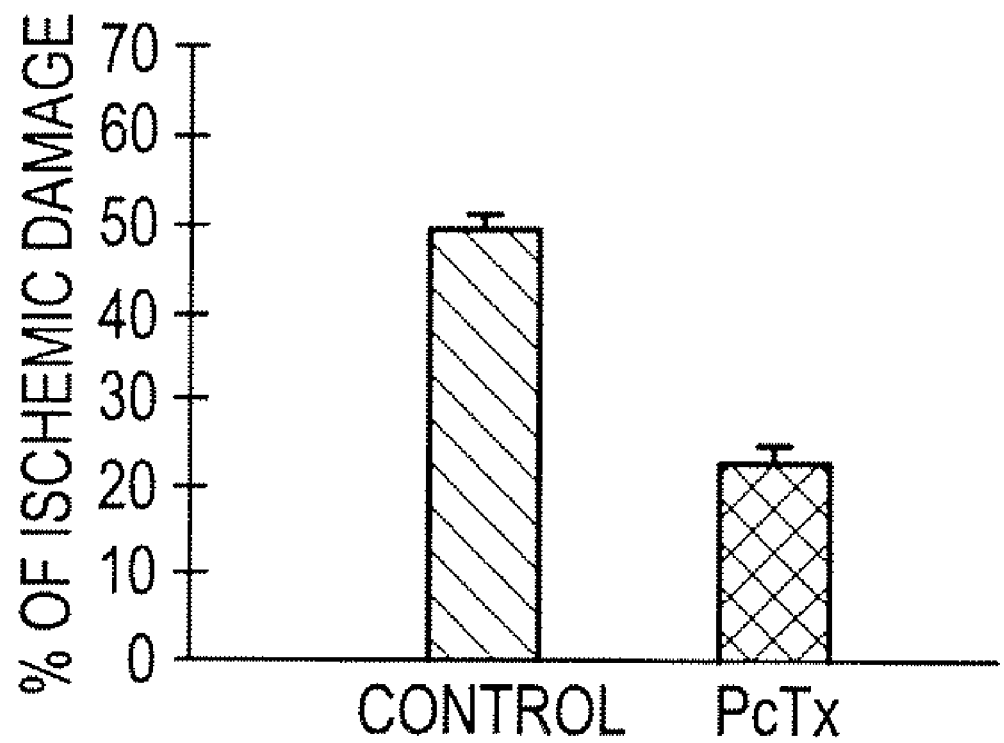

icv 1 h after MCAO 24 h after MCAO

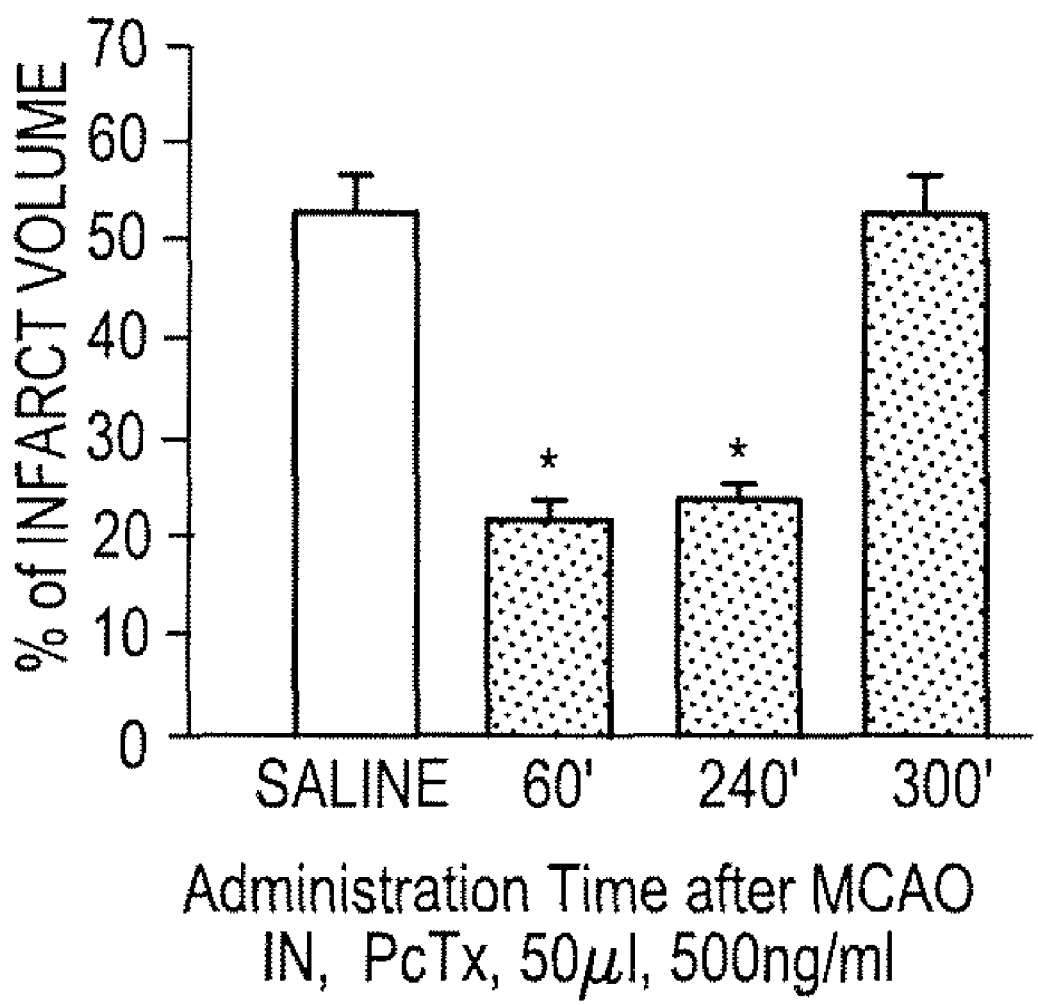

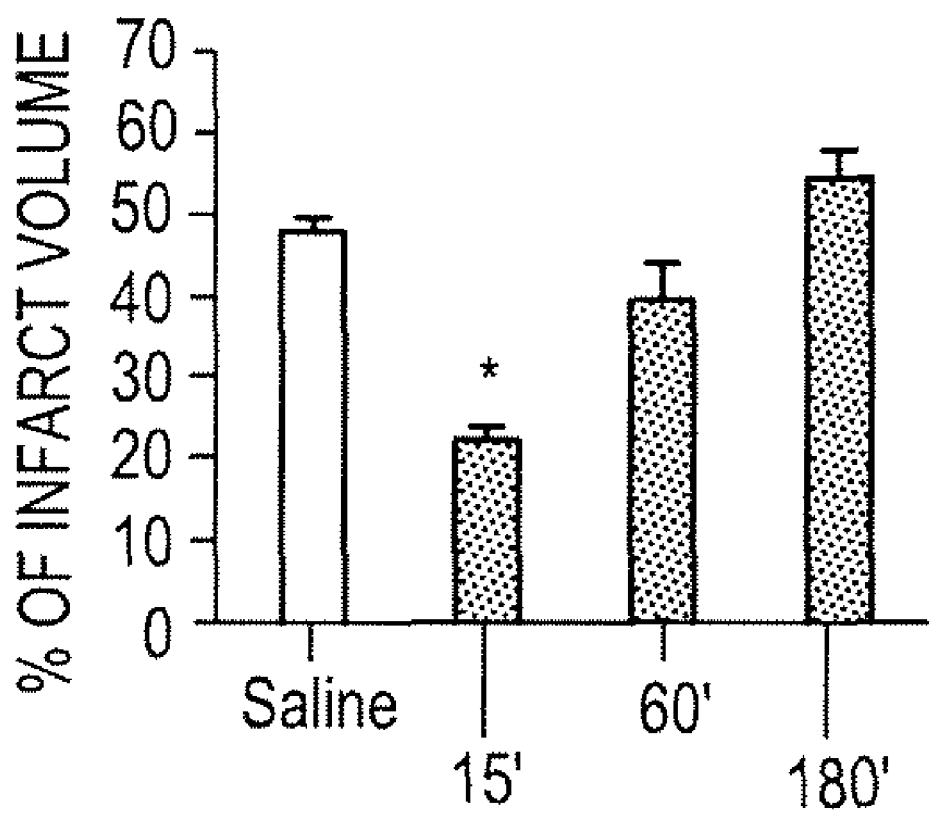

| Time after MCAO | Sham | Vehicle | PcTX | NaHCO3 |
| --- | --- | --- | --- | --- |
| 1 h | 7.26±0.05 | 7.16±0.05 | 7.32±0.04 | 7.26±0.03 |
| 2 h | 7.18±0.11 | 7.63±0.11 | 7.70±0.03 | 7.41±0.48 |
| 3 h | 7.15±0.07 | 6.69±0.16 | 6.78±0.13 | 6.60±0.60 |
| 4 h | 7.16±0.03 | 6.58±0.07 | 6.66±0.09 | 7.25±0.65 |

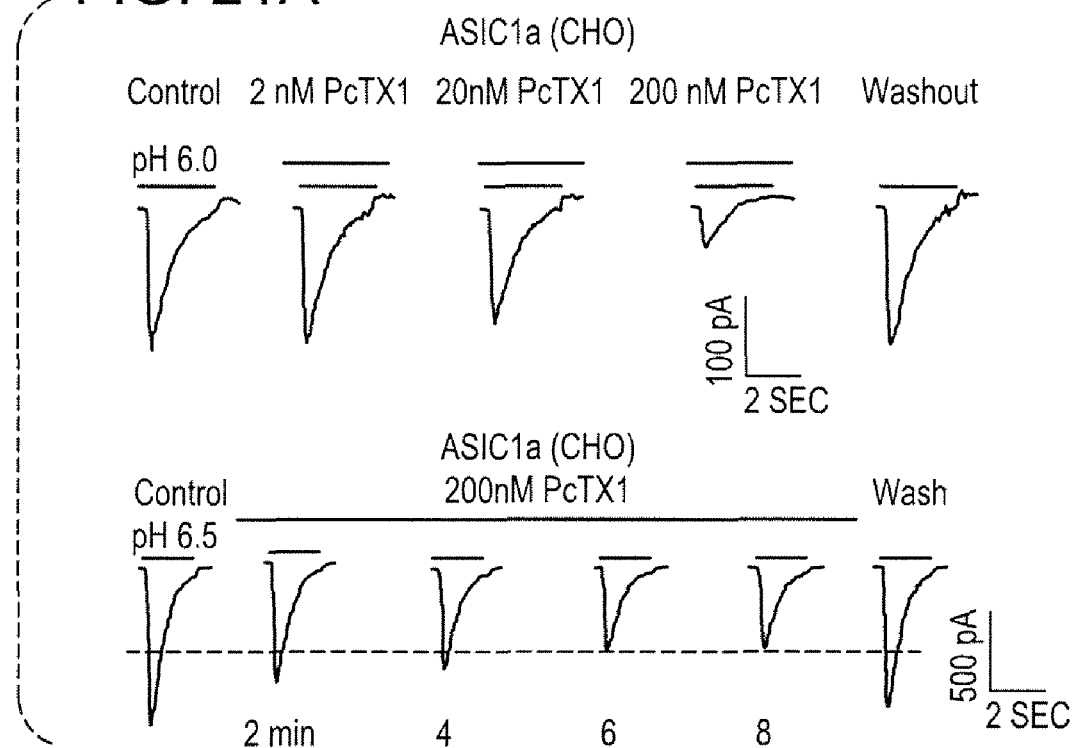

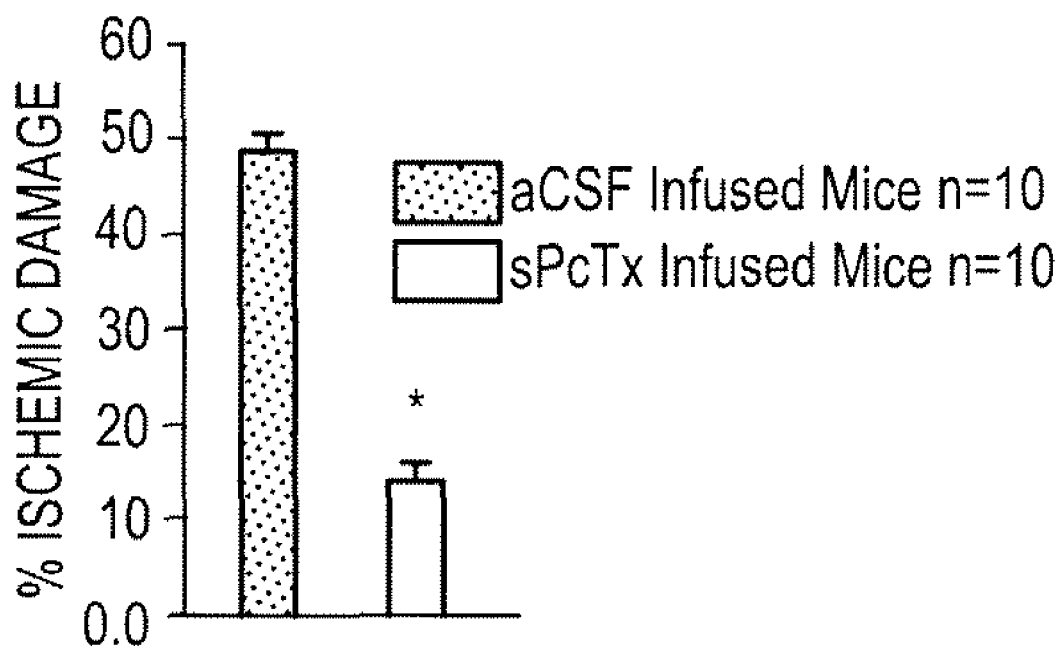

Amiloride inhibits epileptic events in hippocampal slice induced by low $[Mg^{2+}]_0$ Amiloride inhibits epileptic events in hippocampal slice induced by low $[Mg^{2+}]_0$ Amiloride inhibits seizure-like activity in cultured hippocampal neurons (expanded version)

PcTX reduces seizure-induced injury of CA3 neurons in KA injected mice

Dose-dependent protection by synthetic PcTx1

Time window for synthetic PcTX1

FIG. 31A

Protection by IV injection of sPcTX1 aCSF          sPcTX1, iv, 500 nM

GFP alone pH 7.4 pH 6.0

GFP/ASIC1a pH 7.4 pH 6.0

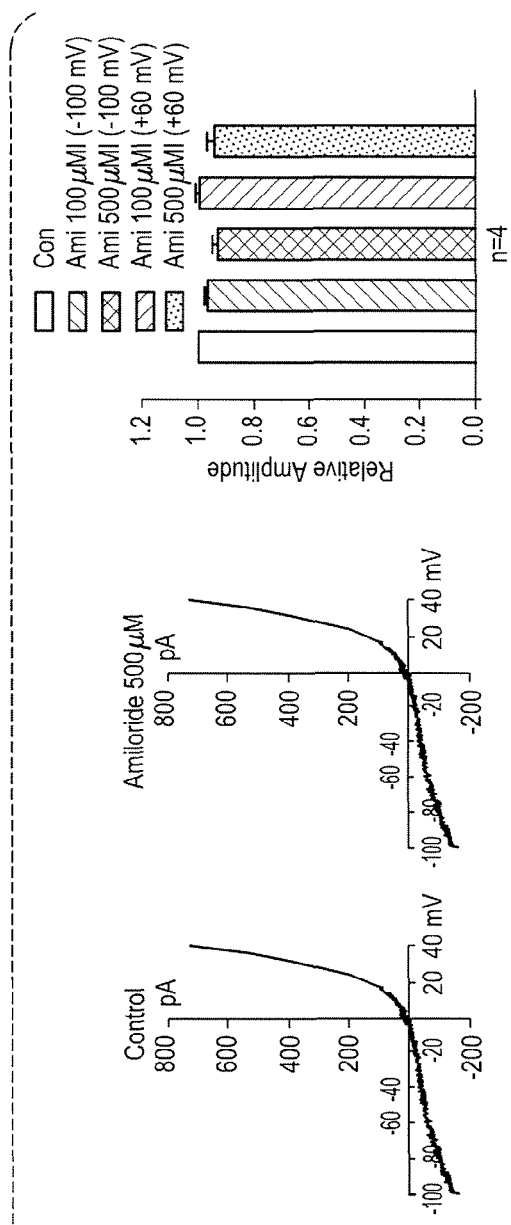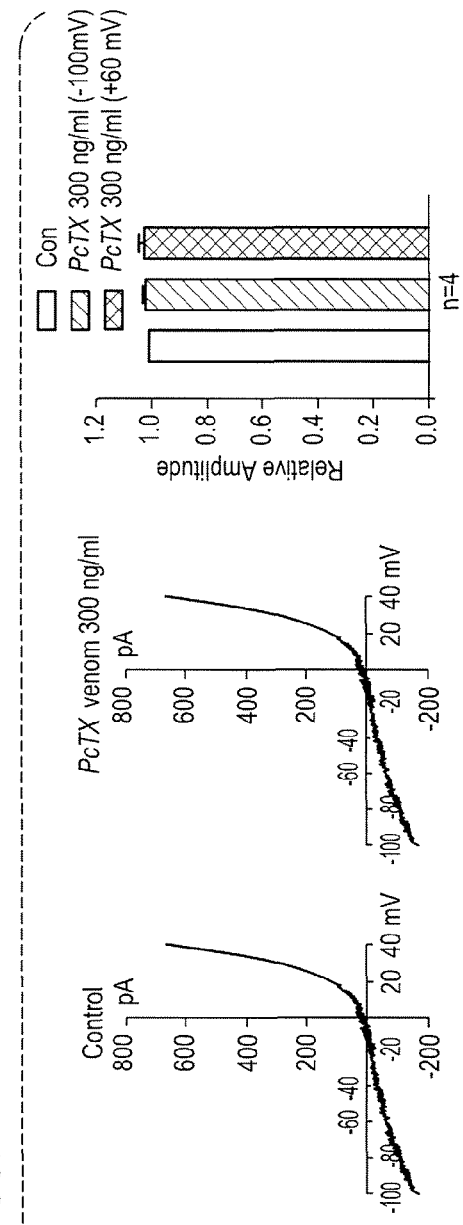
FIG. 36A
FIG. 36B

SEQUENCE LISTING

<160> NUMBER OF SEQ ID NOS: 5

<210> SEQ ID NO 1
<211> LENGTH: 40
<212> TYPE: PRT
<213> ORGANISM: Psalmopoeus cambridgei

<400> SEQUENCE: 1

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
                20                  25                  30

Cys Val Pro Lys Thr Pro Lys Thr
            35                  40

<210> SEQ ID NO 2
<211> LENGTH: 38
<212> TYPE: PRT
<213> ORGANISM: Psalmopoeus cambridgei

<400> SEQUENCE: 2

Cys Ile Pro Lys Trp Lys Gly Cys Val Asn Arg His Gly Asp Cys Cys
1               5                   10                  15

Glu Gly Leu Glu Cys Trp Lys Arg Arg Arg Ser Phe Glu Val Cys Val
                20                  25                  30

Pro Lys Thr Pro Lys Thr
            35

<210> SEQ ID NO 3
<211> LENGTH: 37
<212> TYPE: PRT
<213> ORGANISM: Psalmopoeus cambridgei

<400> SEQUENCE: 3

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
                20                  25                  30

Cys Val Pro Lys Thr
            35

<210> SEQ ID NO 4
<211> LENGTH: 33
<212> TYPE: PRT
<213> ORGANISM: Psalmopoeus cambridgei

<400> SEQUENCE: 4

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
                20                  25                  30

Cys

<210> SEQ ID NO 5
<211> LENGTH: 31
<212> TYPE: PRT
<213> ORGANISM: Psalmopoeus cambridgei

<400> SEQUENCE: 5

Cys Ile Pro Lys Trp Lys Gly Cys Val Asn Arg His Gly Asp Cys Cys
1               5                   10                  15

Glu Gly Leu Glu Cys Trp Lys Arg Arg Arg Ser Phe Glu Val Cys
                20                  25                  30

TREATMENT OF INJURY TO THE BRAIN BY INHIBITION OF ACID SENSING ION CHANNELS

RELATED APPLICATIONS

This patent application is a Continuation-In-Part of U.S. patent application Ser. No. 11/724,859, filed Mar. 16, 2007, which is a continuation application of PCT/US2005/33171, filed Sep. 16, 2005, which claims priority of U.S. Provisional patent application Ser. No. 60/611,241, filed Sep. 16, 2004. This application also claims priority of U.S. Provisional patent application Ser. No. 60/860,522, filed Nov. 21, 2006. The entirety of all of the aforementioned applications is incorporated herein by reference.

U.S. GOVERNMENT RIGHTS

This invention was made with U.S. Government support under grant R21 NS42799 from the National Institutes of Health. The U.S. Government thus may have certain license rights in this invention.

TECHNICAL FIELD

The present invention relates to brain injury in mammalian subjects. More specifically, the invention relates to methods and compositions for preventing or treating neuronal damage in mammals through the inhibition of acid sensing ion channels.

BACKGROUND

Stroke is the third leading cause of death in the United States and the most common cause of adult disability. An ischemic stroke occurs when a cerebral vessel occludes, obstructing blood flow to a portion of the brain. Ischemia leads to excessive activation of excitatory amino acid receptors, accumulation of intracellular calcium, and release of other toxic products that cause cellular injury. The only currently approved medical stroke therapy, tissue plasminogen activator (tPA), is a thrombolytic that targets the thrombus within the blood vessel.

During ischemia, oxygen depletion may force the brain to switch to anaerobic glycolysis. Accumulation of lactic acid as a byproduct of glycolysis and protons produced by ATP hydrolysis may cause pH to fall in the ischemic brain (Rehncrona 1985 and Siesjo et al. 1996). Consequently, tissue pH typically falls to 6.5-6.0 during ischemia under normoglycemic conditions and may fall below 6.0 during severe ischemia or under hyperglycemic conditions (Nedergaard et al. 1991; Rehncrona 1985 and Siesjo et al. 1996). Nearly all in vivo studies indicate that acidosis aggravates ischemic brain injury (Tombaugh and Sapolsky 1993 and Siesjo et al. 1996). However, the mechanisms of this process remain unclear, although a host of possibilities has been suggested (Siesjo et al. 1996; McDonald et al. 1998; Swanson et al. 1995 and Ying et al. 1999).

Intracellular $Ca^{2+}$ overload may be important for neuronal injury associated with neuropathological syndromes, including brain ischemia (Choi 1995 and Choi 1988a). Excessive $Ca^{2+}$ in the cell may activate a cascade of cytotoxic events leading to activation of enzymes that break down proteins, lipids, and nucleic acids. NMDA receptors, which may be the most important excitatory neurotransmitter receptors in the central nervous system (McLennan 1983 and Dingledine et al. 1999), have long been considered the main target responsible for $Ca^{2+}$ overload in the ischemic brain (Simon et al. 1984; Rothman and Olney 1986; Choi 1988b and Meldrum 1995). However, recent clinical efforts to prevent brain injury through the therapeutic use of NMDA receptor antagonists have been disappointing (Lee et al. 1999 and Wahlgren and Ahmed 2004).

Despite many reports of pharmacological compounds showing significant neuroprotection in experimental models of brain injury such as stroke, no major clinical trials of a neuroprotectant has shown improved outcome. There is therefore a need for the development of additional neuroprotectants for the treatment of brain injury.

SUMMARY OF THE EXEMPLARY EMBODIMENTS OF THE INVENTION

The present teachings provide methods and compositions for the prevention and treatment of brain injury. Specifically, the present teachings provide methods and compositions for the prevention and treatment of neuronal injury caused by acidosis of the brain.

The invention achieves these objects and satisfies additional objects and advantages by providing novel and surprisingly effective methods and compositions for treating and preventing neuronal injury through the use of inhibitors of acid sensing ion channels (ASIC).

Acid-sensing ion channels (ASICs) are voltage-independent, proton-activated receptors that belong to the epithelial sodium channel/degenerin family of ion channels and are implicated in perception of pain, ischemic stroke, mechanosensation, learning and memory.

Mammalian subjects amenable for treatment with inhibitors of acid sensing ion channels according to the methods of the invention include, but are not limited to those suffering from or at risk for neuronal injury including those with a history of seizures, including epilepsy; with a history of or at risk for ischemia; stroke; traumatic brain injury; surgery; infection; acidosis; ischemia; activation of one or more acid-sensing ion channels (with or without acidosis/ischemia); at risk for an ischemic event; at risk for stroke including a hemorrhagic stroke, an ischemic stroke, or the result of global ischemia (e.g., cardiac arrest); those with high cholesterol; high blood pressure; heart disease; irregular heart rhythms, such as atrial fibrillation, phlebitis, congestive heart failure; or any other disease or symptom that increases the likelihood of a neuronal injury such as those diseases and conditions that put an individual at risk for a seizure or stroke.

These and other subjects are effectively treated, prophylactically and/or therapeutically, by administering to the subject a neuronal protective effective amount of an ASIC inhibitor. Inhibitors of ASIC family members, as used herein, are substances that reduce (partially, substantially, or completely block) the activity or one or more members of the ASIC family, that is, ASIC1a, ASIC1b, ASIC2a, ASIC2b, ASIC3, and ASIC4, among others. In some examples, the inhibitors may reduce the channel activity of one or more members, such as the ability of the members to flux ions (e.g., sodium, calcium, and/or potassium ions, among others) through cell membranes (into and/or out of cells). The substances may be compounds (small molecules of less than about 10 kDa, peptides, nucleic acids, lipids, etc.), complexes of two or more compounds, and/or mixtures, among others. Furthermore, the substances may inhibit ASIC family members by any suitable mechanism including competitive, noncompetitive, uncompetitive, mixed inhibition, and/or by changing a subject's pH, among others. In some embodiments, an ASIC inhibitor may be selective within the ASIC family of channels. In other embodiments, an ASIC inhibitor may be specific for a particular ASIC family member. An exemplary ASIC inhibitor is psalmotoxin 1 (PcTx1), a toxin from a *Psalmopoeus cambridgei* and variants of PcTx1. Such variants may possess at least 50% sequence identity counted over the full length alignment with the amino acid sequence of a native PcTx1 polypeptide EDCIPKWKGCVNRHGDCCE-GLECWKRRRSFEVCVPKTPKT (SEQ ID NO. 1) using the NCBI Blast 2.0, gapped blastp set to default parameters. Proteins with even greater similarity to the reference sequences will show increasing percentage identities when assessed by this method, such as at least 60%, at least 65%, at least 70%, at least 74%, at least 75%, at least 77%, at least 80%, at least 90% or at least 95% amino acid sequence identity.

Within additional aspects of the invention, combinatorial formulations and methods are provided which employ an effective amount of an ASIC inhibitor compound such as PcTx1 and variants thereof in combination with one or more secondary or adjunctive active agent(s) that is/are combinatorially formulated or coordinately administered with an ASIC inhibitor to yield a neuronal protective response in the subject. Exemplary combinatorial formulations and coordinate treatment methods in this context employ the ASIC inhibitor in combination with one or more additional, neuronal protective or other indicated, secondary or adjunctive therapeutic agents. The secondary or adjunctive therapeutic agents used in combination with, e.g., an ASIC inhibitor in these embodiments may possess direct or indirect neuronal protective activity, alone or in combination with, e.g. PcTx1, or may exhibit other useful adjunctive therapeutic activity in combination with, e.g., PcTx1.

Useful adjunctive therapeutic agents in these combinatorial formulations and coordinate treatment methods include, for example, an antagonist selective for a glutamate receptor, such as an NMDA-receptor inhibitor including, but not limited to, ketamine, dextromethorphan, memantine, amantadine, 2-amino-5-phosphonopentanoate (AP5), dizocilipine, phencyclidine, riluzole, and cis-4-[phosphonomethyl]-2-piperidine carboxylic acid; an alkalinizing agent, such as sodium bicarbonate; nitroglycerin; anticoagulant medications, such as warfarin, dicumarol, anisinidione, and heparin; tissue plasminogen activator; aspirin; and anti-platelet agents including, but not limited to, clopidogrel bisulfate.

The forgoing objects and additional objects, features, aspects and advantages of the instant invention will become apparent from the following detailed description.

BRIEF DESCRIPTION OF THE DRAWINGS

FIG. 7 A-D is a series of graphs (A) illustrating inhibition of acid-induced LDH release by reducing [Ca$^{2+}$]$_e$ (n=11-12, $**p<0.01$ compared with pH 6.0, 1.3 Ca$^{2+}$); (B) acid incubation induced increase of LDH release in ASIC1a-transfected but not nontransfected COS-7 cells (n=8-20); (C) a lack of acid-induced injury and protection by amiloride and PcTX venom in ASIC1$^{-/-}$ neurons (n=8 in each group, p>0.05); and (D) acid-induced increase of LDH release in cultured cortical neurons under oxygen glucose deprivation (n=5).

FIG. 11 shows a comparison of the PcTx1 peptide 50 of FIG. 10 aligned with various exemplary deletion derivatives of the peptide.

FIG. 13 is a graph of the amount of ischemic damage in mice treated intranasally with 50 µL, 500 ng/mL PcTX venom versus control.

FIG. 16 is a chart of the protective effect of intranasal administration of 50 μL, 500 ng/mL PcTX venom administered 1, 4 and 5 hours after middle cerebral artery occlusion.

FIG. 18 is a graph presenting exemplary data from experiments measuring the percentage of brain infarct volume as a function of the time (in minutes) of administration of memantine after mid-cerebral artery occlusion.

FIG. 22 is a graph presenting exemplary data for the amount of ischemic damage produced in vivo (in mice) after experimental stroke and intracerebroventricular administration of synthetic PcTx1 peptide or artificial cerebrospinal fluid.

FIG. 31 shows (A) photographs of and (B) a graph of differences in infarct volume in cortical tissue of C57B16 mice treated with intravenous injection of either aCSF or synthetic PcTX1 one hour prior to 60 minutes of middle cerebral artery occlusion.

FIGS. 36 A and B are (A) representative current-voltage relationship (I-V curve) and summary bar graph demonstrating the lack of blockade of TRPM7 conductance by amiloride (100 and 500 μM, n=4 for each treatment); and (B) representative current-voltage relationship (I-V curve) and summary bar graph demonstrating the lack of blockade of TRPM7 conductance by PcTX venom (300 ng/ml).

DETAILED DESCRIPTION OF EXEMPLARY EMBODIMENTS OF THE INVENTION

Figure 1A:
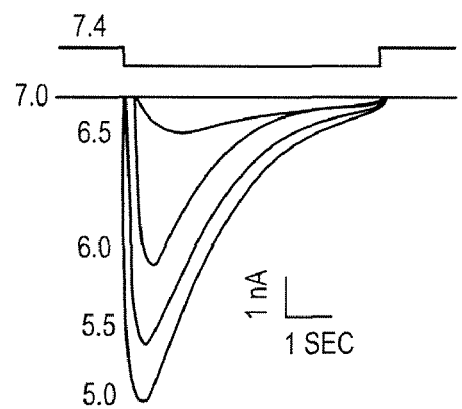
FIGS. 1A-D are graphs showing the pH dependence of ASIC current (A and B) and the linear current-voltage relationship of ASICs (C and D).

The instant invention provides novel methods and compositions for preventing and/or treating neuronal injury in mammalian subjects, including individuals and in vitro, ex vivo, and in vivo mammalian cells, tissues, and organs.

A broad range of mammalian subjects, including human subjects, are amenable to treatment using the formulations and methods of the invention. These subjects include, but are not limited to, human and other mammalian subjects presenting with those suffering from or at risk for neuronal injury including those with a history of seizures including, but not limited to, epilepsy; stroke including, but not limited to a major ischemic attack, a transient ischemic attach, and a hemorrhagic event; traumatic brain injury; surgery; infection; acidosis; ischemia; activation of one or more acid-sensing ion channels (with or without acidosis/ischemia); at risk for an ischemic event; at risk for stroke including a hemorrhagic stroke, an ischemic stroke, or the result of global ischemia (e.g., cardiac arrest); those with high cholesterol; metabolic disorder; hypoxia; high blood pressure; heart disease; irregular heart rhythms, such as atrial fibrillation, phlebitis, congestive heart failure; or any other disease or symptom that increases the likelihood of a neuronal injury such as those diseases and symptoms that put an individual at risk for a seizure or stroke.

Acidosis, as used herein, is any regional or global acidification of cells and/or tissue(s) of the body. The acidification may involve any suitable drop from (normal) physiological pH, such as about 0.1, 0.2, or 0.5 pH units, among others. In addition, the acidification may have any suitable cause, such as reduced blood flow (ischemia), increased metabolic activity (e.g., seizures), infection, a genetic defect, and/or the like.

Ischemia, as used herein, is a reduced blood flow to an organ(s) and/or tissue(s). The reduced blood flow may be caused by any suitable mechanism including a partial or complete blockage (an obstruction), a narrowing (a constriction), and/or a leak/rupture, among others, of one or more blood vessels that supply blood to the organ(s) and/or tissue(s). Accordingly, ischemia may be created by thrombosis, an embolism, atherosclerosis, hypertension, hemorrhage, an aneurysm, surgery, trauma, medication, or any other condition known to reduce blood flow. The reduced blood flow thus may be chronic, transient, acute, sporadic or any other characterization of fixed and/or variable reduced blood flow conditions.

Any suitable organ or tissue may experience a reduced blood flow in the ischemia being treated. Exemplary organs and/or tissues may include the brain, arteries, the heart, intestines, the eye (e.g., the optic nerve and/or retina), etc. Ischemia-induced injury (i.e., disease and/or damage) produced by various ischemias may include ischemic myelopathy, ischemic optic neuropathy, ischemic colitis, coronary heart disease, and/or cardiac heart disease (e.g., angina, heart attack, etc.), among others. Ischemia-induced injury thus may damage and/or kill cells and/or tissue, for example, producing necrotic (infarcted) tissue, inflammation, and/or tissue remodeling, among others, at affected sites within the body. Treatment according to aspects of the present teachings may reduce the incidence, extent, and/or severity of this injury.

Within the methods and compositions of the invention, one or more acid sensing ion channel (ASIC) inhibiting compound(s) as disclosed herein is/are effectively formulated or administered as a neuroprotective agent effective for treating and preventing brain injury and/or related disorders. In exemplary embodiments, PcTx1 is demonstrated for illustrative purposes to be an ASIC inhibiting effective agent in pharmaceutical formulations and therapeutic methods, alone or in combination with one or more adjunctive therapeutic agent(s). The present disclosure further provides additional, pharmaceutically acceptable neuroprotective compounds in the form of a native or synthetic compound, including complexes, derivatives, salts, solvates, isomers, enantiomers, polymorphs, and prodrugs of the compounds disclosed herein, and combinations thereof, which are effective as neuroprotective therapeutic agents within the methods and compositions of the invention.

ASICs belong to the degenerin/epithelial Na+ channel family of amiloride sensitive cation channels. They are widely distributed throughout the mammalian peripheral and central nervous system and have been implicated in many physiological and pathophysiological processes. Various ASIC subunits form homomultimeric and heteromultimeric channel complexes that vary in their expression within organs and are activated at different pH values (Krishtal, O. Trends Neurosci 26 477-483 (2003)).

Four of these subunits may form functional homomultimeric channels that are activated by acidic pH to conduct a sodium-selective, amiloride-sensitive, cation current. The pH of half-maximal activation ($pH_{0.5}$) of these channels differs: ASIC1a, $pH_{0.5}$=6.2 (Waldmann et al., 1997a); ASIC1β (also termed ASIC1b), a splice variant of ASIC1a with a unique N-terminal, $pH_{0.5}$=5.9 (Chen et al., 1998); ASIC2a, $pH_{0.5}$=4.4 (Waldmann et al., 1999); and ASIC3, $pH_{0.5}$=6.5 (Waldmann et al., 1997b). Neither ASIC2b nor ASIC4 can form functional homomeric channel (Akopian et al. 2000; Grunder et al. 2000 and Lingueglia et al. 1997), but ASIC2b has been shown to associate with other subunits and modulate their activity (Lingueglia et al., 1997). In addition to $Na^+$ permeability, homomeric ASIC1a may flux $Ca^{2+}$ (Waldmann et al. 1997a; Chu et al. 2002 and Yennolaieva et al. 2004). Of the six ASIC subunits cloned, ASIC1a, ASIC2a and ASIC2b, are expressed in brain neurons (Duggan, A., et al., *J. Biol Chem* 277:5203-5206 (2002); Lingueglia, E., et al., *J. Biol. Chem.* 272:29778-29783 (1997); Waldmann, R., et al., Nature 386:173-177 (1997); Waldmann, R., et al *J. Biol. Chem.* 271:10433-10436 (1996)).

Although the exact subunit composition of ASICs in native neurons has not been determined, both ASIC1a and ASIC2a subunits have been shown to be abundant in the brain (Price et al. 1996; Bassilana et al. 1997; Wemmie et al. 2002 and Alvarez de la Rosa et al. 2003).

Detailed functions of ASICs in both peripheral and central nervous systems remain to be determined. In peripheral sensory neurons, ASICs have been implicated in mechanosensation (Price et al. 2000 and Price et al. 2001) and perception of pain during tissue acidosis (Bevan and Yeats 1991; Krishtal and Pidoplichko 1981; Ugawa et al. 2002; Sluka et al. 2003 and Chen et al. 2002), particularly in ischemic myocardium where ASICs likely transduce anginal pain (Benson et al., 1999). The presence of ASICs in the brain, which lacks nociceptors, suggests that these channels may have functions beyond nociception. Indeed, recent studies have indicated that ASIC1a may be involved in synaptic plasticity, learning/memory, and fear conditioning (Wemmie et al. 2002 and Wemmie et al. 2003).

It is thought that ASIC1a, which has a pH for half maximal activation ($pH_{0.5}$) of 6.2 (Waldmann, R., et al., *Nature* 386: 173-177 (1997)) is the most likely ASIC activated in physiological and pathophysiological conditions. ASIC1a allows the passage of both Na$^+$ and Ca$^{2+}$ ions into the cells (Waldmann, R., et al., *Nature* 386:173-177 (1997); Wu, L. et al., *J. Biol. Chem* 279:43716-43724 (2004); (Yermolaieva, O., et al., *PNAS USA* 101: 6752-6757 (2004)) and is involved in both physiological (Wemmie, J. A., et al. *J Neurosci* 23:5496-5502 (2003); Wemmie, J. A., et al., *Neuron* 34:463-477 (2002); Wemmie, J. A., et al. *Proc Natl Acad Sci USA* 101: 3621-3626 (2004)) and pathological conditions (Allen, N. J., and Attwell, D. *J Physiol* 543:521-529 (2002); Diarra, A., Sheldon, C., Brett, C. L., Baimbridge, K. G., and Church, *J. Neuroscience* 93:1003-1016 (1999); Obrenovitch, T. P. et al., *J Neurophysiol* 64:1125-1133 (1990); Deitmer, J. W., and Rose, C. R. 48:73-103 (1996); Li, P. A., and Siesjo, B. K. *Acta Physiol Scand* 161:567-580 (1997)). In particular, the studies described in the examples below demonstrate that activation of ASIC1a is largely responsible for acidosis-mediated, glutamate independent neuronal injury.

Recently it has been reported that a simple molecule, the proton, plays a pivotal role in the development of the ischemic damage through activation of Ca$^{2+}$ permeable acid-sensing ion channel: ASIC1a (U.S. Provisional Patent Application No. 60/611,241 and PCT Patent Application Serial No. PCT/US2005/033171, Xiong, Z. G., et al. *Cell* 118:687-698 (2004); Yermolaieva, O., et al. *Proc Natl Acad Sci USA* 101: 6752-6757 (2004) each of which is incorporated by reference in their entirety). It has been known for several decades that acidosis occurs after ischemia and it is associated with neuronal injury. The experiments herein show that acidosis may activate Ca$^{2+}$-permeable acid-sensing ion channels (ASICs), which may induce glutamate receptor-independent, Ca$^{2+}$-dependent, neuronal injury inhibited by ASIC blockers. Cells lacking endogenous ASICs may be resistant to acid injury, while transfection of Ca$^{2+}$-permeable ASIC1a may establish sensitivity. In focal ischemia, intracerebroventricular injection of ASIC1a blockers or knockout of the ASIC1a gene may protect the brain from ischemic injury and may do so more potently than glutamate antagonism. Thus, acidosis may injure the brain via membrane receptor-based mechanisms with resultant toxicity of [Ca$^{2+}$]$_i$ (intracellular calcium), disclosing new potential therapeutic targets for stroke.

In particular, as previously reported (Back, T., Hoehn, M., Mies, G., Busch, E., Schmitz, B., Kohno, K., and Hossmann, *Ann Neurol* 47:485-492 (2000)), in the so-called penumbral region there is a initial pH alkalinization. Interestingly, during the development of the ischemic lesion, the core pH drops to values around 6.5. These levels are sufficient to activate ASIC1a channels, which have a pH$_{0.5}$ at 6.2 (Waldmann, R. *Adv Exp Med Biol* 502:293-304 (2001); Yermolaieva, O., Leonard, A. S., Schnizler, M. K., Abboud, F. M., and Welsh, M. J. *Proc Natl Acad Sci USA* 101:6752-6757 (2004)).

The alkalosis phenomenon of the penumbra has been previously described as resulting from the reduction of lactate formation, the elevated phosphorylation of adenosine nucleotides consuming H$^+$, and acceptance of protons by the Krebs cycle (Back, T., Hoehn, M., Mies, G., Busch, E., Schmitz, B., Kolmo, K., and Hossmann, *Ann Neurol* 47:485-492 (2000)). As shown in the experiments below, the alkalosis is transient and, after ~2 h of reperfusion (3 h after middle cerebral artery occlusion), the infarct reaches the parietal cortex and pH in this region drops to ~6.5, a level sufficient to activate ASIC1a.

Therefore the pH drop and activation of ASIC1a proceeds from the ischemic core to the peripheral ischemic region as infarction matures. This delayed acid expansion into cortical penumbral region may explain the long-term neuroprotective window affected by ASIC1a blockade, and thus the protection observed in the experiments herein with blockade 5 hours after stroke.

Any suitable ASIC inhibitor or combination of inhibitors may be used in the compositions and methods of the present invention. Inhibitors of ASIC family members, as used herein, are substances that reduce (partially, substantially, or completely block) the activity of one or more members of the ASIC family, that is, ASIC1a, ASIC1b, ASIC2a, ASIC2b, ASIC3, and ASIC4, among others. In some examples, the inhibitors may reduce the channel activity of one or more members, such as the ability of the members to flux ions (e.g., sodium, calcium, and/or potassium ions, among others) through cell membranes (into and/or out of cells). The substances may be compounds (small molecules of less than about 10 kDa, peptides, nucleic acids, lipids, etc.), complexes of two or more compounds, and/or mixtures, among others. Furthermore, the substances may inhibit ASIC family members by any suitable mechanism including competitive, non-competitive, uncompetitive, mixed inhibition, and/or by changing a subject's pH, among others. The expression "ASIC inhibitor" may refer to a product which, within the scope of sound pharmacological judgment, is potentially or actually pharmaceutically useful as an inhibitor of ASIC, and includes reference to substances which comprise a pharmaceutically active species and are described, promoted, and/or authorized as an ASIC inhibitor.

ASIC inhibitors may be selective with the ASIC family. For example, an ASIC1a inhibitor may have inhibition that is substantially stronger on ASIC1a than on another ASIC family member(s) when compared (for example, in cultured cells) after exposure of each to the same (sub-maximal) concentration(s) of an inhibitor. The inhibitor may inhibit ASIC1a selectively relative to at least one other ASIC family member (ASIC1b, ASIC2a, ASIC2b, ASIC3, ASIC 4, etc.) and/or selectively relative to every other ASIC family member. The strength of inhibition for a selective inhibitor may be described by an inhibitor concentration at which inhibition occurs (e.g., an IC$_{50}$ (inhibitor concentration that produces 50% of maximal inhibition) or a K$_i$ value (inhibition constant or dissociation constant)) relative to different ASIC family members. An ASIC1a-selective inhibitor may inhibit ASIC1a activity at a concentration that is at least about two-, four-, or ten-fold lower (one-half, one-fourth, or one-tenth the concentration or lower) than for inhibition of at least one other or of every other ASIC family member. Accordingly, an ASIC1a-selective inhibitor may have an IC$_{50}$ and/or K$_i$ for ASIC1a inhibition that is at least about two-, four-, or ten-fold lower (one-half, one-fourth, or one-tenth or less) than for inhibition of at least one other ASIC family member and/or for inhibition of every other ASIC family member.

ASIC inhibitors in addition to being selective may also be specific for particular channels within the ASIC family. For example, an ASIC1a-selective inhibitor, in addition to being selective, also may be specific for ASIC1a. ASIC1a-specific inhibition, as used herein, is inhibition that is substantially exclusive to ASIC1a relative to every other ASIC family member. An ASIC1a-specific inhibitor may inhibit ASIC1a at an inhibitor concentration that is at least about twenty-fold lower (5% of the concentration or less) than for inhibition of every other ASIC family member. Accordingly, an ASIC1a-specific inhibitor may have an IC$_{50}$ and/or K$_i$ for ASIC1a relative to every other member of the ASIC family that is at least about twenty-fold lower (five percent or less), such that, for example, inhibition of other ASIC family members is at least substantially (or completely) undetectable.

Any suitable ASIC inhibitor or combination of inhibitors may be used in the methods and compositions herein. For example, a subject may be treated with an ASIC1a-selective inhibitor and a nonselective ASIC inhibitor, or with an ASIC1a-selective inhibitor and an inhibitor to a non-ASIC channel protein, such as a non-ASIC calcium channel. In some examples, a subject may be treated with an ASIC1a-selective inhibitor and an inhibitor of a glutamate receptor. The glutamate inhibitor may selectively inhibit an ionotropic glutamate receptor (e.g., an NMDA receptor, an AMPA receptor, or a kainate receptor, among others) or a metabotropic glutamate receptor. Furthermore, the inhibitor may selectively inhibit an NMDA receptor that is, selectively relative to other receptors and/or relative to non-NMDA glutamate receptors.

In some embodiments, an ASIC inhibitor may be or may include a peptide. "Proteins", "peptides," "polypeptides" and "oligopeptides" as used herein are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the protein, or to the alpha-amino group (imino group when participating in a peptide bond) of an amino acid at any other location within the protein. Similarly, the term "carboxy terminus" (abbreviated C-terminus) refers to the free carboxyl group on the amino acid at the carboxy terminus of a protein, or to the carboxyl group of an amino acid at any other location within the protein. In keeping with standard polypeptide nomenclature, the following abbreviations for amino acids may be used herein to describe various ASIC inhibitors in the compositions and the methods of the present invention.

| SYMBOL | | |
|---|---|---|
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| Z | Glx | L-glutamic acid or L-glutamine |
| W | Trp | L-tryptophan |
| R | Arg | L-arginine |
| D | Asp | L-aspartic acid |
| N | Asn | L-asparagine |
| B | Asx | L-aspartic acid or L-asparagine |
| C | Cys | L-cysterine |

Figure 10:
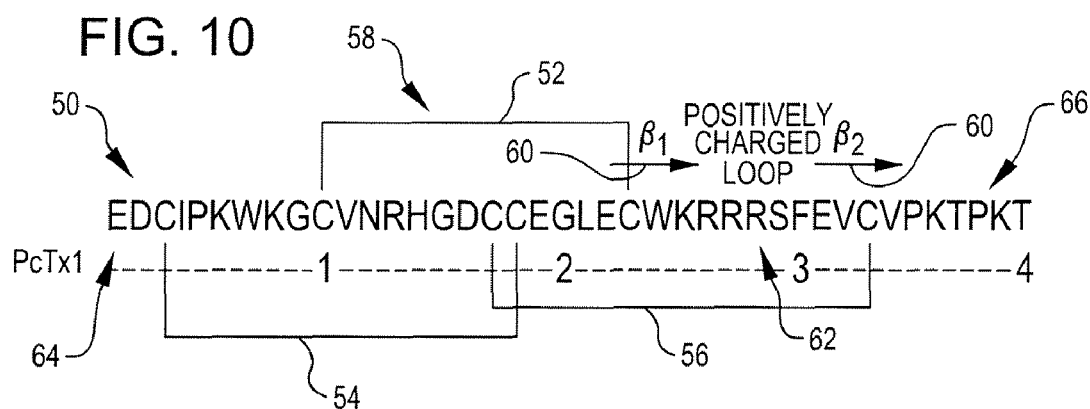
FIG. 10 shows the primary amino acid sequence (SEQ ID NO:1), in one-letter code, of an exemplary cystine knot peptide, PcTx1, indicated at 50, with various exemplary peptide features shown relative to amino acid positions 1-40.

An ASIC inhibitor may have any suitable number of amino acid subunits (also termed residues), generally at least about ten and less than about one-thousand subunits. In some examples, the peptide may have a cystine knot motif. A cystine knot, as used herein, generally comprises an arrangement of six or more cysteines. A peptide with these cysteines may create a "knot" including (1) a ring formed by two disulfide bonds and their connecting backbone segments, and (2) a third disulfide bond that threads through the ring. In some examples, the peptide may be a conotoxin from an arachnid and/or cone snail species. An exemplary peptide is PcTx1 (psalmotoxin 1), a toxin from a tarantula (*Psalmopoeus cambridgei* (Pc)) which has the amino acid sequence: EDCIPKWKGCVNRHGDCCEGLECWKRRRSFEVGVPKTPKT (SEQ ID NO. 1, FIG. 10). As shown in FIG. 10, PcTx1 may include six cystine residues that form cystine bonds 52, 54, and 56 to create a cystine knot motif 58. The peptide also may include one or more beta sheet regions 60 and a positively charged region 62. An N-terminal region 64 and a C-terminal region 66 may flank the cystine knot motif.

One of skill in the art will recognize that individual substitutions, deletions or additions which alter, add or delete a single amino acid or a small percentage of amino acids (less than about 30%, typically less than about 20%, typically less than about 10%, more typically less than about 5%, typically less than about 3%, typically less than about 1%) in an encoded sequence are conservatively modified variations where the alterations result in the substitution of an amino acid with a chemically similar amino acid. "Conservative substitution" in the context of the subject invention is one in which an amino acid is substituted for another amino acid that has similar properties, such that one skilled in the art of peptide chemistry would expect the secondary structure of the polypeptide to be substantially unchanged for these regions. For example, the amino acid residues arginine, histidine and lysine are hydrophilic, basic amino acid residues and may therefore be interchangeable. Similarly, the amino acid residue isoleucine, which is a hydrophobic amino acid residue, may be replaced with leucine, methionine or valine. Such changes are expected to have little or no effect on the apparent molecular weight or isoelectric point of the polypeptide.

The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Variants of PcTx1 will possess a relatively high degree of sequence identity when aligned using standard methods.

Methods of alignment of sequences for comparison are well known in the art. Altschul et al. (1994) presents a detailed consideration of sequence alignment methods and homology calculations. The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website. A description of how to determine sequence identity using this program is available at the NCBI website, as are the default parameters.

Variants of PcTx1 peptides are typically characterized by possession of at least 90%, 80%, 78%, 75%, 74%, 50% sequence identity counted over the full length alignment with the amino acid sequence of a native PcTx1 peptide using the NCBI Blast 2.0, gapped blastp set to default parameters. Proteins with even greater similarity to the reference sequences will show increasing percentage identities when assessed by this method, such as at least 60%, at least 65%, at least 70%, at least 75%, at least 77%, at least 80%, at least 90% or at least 95% amino acid sequence identity. When less than the entire sequence is being compared for sequence identity, variants will typically possess at least 75% sequence identity over short windows of 10-20 amino acids, and may possess sequence identities of at least 85% or at least 90% or 95% depending on their similarity to the reference sequence. Methods for determining sequence identity over such short windows are described at the NCBI website. Variants of PcTx1 peptides polypeptides also retain the biological activity of the native polypeptide.

Exemplary PcTx1 variants may include, for example, an N-terminal deletion 70 so that the resulting sequence is CIPKWKGCVNRHGDCCEGLECWKRRRSFEVCVPKTPKT (SEQ ID NO:2); a partial C-terminal deletion 72 so that the resulting sequence is EDCIPKWKGCVNRHGDCCEGLECWKRRRSFEVCVPKTPKT (SEQ ID NO:3); a full C-terminal deletion 74 so that the resulting sequence is EDCIPKWKGCVNRHGDCCEGLECWKRRRSFEVCVP (SEQ ID NO:4); or an N/C terminal deletion 76 so that the resulting sequence is CIPKWKGCVNRHGDCCEGLECWKRRRSFEVC (SEQ ID NO:5). (FIG. 11) Other derivatives of PcTx1 may include any deletion, insertion, or substitution of one or more amino acids in SEQ ID NO: 1, for example, while maintaining sequence similarity or identity of at least about 25% or about 50% with the original PcTx1 sequence.

When the peptides are relatively short in length (i.e., less than about 50 amino acids), they are often synthesized using standard chemical peptide synthesis techniques. Solid phase synthesis in which the C-terminal amino acid of the sequence is attached to an insoluble support followed by sequential addition of the remaining amino acids in the sequence is a preferred method for the chemical synthesis of the peptides described herein. Techniques for solid phase synthesis are known to those skilled in the art.

Alternatively, the peptides described herein are synthesized using recombinant nucleic acid methodology. Generally, this involves creating a nucleic acid sequence that encodes the peptide or protein, placing the nucleic acid in an expression cassette under the control of a particular promoter, expressing the peptide or protein in a host, isolating the expressed peptide or protein and, if required, renaturing the peptide or protein. Techniques sufficient to guide one of skill through such procedures are found in the literature.

When several desired protein fragments or peptides are encoded in the nucleotide sequence incorporated into a vector, one of skill in the art will appreciate that the protein fragments or peptides may be separated by a spacer molecule such as, for example, a peptide, consisting of one or more amino acids. Generally, the spacer will have no specific biological activity other than to join the desired protein fragments or peptides together, or to preserve some minimum distance or other spatial relationship between them. However, the constituent amino acids of the spacer may be selected to influence some property of the molecule such as the folding, net charge, or hydrophobicity. Nucleotide sequences encoding for the production of residues which may be useful in purification of the expressed recombinant protein may be built into the vector. Such sequences are known in the art. For example, a nucleotide sequence encoding for a poly histidine sequence may be added to a vector to facilitate purification of the expressed recombinant protein on a nickel column.

Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents.

One of skill in the art will recognize that after chemical synthesis, biological expression or purification, the desired proteins, fragments thereof and peptides may possess a conformation substantially different than the native conformations of the proteins, fragments thereof and peptides. In this case, it is often necessary to denature and reduce protein and then to cause the protein to re-fold into the preferred conformation. Methods of reducing and denaturing proteins and inducing re-folding are well known to those of skill in the art.

Each PcTx1 variant or derivative may be tested for its ability to inhibit ASIC proteins selectively and/or for an effect, if any, on neuronal injury. Any suitable test system(s) may be used to perform this testing including any of the cell-based assay systems and/or animal model systems described elsewhere in the present teachings. The PcTx1 derivative also or alternatively may be tested in ischemic human subjects.

ASIC inhibiting compositions comprising PcTX1 and variants thereof, including pharmaceutical formulations of the invention, comprise a neuroprotective effective amount of an ASIC inhibiting compound, which is effective for prophylaxis and/or treatment of brain injury in a mammalian subject. Typically, a neuroprotective effective amount, of a compound will comprise an amount of the active compound which is therapeutically effective, in a single or multiple unit dosage form, over a specified period of therapeutic intervention, to measurably alleviate one or more symptoms of brain injury in the subject, and/or to alleviate one or more symptom(s) of stroke, seizure or related conditions in the subject. Within exemplary embodiments, these compositions are effective within in vivo treatment methods to alleviate brain injury.

ASIC inhibiting compositions of the invention typically comprise a neuroprotective effective amount or unit dosage of a PcTX1 peptide or variant thereof, which may be formulated with one or more pharmaceutically acceptable carriers, excipients, vehicles, emulsifiers, stabilizers, preservatives, buffers, and/or other additives that may enhance stability, delivery, absorption, half-life, efficacy, pharmacokinetics, and/or pharmacodynamics, reduce adverse side effects, or provide other advantages for pharmaceutical use. Neuroprotective effective amounts of a PcTX1 peptide or variant thereof or other ASIC inhibiting compound (e.g., a unit dose comprising an effective concentration/amount of ASIC inhibiting compound) will be readily determined by those of ordinary skill in the art, depending on clinical and patient-specific factors. Suitable effective unit dosage amounts of the active compounds for administration to mammalian subjects, including humans, may range from 10 to 1500 mg, 20 to 1000 mg, 25 to 750 mg, 50 to 500 mg, or 150 to 500 mg. In certain embodiments, the neuroprotective effective dosage of an ASIC inhibiting compound may be selected within narrower ranges of, for example, 10 to 25 mg, 30 to 50 mg, 75 to 100 mg, 100 to 250 mg, or 250 to 500 mg. These and other effective unit dosage amounts may be administered in a single dose, or in the form of multiple daily, weekly or monthly doses, for example in a dosing regimen comprising from 1 to 5, or 2-3, doses administered per day, per week, or per month. In one exemplary embodiment, dosages of 10 to 25 mg, 30 to 50 mg, 75 to 100 mg, 100 to 250 mg, or 250 to 500 mg, are administered one, two, three, four, or five times per day. In more detailed embodiments, dosages of 50-75 mg, 100-200 mg, 250-400 mg, or 400-600 mg are administered once or twice daily. In alternate embodiments, dosages are calculated based on body weight, and may be administered, for example, in amounts from about 0.5 mg/kg to about 100 mg/kg per day, 1 mg/kg to about 75 mg/kg per day, 1 mg/kg to about 50 mg/kg per day, 2 mg/kg to about 50 mg/kg per day, 2 mg/kg to about 30 mg/kg per day or 3 mg/kg to about 30 mg/kg per day. In some embodiments, an ASIC inhibiting compound may be effective if given within a particular time period after the occurrence of a brain injuring event. For example, an ASIC inhibiting compound may be effective if given within 1, 2, 3, 4, 5, 6, 7 or more hours of the event. In other embodiments, an ASIC inhibiting compound may be administered prophalactically.

The amount, timing and mode of delivery of compositions of the invention comprising a neuroprotective effective amount of a ASIC inhibiting compound will be routinely adjusted on an individual basis, depending on such factors as weight, age, gender, and condition of the individual, the acuteness of the brain injury and/or related symptoms, whether the administration is prophylactic or therapeutic, and on the basis of other factors known to effect drug delivery, absorption, pharmacokinetics, including half-life, and efficacy.

An effective dose or multi-dose treatment regimen for the instant ASIC inhibiting formulations will ordinarily be selected to approximate a minimal dosing regimen that is necessary and sufficient to substantially prevent or alleviate neuronal damage or acidosis in the subject, and/or to substantially prevent or alleviate one or more symptoms associated with neuronal damage or acidosis in the subject. A dosage and administration protocol will often include repeated dosing therapy over a course of several days or even one or more weeks or years. An effective treatment regime may also involve prophylactic dosage administered on a day or multi-dose per day basis lasting over the course of days, weeks, months or even years.

Various assays and model systems can be readily employed to determine the therapeutic effectiveness of an ASIC inhibitor. Screening may involve any suitable assay system that measures interaction between ASIC proteins and the set of candidate inhibitors. Exemplary assay systems may include assays performed biochemically (e.g., binding assays), with cells grown in culture ("cultured cells"), and/or with organisms, among others.

A cell-based assay system may measure an effect, if any, of each candidate inhibitor on ion flux in the cells, generally acid-sensitive ion flux. In some examples, the ion flux may be a flux of calcium and/or sodium, among others. The assay system may use cells expressing an ASIC family member, such as ASIC1a, or two or more distinct sets of cells expressing two or more distinct ASIC family members, such as ASIC1a and another ASIC family member(s), to determine the selectivity of each inhibitor for these family members. The cells may express each ASIC family member endogenously or through introduction of foreign nucleic acid. In some examples, the assay system may measure ion flux electrophysiologically (such as by patch clamp), using an ion-sensitive or membrane potential-sensitive dye (e.g., a calcium sensitive dye such as Fura-2), or via a gene-based reporter system that is sensitive to changes in membrane potential and/or intracellular ion (e.g., calcium) concentrations, among others. The assay system may be used to test candidate inhibitors for selective and/or specific inhibition of ASIC family members, particularly ASIC1a.

Any suitable seizure/epilepsy model system(s) may be used to test candidate bioactive compositions and/or treatment regimens with the bioactive compositions. Accordingly, the candidate compositions may be tested in cell culture systems, tissue explant systems, and/or in whole animals. Furthermore, seizure-like activity or seizures may be induced by any suitable approach, including electrical stimulation, contact with a bioactive composition, a change in oxygen concentration (e.g., hypoxia or anoxia), and/or trauma, among others.

Candidate inhibitors also or alternatively may be tested in tissue-based assay systems. For example, candidate inhibitors may be tested on explants of brain tissue, such as hippocampal slices, among others.

One or more ASIC inhibitors may be administered to an ischemic subject(s) to test the efficacy of the inhibitors for treatment of ischemia. The ischemic subjects may be people or animals. In some examples, the ischemic subjects may provide an animal model system of stroke and/or epilepsy. Exemplary animal model systems include rodents (mice and/or rats, among others) with ischemia and/or seizure(s) induced experimentally. The ischemia and/or seizure(s) may be induced mechanically (e.g., surgically) and/or by administration of a drug, among others. In some examples, the ischemia may be induced by occlusion of a blood vessel, such as by constriction of a mid-cerebral artery.

Effectiveness of the compositions and methods of the invention may also be demonstrated by a decrease in the occurrence and symptoms of stroke or seizure including a decrease in abnormal synchronization of a group of brain cells, such that the brain cells exhibit normal electrical activity; there is a decrease in acidosis in the brain, a reduction or prevention of hemiparesis, hemiplegia, one-sided numbness, one-sided weakness, one-sided paralysis, temporary limb weakness, limb tingling, confusion, trouble speaking, trouble understanding speech, trouble seeing in one or both eyes, dim vision, loss of vision, trouble walking, dizziness, a tendency to fall, loss of coordination, sudden severe headache, noisy breathing, and/or loss of consciousness. In some embodiments, a reduction or elimination of symptoms may be determined by observation. In other embodiments, a reduction or elimination of symptoms may be determined by tests and/or instruments.

Effectiveness of the compositions and methods of the invention may also be demonstrated by an increase in the pH of the brain of a mammalian subject.

For each of the indicated conditions described herein, test subjects will exhibit a 10%, 20%, 30%, 50% or greater reduction, up to a 75-90%, or 95% or greater, reduction, in one or more symptom(s) caused by, or associated with, brain injury or condition in the subject, compared to placebo-treated or other suitable control subjects.

Within additional aspects of the invention, combinatorial ASIC inhibiting formulations and coordinate administration methods are provided which employ an effective amount of an ASIC inhibitor compound and one or more secondary or adjunctive agent(s) that is/are combinatorially formulated or coordinately administered with an ASIC inhibitor compound to yield a combined, multi-active agent neuroprotective (and/or acidosis reducing) composition or coordinate treatment method. Exemplary combinatorial formulations and coordinate treatment methods in this context employ the ASIC inhibitor in combination with the one or more secondary neuroprotective agent(s), or with one or more adjunctive therapeutic agent(s) that is/are useful for treatment or prophylaxis of the targeted (or associated) disease, condition and/or symptom(s) in the selected combinatorial formulation or coordinate treatment regimen. For most combinatorial formulations and coordinate treatment methods of the invention, an ASIC inhibiting compound is formulated, or coordinately administered, in combination with one or more secondary or adjunctive therapeutic agent(s), to yield a combined formulation or coordinate treatment method that is combinatorially effective or coordinately useful to treat or prevent brain injury and/or one or more symptom(s) of a brain injury or condition in the subject. Exemplary combinatorial formulations and coordinate treatment methods in this context employ an ASIC inhibiting compound in combination with one or more secondary or adjunctive therapeutic agents selected from, e.g., an antagonist selective for a glutamate receptor, such as an NMDA-receptor inhibitor including, but not limited to, ketamine, dextromethorphan, memantine, amantadine, 2-amino-5-phosphonopentanoate (AP5), dizocilipine, phencyclidine, riluzole, and cis-4-[phosphonomethyl]-2-piperidine carboxylic acid; an alkalinizing agent such as sodium bicarbonate; nitroglycerin; anticoagulant medications, such as warfarin, dicumarol, anisinidione, and heparin; tissue plasminogen activator; aspirin; and anti-platelet agents including, but not limited to, clopidogrel bisulfate.

In certain embodiments the invention provides combinatorial neuroprotective (acidosis decreasing) formulations comprising an ASIC inhibiting compound and one or more adjunctive agent(s) having neuroprotective activity. Within such combinatorial formulations, the ASIC inhibiting compound and the adjunctive agent(s) having neuroprotective activity will be present in a combined formulation in neuroprotective effective amounts, alone or in combination. In exemplary embodiments, an ASIC inhibiting compound and a non-ASIC inhibiting agent(s) will each be present in neuroprotective amounts (i.e., in singular dosage which will alone elicit a detectable neuroprotective and/or acidosis decreasing response in the subject). Alternatively, the combinatorial formulation may comprise one or both of the ASIC inhibiting and non-ASIC inhibiting agents in sub-therapeutic singular dosage amount(s), wherein the combinatorial formulation comprising both agents features a combined dosage of both agents that is collectively effective in eliciting a neuroprotective (acidosis decreasing) response. Thus, one or both of the ASIC inhibiting and non-ASIC inhibiting agents may be present in the formulation, or administered in a coordinate administration protocol, at a sub-therapeutic dose, but collectively in the formulation or method they elicit a detectable neuroprotective response in the subject.

To practice coordinate administration methods of the invention, an ASIC inhibiting compound may be administered, simultaneously or sequentially, in a coordinate treatment protocol with one or more of the secondary or adjunctive therapeutic agents contemplated herein. Thus, in certain embodiments a compound is administered coordinately with a non-ASIC inhibiting agent, or any other secondary or adjunctive therapeutic agent contemplated herein, using separate formulations or a combinatorial formulation as described above (i.e., comprising both an ASIC inhibiting agent, and a non-ASIC inhibiting therapeutic agent). This coordinate administration may be done simultaneously or sequentially in either order, and there may be a time period while only one or both (or all) active therapeutic agents individually and/or collectively exert their biological activities. In some embodiments, the ASIC inhibitor and the non-ASIC inhibiting agent or other secondary or adjunctive therapeutic agent may be administered by the same or different routes of administration. A distinguishing aspect of all such coordinate treatment methods is that the ASIC inhibiting exerts at least some neuroprotective activity, which yields a favorable clinical response in conjunction with a complementary neuroprotective, or distinct, clinical response provided by the secondary or adjunctive therapeutic agent. Often, the coordinate administration of the ASIC inhibiting agent with the secondary or adjunctive therapeutic agent will yield improved therapeutic or prophylactic results in the subject beyond a therapeutic effect elicited by the ASIC inhibiting agent, or the secondary or adjunctive therapeutic agent administered alone. This qualification contemplates both direct effects, as well as indirect effects.

Within exemplary embodiments, an ASIC inhibiting agent will be coordinately administered (simultaneously or sequentially, in combined or separate formulation(s)), with one or more secondary neuroprotective agents, or other indicated therapeutic agents, e.g., selected from, for example, an antagonist selective for a glutamate receptor, such as an NMDA-receptor inhibitor including, but not limited to, ketamine, dextromethorphan, memantine, amantadine, 2-amino-5-phosphonopentanoate (AP5), dizocilipine, phencyclidine, riluzole, and cis-4-[phosphonomethyl]-2-piperidine carboxylic acid; an alkalinizing agent, such as sodium bicarbonate; nitroglycerin; anticoagulant medications, such as warfarin, dicumarol, anisinidione, and heparin; tissue plasminogen activator; aspirin; and anti-platelet agents including, but not limited to, clopidogrel bisulfate.

As noted above, in all of the various embodiments of the invention contemplated herein, the neuroprotective (acidosis decreasing) methods and formulations may employ an ASIC inhibiting agent or other therapeutic agent in any of a variety of forms, including any one or combination of the subject compound's pharmaceutically acceptable salts, isomers, enantiomers, polymorphs, solvates, hydrates, and/or prodrugs. In exemplary embodiments of the invention, PcTx1 is employed within the therapeutic formulations and methods for illustrative purposes.

The pharmaceutical compositions of the present invention may be administered by any means that achieve their intended therapeutic or prophylactic purpose. Suitable routes of administration for the compositions of the invention include, but are not limited to, oral, buccal, nasal, aerosol, topical, transdermal, mucosal, injectable, slow release, controlled release, iontophoresis, sonophoresis, and including all other conventional delivery routes, devices and methods. Injectable methods include, but are not limited to, intravenous, intramuscular, intraperitoneal, intraspinal, intrathecal, intracerebroventricular, intraarterial, subcutaneous and intranasal routes.

The compositions of the present invention may further include a pharmaceutically acceptable carrier appropriate for the particular mode of administration being employed. Dosage forms of the compositions of the present invention include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, wetting agents, disintegrants, effervescent agents and other conventional excipients and additives.

If desired, the compositions of the invention can be administered in a controlled release form by use of a slow release carrier, such as a hydrophilic, slow release polymer. Exemplary controlled release agents in this context include, but are not limited to, hydroxypropyl methyl cellulose, having a viscosity in the range of about 100 cps to about 100,000 cps or other biocompatible matrices such as cholesterol.

Compositions of the invention will often be formulated and administered in an oral dosage form, optionally in combination with a carrier or other additive(s). Suitable carriers common to pharmaceutical formulation technology include, but are not limited to, microcrystalline cellulose, lactose, sucrose, fructose, glucose, dextrose, or other sugars, di-basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof. Exemplary unit oral dosage forms for use in this invention include tablets, which may be prepared by any conventional method of preparing pharmaceutical oral unit dosage forms can be utilized in preparing oral unit dosage forms. Oral unit dosage forms, such as tablets, may contain one or more conventional additional formulation ingredients, including, but not limited to, release modifying agents, glidants, compression aides, disintegrants, lubricants, binders, flavors, flavor enhancers, sweeteners and/or preservatives. Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate. Substances which may be used for coating include hydroxypropyl cellulose, titanium oxide, talc, sweeteners and colorants.

Additional compositions of the invention can be prepared and administered in any of a variety of inhalation or nasal delivery forms known in the art. The intra nasal route is recognized as providing a method for bypassing the blood brain barrier and directly delivering therapeutic drugs to the central nervous system. This form of administration may be particularly useful in instances of brain injury. Devices capable of depositing aerosolized purified ASIC inhibiting formulations in the sinus cavity or pulmonary alveoli of a patient include metered dose inhalers, nebulizers, dry powder generators, sprayers, and the like. Methods and compositions suitable for pulmonary delivery of drugs for systemic effect are well known in the art. Additional possible methods of delivery include deep lung delivery by inhalation. Suitable formulations, wherein the carrier is a liquid, for administration, as for example, a nasal spray or as nasal drops, may include aqueous or oily solutions of ASIC inhibiting compositions and any additional active or inactive ingredient(s).

Further compositions and methods of the invention are provided for topical administration of an ASIC inhibiting compound for the treatment of brain injury. Topical compositions may comprise an ASIC inhibiting compound along with one or more additional active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may comprise a ASIC inhibiting compound dissolved or dispersed in a portion of a water or other solvent or liquid to be incorporated in the topical composition or delivery device. It can be readily appreciated that the transdermal route of administration may be enhanced by the use of a dermal penetration enhancer known to those skilled in the art. Formulations suitable for such dosage forms incorporate excipients commonly utilized therein, particularly means, e.g. structure or matrix, for sustaining the absorption of the drug over an extended period of time, for example, 24 hours. Transdermal delivery may also be enhanced through techniques such as sonophoresis.

Yet additional ASIC inhibiting compositions of the invention are designed for parenteral administration, e.g. to be administered intravenously, intramuscularly, subcutaneously or intraperitoneally, including aqueous and non-aqueous sterile injectable solutions which, like many other contemplated compositions of the invention, may optionally contain antioxidants, buffers, bacteriostats and/or solutes which render the formulation isotonic with the blood of the mammalian subject; and aqueous and non-aqueous sterile suspensions which may include suspending agents and/or thickening agents. The formulations may be presented in unit-dose or multi-dose containers. Additional compositions and formulations of the invention may include polymers for extended release following parenteral administration. The parenteral preparations may be solutions, dispersions or emulsions suitable for such administration. The subject agents may also be formulated into polymers for extended release following parenteral administration. Pharmaceutically acceptable formulations and ingredients will typically be sterile or readily sterilizable, biologically inert, and easily administered. Such polymeric materials are well known to those of ordinary skill in the pharmaceutical compounding arts. Parenteral preparations typically contain buffering agents and preservatives, and injectable fluids that are pharmaceutically and physiologically acceptable such as water, physiological saline, balanced salt solutions, aqueous dextrose, glycerol or the like. Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

In more detailed embodiments, compositions of the invention may comprise an ASIC inhibiting compound encapsulated for delivery in microcapsules, microparticles, or microspheres, prepared, for example, by coaceivation techniques or by interfacial polymerization, for example, hydroxymethylcellulose or gelatin-microcapsules and poly(methylmethacylate) microcapsules, respectively; in colloidal drug delivery systems (for example, liposomes, albumin microspheres, microemulsions, nano-particles and nanocapsules); or within macroemulsions.

Other detailed embodiments, the methods and compositions of the invention for employ prodrugs of ASIC inhibiting agents. Prodrugs are considered to be any covalently bonded carriers which release the active parent drug in vivo. Examples of prodrugs useful within the invention include esters or amides with hydroxyalkyl or aminoalkyl as a substituent, and these may be prepared by reacting such compounds as described above with anhydrides such as succinic anhydride.

The invention disclosed herein will also be understood to encompass methods and compositions comprising ASIC inhibiting agents using in vivo metabolic products of the said compounds (either generated in vivo after administration of the subject precursor compound, or directly administered in the form of the metabolic product itself). Such products may result for example from the oxidation, reduction, hydrolysis, amidation, esterification and the like of the administered compound, primarily due to enzymatic processes. Accordingly, the invention includes methods and compositions of the invention employing compounds produced by a process comprising contacting an ASIC inhibiting compound with a mammalian subject for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein will also be understood to encompass diagnostic compositions for diagnosing the risk level, presence, severity, or treatment indicia of, or otherwise managing a brain injury or condition in a mammalian subject, comprising contacting a labeled (e.g., isotopically labeled, fluorescent labeled or otherwise labeled to permit detection of the labeled compound using conventional methods) ASIC inhibiting compound to a mammalian subject (e.g., to a cell, tissue, organ, or individual) at risk or presenting with one or more symptom(s) of brain injury, and thereafter detecting the presence, location, metabolism, and/or binding state (e.g., detecting binding to an unlabeled binding partner involved in ASIC receptor physiology/metabolism) of the labeled compound using any of a broad array of known assays and labeling/detection methods. In exemplary embodiments, a ASIC inhibiting compound is isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. The isotopically-labeled compound is then administered to an individual or other subject and subsequently detected as described above, yielding useful diagnostic and/or therapeutic management data, according to conventional techniques.

EXAMPLES

The experiments herein below demonstrate a new mechanism of ischemic brain injury and the role of ischemic acidosis in this biology. It is demonstrated herein that, after ischemia, pH is subjected to dynamic changes and that pH values change before the development of the ischemic lesion, reaching values capable of activating ASIC1a at different times and different phases of injury The experiments additionally demonstrate the effectiveness of PcTX1 and synthetic PcTX1 in inhibiting ASIC and preventing neuronal injury. It has been determined herein that PcTX is able to reduce the infarct volume even if administered after permanent occlusion of the middle cerebral artery. This finding indicates that the ASIC activation in the penumbra is present in the absence of reperfusion. Furthermore, the finding that PcTX administration reduced the lesion for at least 7 days suggests that acute ASIC blockade does not simply delay the injury process.

Additionally the experiments herein demonstrate that PcTX1 is effective in combinatorial therapy with other neuroprotective compounds. For example, the data herein demonstrate that the combined therapy of the ASIC1a blockade and the NMDA antagonism resulted in a further reduction of brain damage, as compared with the effects of the individual compounds, and also extended the therapeutic time window for NMDA blockade.

Example I

Electrophysiology of ASIC in Mouse Cortices

Following anesthesia with halothane, cerebral cortices were dissected from E16 Swiss mice or P1 ASIC1$^{+/+}$ and ASIC1$^{-/-}$ mice and incubated with 0.05% trypsin-EDTA for 10 min at 37° C. Tissues were then triturated with fire-polished glass pipettes and plated on poly-L-ornithine-coated 24-well plates or 25×25 mm glass coverslips at a density of $2.5 \times 10^5$ cells per well or $10^6$ cells per coverslip. Neurons were cultured with MEM supplemented with 10% horse serum (for E16 cultures) or Neurobasal medium supplemented with B27 (for P1 cultures) and used for electrophysiology and toxicity studies after 12 days. Glial growth was suppressed by addition of 5-fluoro-2-deoxyuridine and uridine, yielding cultured cells with ~90% neurons as determined by NeuN and GFAP staining (data not shown).

ASIC currents were recorded with whole-cell patch-clamp and fast-perfusion techniques. The normal extracellular solution (ECF) contained (in mM) 140 NaCl, 5.4 KCl, 25 HEPES, 20 glucose, 1.3 CaCl$_2$, 1.0 MgCl$_2$, 0.0005 TTX (pH 7.4), 320-335 mOsm. For low pH solutions, various amounts of HCl were added. For solutions with pH<6.0, MES instead of HEPES was used for more reliable pH buffering. Patch electrodes contained (in mM) 140 CsF, 2.0 MgCl$_2$, 1.0 CaCl$_2$, 10 HEPES, 11 EGTA, 4 MgATP (pH 7.3), 300 mOsm. The Na$^+$-free solution consisted of 10 mM CaCl$_2$, 25 mM HEPES with equiosmotic NMDG or sucrose substituting for NaCl (Chu et al., 2002). A multi-barrel perfusion system (SF-77B, Warner Instrument Co.) was employed for rapid exchange of solutions.

Figure 1B:
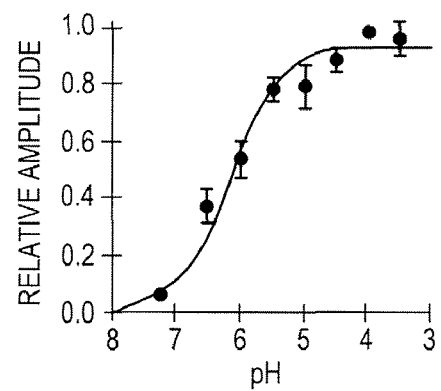
Figure 1C:
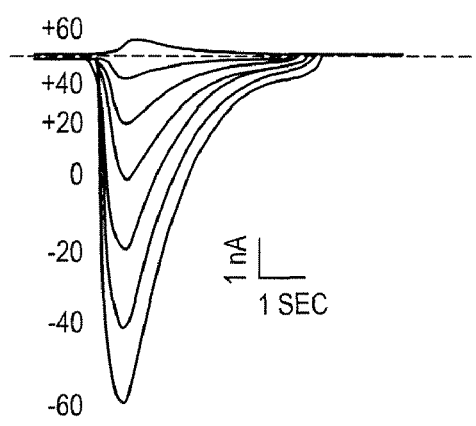
Figure 1D:
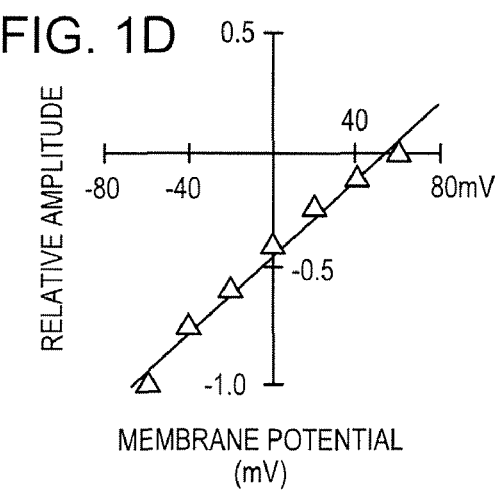

At a holding potential of −60 mV, a rapid reduction of extracellular pH (pH$_e$) to below 7.0 evoked large transient inward currents with a small steady-state component in the majority of neurons (FIG. 1A). The amplitude of inward current increased in a sigmoidal fashion as pH$_e$ decreased, yielding a pH$_{0.5}$ of 6.18±0.06 (n=10, FIG. 1B). A linear I-V relationship and a reversal close to the Na$^+$ equilibrium potential were obtained (n=6, FIGS. 1C and 1D). These data demonstrate that lowering pH$_e$ may activate typical ASICs in mouse cortical neurons.

Example II

Inhibitors of ASIC in Mouse Cortices

To test inhibition, the effect of 0.1, 1 10, and 1000 μM of amiloride, a nonspecific blocker of ASICs (Waldmann et al., 1997a) was used on the acid-activated currents and the results were compared to the effect of 100 ng/ml of Psalmotoxin 1 (PcTx1) from the venom of the tarantula *Psalmopoeus cambridgei* (PcTX venom).

Following anesthesia with halothane, cerebral cortices were dissected from E16 Swiss mice or P1 ASIC1$^{+/+}$ and ASIC1$^{-/-}$ mice and incubated with 0.05% trypsin-EDTA for 10 min at 37° C. Tissues were then triturated with fire-polished glass pipettes and plated on poly-L-ornithine-coated 24-well plates or 25×25 mm glass coverslips at a density of $2.5 \times 10^5$ cells per well or $10^6$ cells per coverslip. Neurons were cultured with MEM supplemented with 10% horse serum (for E16 cultures) or Neurobasal medium supplemented with B27 (for P1 cultures) and used for electrophysiology and toxicity studies after 12 days. Glial growth was suppressed by addition of 5-fluoro-2-deoxyuridine and uridine, yielding cultured cells with ~90% neurons as determined by NeuN and GFAP staining (data not shown).

ASIC currents were recorded with whole-cell patch-clamp and fast-perfusion techniques. The normal extracellular solution (ECF) contained (in mM) 140 NaCl, 5.4 KCl, 25 HEPES, 20 glucose, 1.3 CaCl$_2$, 1.0 MgCl$_2$, 0.0005 TTX (pH 7.4), 320-335 mOsm. For low pH solutions, various amounts of HCl were added. For solutions with pH<6.0, MES instead of HEPES was used for more reliable pH buffering. Patch electrodes contained (in mM) 140 CsF, 2.0 MgCl$_2$, 1.0 CaCl$_2$, 10 HEPES, 11 EGTA, 4 MgATP (pH 7.3), 300 mOsm. The Na$^+$-free solution consisted of 10 mM CaCl$_2$, 25 mM HEPES with equiosmotic NMDG or sucrose substituting for NaCl (Chu et al., 2002). A multi-barrel perfusion system (SF-77B, Warner Instrument Co.) was employed for rapid exchange of solutions.

Figure 2A:
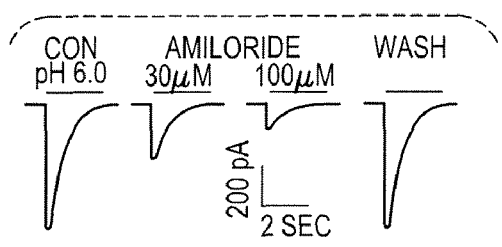
FIGS. 2 A-D are graphs illustrating a dose-dependent blockade of ASIC currents by amiloride (A and B) and PcTX venom (C and D). $**p<0.01$.
Figure 2B:
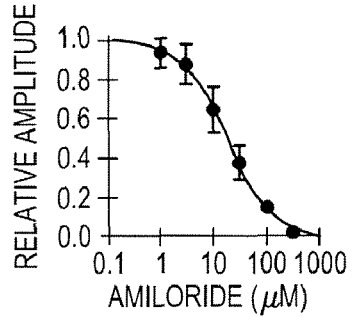

Similar to previous studies, mainly in sensory neurons (Waldmann et al. 1997a; Benson et al. 1999; Chen et al. 1998 and Varming 1999), amiloride dose-dependently blocked ASIC currents in cortical neurons with an $IC_{50}$ of 16.4±4.1 µM (n=8, FIGS. 2A and 2B).

Figure 2C:
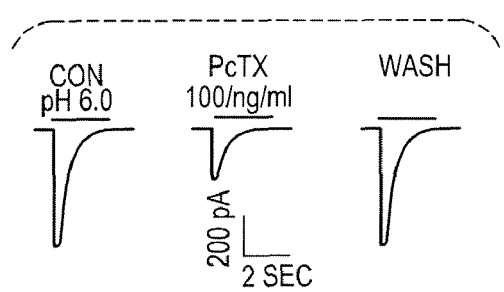
Figure 2D:
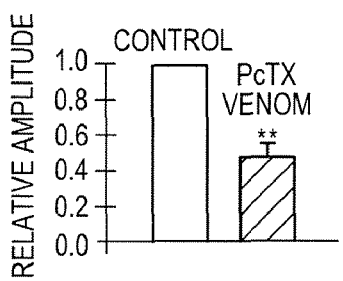

At 100 ng/mL, PcTX venom reversibly blocked the peak amplitude of ASIC current by 47%±7% (n=15, FIGS. 2C and 2D), indicating significant contributions of homomeric ASIC1a to total acid-activated currents. Increasing PcTX concentration did not induce further reduction in the amplitude of ASIC current in the majority of cortical neurons (n=8, data not shown), indicating coexistence of PcTX-insensitive ASICs (e.g., heteromeric ASIC1a/2a) in these neurons.

Example III

ASIC Response in Ischemia Model

Since acidosis may be a central feature of brain ischemia, ASIC currents were measured in neurons following 1 hr oxygen glucose deprivation (OGD), a common model of in vitro ischemia (Goldberg and Choi, 1993).

Control cultures of neurons were subjected to washes with glucose containing ECF and incubation in a conventional cell culture incubator. Test neurons were washed three times and incubated with glucose-free ECF at pH 7.4 or 6.0 in an anaerobic chamber (Model 1025, Forma Scientific) with an atmosphere of 85% $N_2$, 10% $H_2$, and 5% CO, at 35° C. Oxygen-glucose deprivation (OGD) was terminated after 1 hr by replacing the glucose-free ECF with Neurobasal medium and incubating the cultures in a normal cell culture incubator. With HEPES-buffered ECF used, 1 hr OGD slightly reduced pH from 7.38 to 7.28 (n=3) and from 6.0 to 5.96 (n=4).

ASIC current was then recorded 1 hr following the oxygen-glucose deprivation when there was no morphological alteration of neurons. ASIC currents were recorded with whole-cell patch-clamp and fast-perfusion techniques. The normal extracellular solution (ECF) contained (in mM) 140 NaCl, 5.4 KCl, 25 HEPES, 20 glucose, 1.3 $CaCl_2$, 1.0 $MgCl_2$, 0.0005 TTX (pH 7.4), 320-335 mOsm. For low pH solutions, various amounts of HCl were added. For solutions with pH<6.0, MES instead of HEPES was used for more reliable pH buffering. Patch electrodes contained (in mM) 140 CsF, 2.0 $MgCl_2$, 1.0 $CaCl_2$, 10 HEPES, 11 EGTA, 4 MgATP (pH 7.3), 300 mOsm. The $Na^+$-free solution consisted of 10 mM $CaCl_2$, 25 mM HEPES with equiosmotic NMDG or sucrose substituting for NaCl (Chu et al., 2002). A multi-barrel perfusion system (SF-77B, Warner Instrument Co.) was employed for rapid exchange of solutions.

Figure 3A:
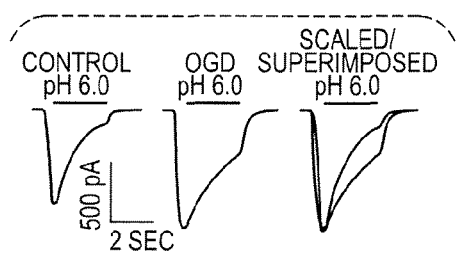
FIGS. 3 A-D are a series of graphs showing (A) an increase in amplitude and a decrease in desensitization of ASIC currents following 1 hour oxygen-glucose deprivation; (B) an increase of ASIC current amplitude in oxygen glucose deprived neurons. N=40 and 44, $*p<0.05$; (C) decreased ASIC current desensitization in oxygen-glucose deprived neurons. N=6, $**p<0.01$; and (D) lack of acid-activated current at pH 6.0 in ASIC1$^{-/-}$ neurons, in control condition, and following 1 hour oxygen-glucose deprivation (n=12 and 13).
Figure 3B:
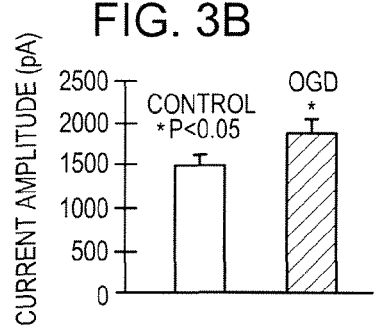
Figure 3C:
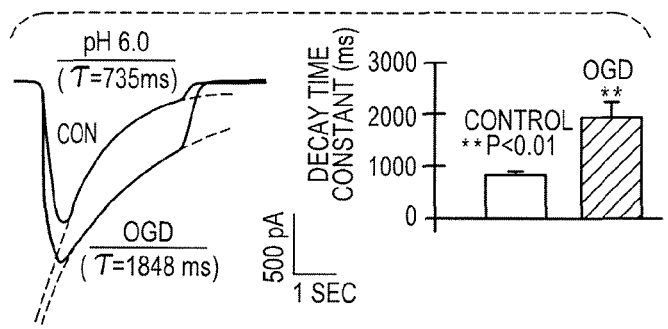
Figure 3D:
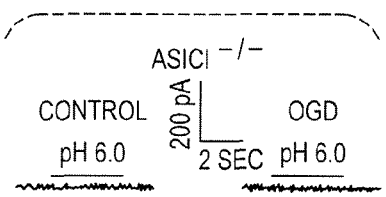

Oxygen-glucose deprivation treatment induced a moderate increase of the amplitude of ASIC currents (1520±138 pA in control group, N=44; 1886±185 pA in neurons following 1 hr oxygen-glucose deprivation, N=40, p<0.05, FIGS. 3A and 3B). More importantly, oxygen-glucose deprivation induced a dramatic decrease in ASIC desensitization as demonstrated by an increase in time constant of the current decay (814.7±58.9 ms in control neurons, N=6; 1928.9±315.7 ms in neurons following oxygen-glucose deprivation, N=6, p<0.01, FIGS. 3A and 3C). In cortical neurons cultured from ASIC1 mice, reduction of pH from 7.4 to 6.0 did not activate any inward current (n=52), similar to a previous study in hippocampal neurons (Wemmie et al., 2002). In these neurons, 1 hr oxygen-glucose deprivation did not activate or potentiate acid-induced responses (FIG. 3D, n=12 and 13).

Example IV

Permeability of ASIC to $Ca^{2+}$

Using a standard ion-substitution protocol (Jia et al., 1996) and the Fura-2 fluorescent $Ca^{2+}$-imaging technique (Chu et al., 2002), it was determined whether ASICs in cortical neurons are $Ca^{2+}$ permeable.

Cortical neurons grown on 25×25 mm glass coverslips were washed three times with ECF and incubated with 5 µM fura-2-acetoxymethyl ester for 40 min at 22° C., washed three times, and incubated in normal ECF for 30 min. Coverslips were transferred to a perfusion chamber on an inverted microscope (Nikon TE300). Cells were illuminated using a xenon lamp and observed with a 40×UV fluor oil-immersion objective lens, and video images were obtained using a cooled CCD camera (Sensys KAF 1401, Photometrics). Digitized images were acquired and analyzed in a PC controlled by Axon Imaging Workbench software (Axon Instruments). The shutter and filter wheel (Lambda $10^{-2}$) were controlled by the software to allow timed illumination of cells at 340 or 380 nm excitation wavelengths. Fura-2 fluorescence was detected at emission wavelength of 510 nm. Ratio images (340/380) were analyzed by averaging pixel ratio values in circumscribed regions of cells in the field of view. The values were exported to SigmaPlot for further analysis.

Figure 4A:
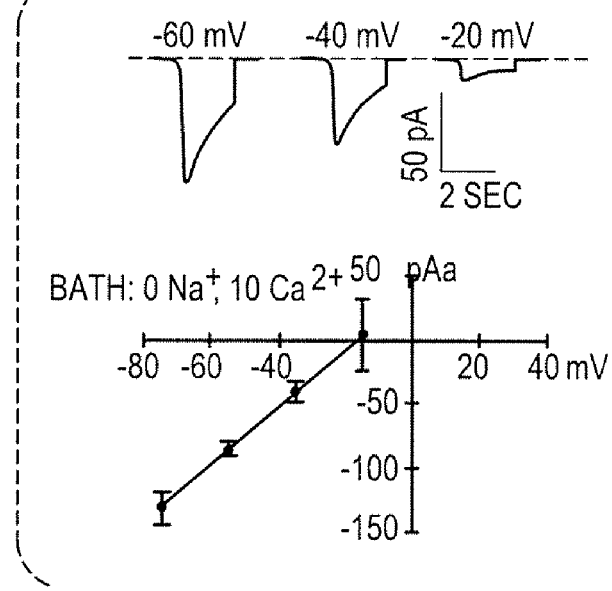
FIGS. 4 A and B are exemplary traces and summary data (A) obtained with Na$^+$-free ECF containing 10 mM Ca$^{2+}$ as the only charge carrier and (B) illustrating blockade of Ca$^{2+}$-mediated current by amiloride and PcTX venom.
Figure 4B:
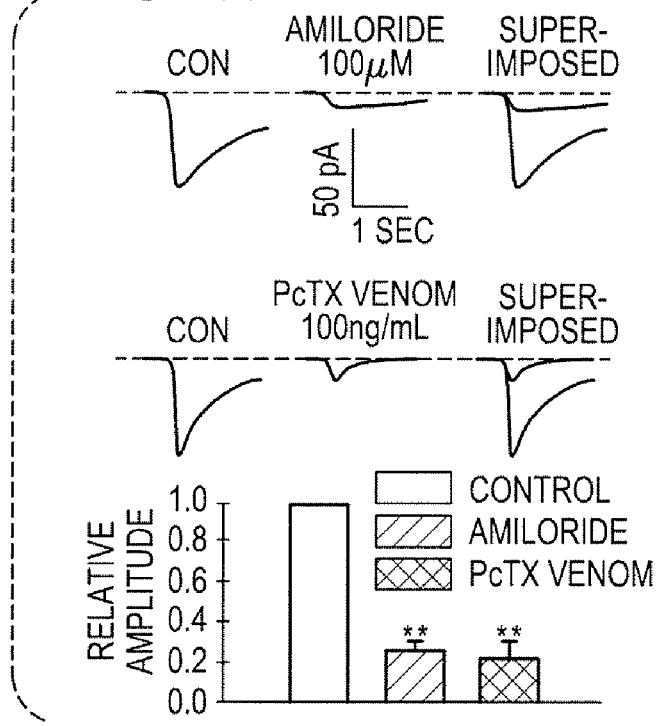

With bath solutions containing 10 mM $Ca^{2+}$ ($Na^+$ and $K^+$-free) as the only charge carrier and at a holding potential of −60 mV, inward currents larger than 50 pA in 15 out of 18 neurons were recorded at a pH of 6.0 using the whole-cell patch-clamp and fast-perfusion techniques described above, indicating significant $Ca^{2+}$ permeability of ASICs in the majority of cortical neurons (FIG. 4A). The average reversal potential was ∼−17 mV after correction of liquid junction potential (n=5). Consistent with activation of homomeric ASIC1a channels, currents carried by 10 mM $Ca^{2+}$ were largely blocked by both the nonspecific ASIC blocker amiloride and the ASIC a-specific blocker PcTX venom (FIG. 4B). The peak amplitude of $Ca^{2+}$-mediated current was decreased to 26%±2% of control by 100 µM amiloride (n=6, p<0.01) and to 22%±0.9% by 100 ng/mL PcTX venom (n=5, p<0.01).

Figure 5A:
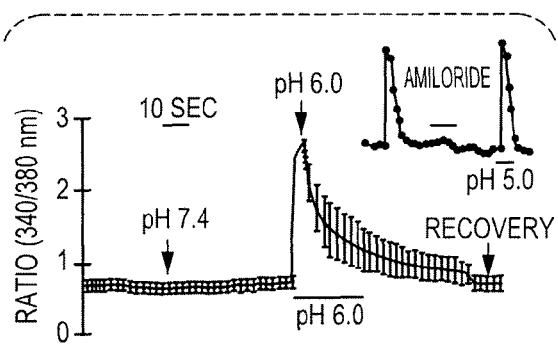
FIG. 5A-D show (A) exemplary 340/380 nm ratios as a function of pH, illustrating an increase of [Ca$^{2+}$]$_i$ by pH drop to 6.0 and (inset) exemplary inhibition of acid-induced increase of [Ca$^{2+}$]$_i$ by 100 µM amiloride; (B) summary data illustrating inhibition of acid-induced increase of [Ca$^{2+}$] by amiloride and PcTX venom. N=6-8, $**p<0.01$ compared with pH 6.0 group; (C) exemplary 340/380 nm ratios as a function of pH and NMDA presence/absence (n=8); (D) exemplary traces illustrating a lack of acid-activated current at pH 6.0 in ASIC1$^{-/-}$ neurons.

$Ca^{2+}$ imaging, in the presence of blockers of other major $Ca^{2+}$ entry pathways (MK801 10 µM and CNQX 20 µM for glutamate receptors; nimodipine 5 µM and ω-conotoxin MVIIC 1 µM for voltage-gated $Ca^{2+}$ channels), demonstrated that 18 out of 20 neurons responded to a pH drop with detectable increases in the concentration of intracellular $Ca^{2+}$ ($[Ca^{2+}]_i$) (FIG. 5A).

Figure 5B:
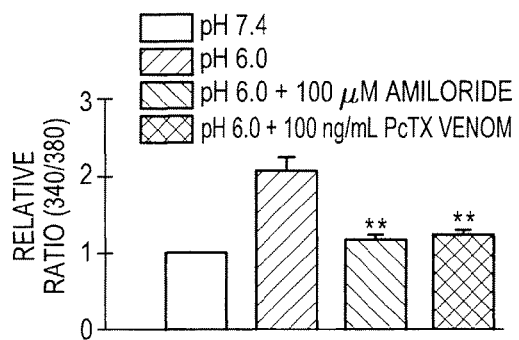
Figure 5C:
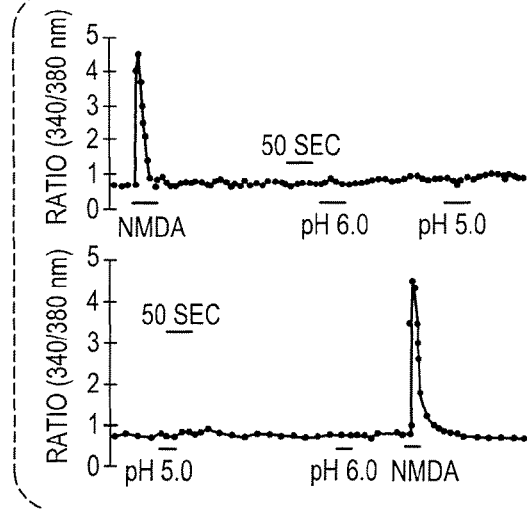
Figure 5D:
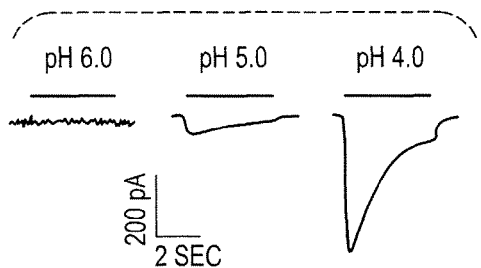

Neurons were bathed in normal ECF containing 1.3mN $CaCl_2$ with the appropriate blockers, (MK801 10 µM and CNQX 20 µM; nimodipine 5 µM and ω-conotoxin MVIIC 1 µM). In general, $[Ca^{2+}]_i$ remains elevated during prolonged perfusion of low pH solutions. In some cells, the $[Ca^{2+}]_i$ increase lasted even longer than the duration of acid perfusion (FIG. 5A). Long-lasting $Ca^{2+}$ responses suggest that ASIC response in intact neurons may be less desensitized than in whole-cell recordings or that $Ca^{2+}$ entry through ASICs may induce subsequent $Ca^{2+}$ release from intracellular stores. Preincubation of neurons with 1 µM thapsigargin partially inhibited the sustained component of $Ca^{2+}$ increase, suggesting that $Ca^{2+}$ release from intracellular stores may also contribute to acid-induced intracellular $Ca^{2+}$ accumulation (n=6, data not shown). Similar to the current carried by $Ca^{2+}$ ions (FIG. 4B), both peak and sustained increases in $[Ca^{2+}]_i$ were largely inhibited by amiloride and PcTX venom (FIGS. 5A and 5B, n=6-8 **P<0.01), consistent with involvement of homomeric ASIC1a in acid-induced $[Ca^{2+}]_i$ increase. Knockout of the ASIC1 gene eliminated the acid-induced $[Ca^{2+}]_i$ increase in all neurons without affecting NMDA receptor-mediated $Ca^{2+}$ response (FIG. 7C, n=8). Patch-clamp recordings demonstrated lack of acid-activated currents at pH 6.0 in 52 out of 52 of the ASIC1/neurons, consistent with absence of ASIC1a subunits. Lowering pH to 5.0 or 4.0, however, activated detectable current in 24 out of 52 ASIC1$^{-/-}$ neurons, indicating the presence of ASIC2a subunits in these neurons (FIG. 5D showing exemplary 340/380 nm rations as a function of pH and NMDA presence/absence). Further electrophysiological studies demonstrated that ASIC1$^{-/-}$ neurons have normal responses for various voltage-gated channels and NMDA, GABA receptor-gated channels (data not shown).

Example V

Figure 6A:
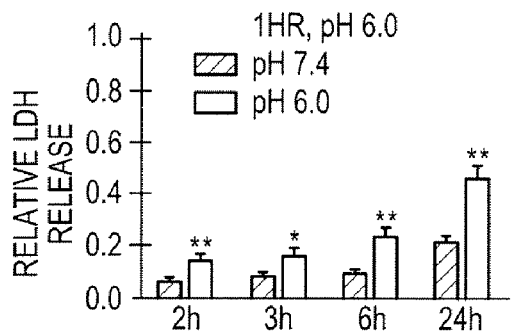
FIG. 6 A-C show graphs presenting exemplary data for time-dependent LDH release induced by (A) 1 hr or (B) 24 hr incubation of cortical neurons in pH 7.4 (solid bars) or 6.0 ECF (open bars). N=20-25 wells, $*p<0.05$, and $**p<0.01$, compared to pH 7.4 group at the same time points and inhibition of acid-induced LDH release by 100 µM amiloride or (C) 100 ng/mL PcTX venom (n=20-27, $*p<0.05$, and $**p<0.01$).
Figure 6B:
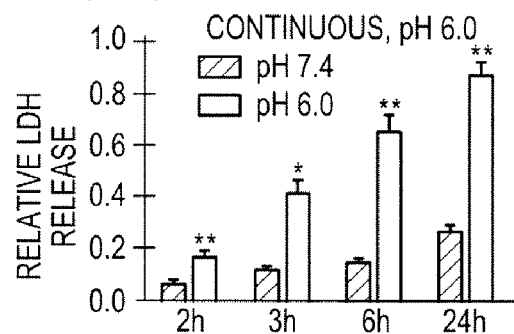

Protection Against Acidosis Induced Glutamate Independent Neuronal Injury by the ASIC Blockade Acid-induced injury was studied on neurons grown on 24-well plates incubated in either pH 7.4 or 6.0 ECF containing MK801, CNQX, and nimodipine; see FIG. 6. Cell injury was assayed by the measurement of lactate dehydrogenase (LDH) release (Koh and Choi, 1987) at various time points (FIGS. 6A and 6B, *p<0.05, **p<0.01) and by fluorescent staining of alive/dead cells.

Cells were washed three times with ECF and randomly divided into treatment groups. MK801 (10 μM), CNQX (20 μM), and nimodipine (5 μM) were added in all groups to eliminate potential secondary activation of glutamate receptors and voltage-gated $Ca^{2+}$ channels. Following acid incubation, neurons were washed and incubated in Neurobasal medium at 37° C. LDH release was measured in culture medium using the LDH assay kit (Roche Molecular Biochemicals, Indianapolis, Ind., USA). Medium (100 μL) was transferred from culture wells to 96-well plates and mixed with 100 μL reaction solution provided by the kit. Optical density was measured at 492 nm 30 min later, utilizing a microplate reader (Spectra Max Plus, Molecular Devices, Sunnyvale, Calif. USA). Background absorbance at 620 was subtracted. The maximal releasable LDH was obtained in each well by 15 min incubation with 1% Triton X-100 at the end of each experiment.

To stain the cells, cells were incubated in ECF containing fluorescein-diacetate (FDA) (5 μM) and propidium iodide (PI) (2 μM) for 30 min followed by wash with dye-free ECF. Alive (FDA-positive) and dead (PI-positive) cells were viewed and counted on a microscope (Zeiss, Thornwood, N.Y., USA) equipped with epifluorescence at 580/630 nm excitation/emission for PI and 500/550 nm for FDA. Images were collected using an Optronics DEI-730 camera equipped with a BQ 8000 sVGA frame grabber and analyzed using computer software (Bioquant, Tenn.).

Figure 34A:
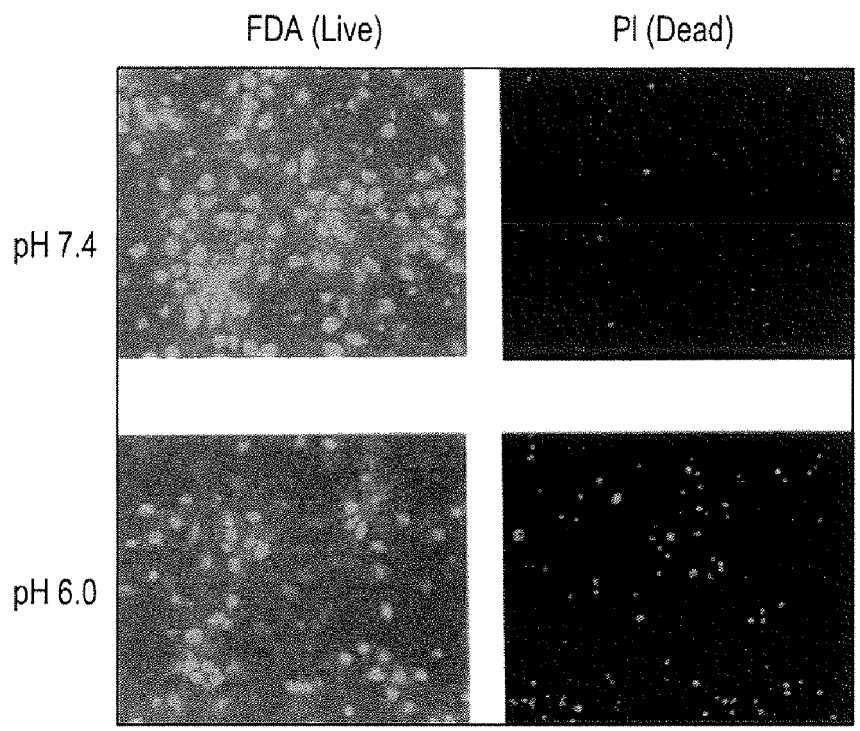
FIGS. 34 A and B are (A) representative images showing fluorescein diacetate (FDA, blue, left column) staining of alive neurons and propidium iodide (PI, red, right column) staining of the nuclei of dead neurons and (B) a graph of summary data showing data showing the acidosis-induced neuronal injury as measured by counting the percentage of FDA-positive and PI-positive cells n=3-4 coverslips. Two to three fields were counted and averaged for each coverslip; **$p<0.01$ FIGS. 35 A and B are (A) Black/white (left) and fluorescent (right) images showing Chinese Hamster Ovary (CHO) cells transfected with GFP alone at 24 hr following 1 hr incubation with either pH 7.0 (upper panel) or pH 6.0 ECF (lower panel); and (B) black/white (left) and fluorescent image (right) showing CHO cells transfected with ASIC1a/GFP at 24 hr following 1 hr incubation with either pH 7.0 (upper panel) or pH 6.0 ECF (lower panel).
Figure 34B:
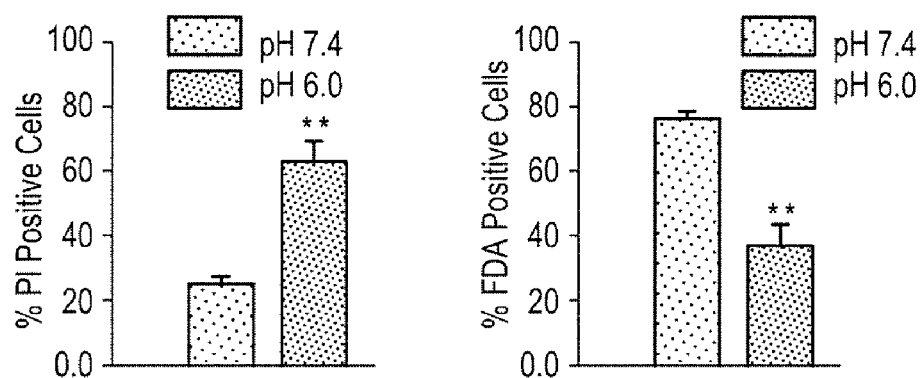

Compared to neurons treated at pH 7.4, 1 hr acid incubation (pH 6.0) induced a time-dependent increase in LDH release (FIG. 6A). After 24 hr, 45.7%±5.4% of maximal LDH release was induced (n=25 wells). Continuous treatment at pH 6.0 induced greater cell injury (FIG. 6B, n=20). Consistent with the LDH assay, alive/dead staining with fluorescein diacetate (FDA, blue) and propidium iodide (PI, red) at 24 hr following 1 hr incubation of neurons with either pH 7.4 or 6.0 ECF showed similar increases in cell death by 1 hr acid treatment (See FIG. 34). One hour incubation with pH 6.5 ECF also induced significant but less LDH release than with pH 6.0 ECF (n=8 wells).

Figure 6C:
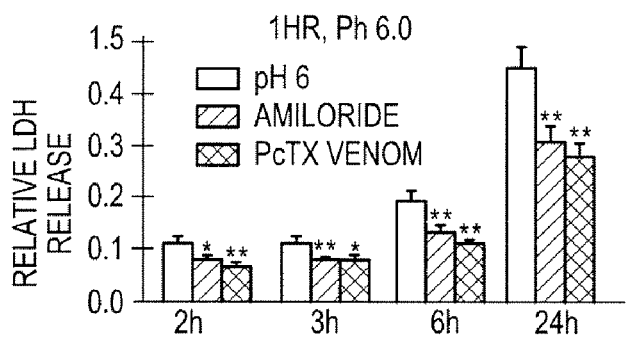

To determine whether activation of ASICs is involved in acid-induced glutamate receptor-independent neuronal injury, we tested the effect of amiloride and PcTX venom on acid-induced LDH release. Addition of either 100 μM amiloride or 100 ng/mL PcTX venom 10 min before and during the 1 hr acid incubation significantly reduced LDH release (FIG. 6C). At 24 hr, LDH release was decreased from 45.3%±3.8% to 31.1%±2.5% by amiloride and to 27.9%±2.6% by PcTX venom (n=20-27, p <0.01). Addition of amiloride or PcTX venom in pH 7.4 ECF for 1 hr did not affect baseline LDH release, although prolonged incubation (e.g., 5 hr) with amiloride alone increased LDH release (n=8).

Example VI

Transfection of COS-7 Cells

COS-7 cells, a cell line commonly used for expression of ASICs due to its lack of endogenous channels (Chen et al. 1998; Immke and McCleskey 2001 and Escoubas et al. 2000), were cultured in MEM with 10% HS and 1% PenStrep (GIBCO). At ~50% confluence, cells were cotransfected with cDNAs for ASICs and GFP in pcDNA3 vector using FuGENE6 transfection reagents (Roche Molecular Biochemicals). DNA for ASICs (0.75 μg) and 0.25 μg of DNA for GFP were used for each 35 mm dish. GFP-positive cells were selected for patch-clamp recording 48 hr after transfection. For stable transfection of ASIC1a, 500 μg/mL G418 was added to culture medium 1 week following the transfection. The surviving G418-resistant cells were further plated and passed for >5 passages in the presence of G418. Cells were then checked with patch-clamp and immunofluorescent staining for the expression of ASIC1a.

Example VII

Role of Calcium Entry in Acid-Induced Injury

To determine whether $Ca^{2+}$ entry plays a role in acid-induced injury, neurons were treated with pH 6.0 ECF in the presence of normal or reduced $[Ca^{2+}]_e$; see FIG. 7.

Cell injury was determined by LDH measurement. Cells were washed three times with ECF and randomly divided into treatment groups. MK801 (10 μM), CNQX (20 μM), and nimodipine (5 μM) were added in all groups to eliminate potential secondary activation of glutamate receptors and voltage-gated $Ca^{2+}$ channels. Following acid incubation, neurons were washed and incubated in Neurobasal medium at 37° C. LDH release was measured in culture medium using the LDH assay kit (Roche Molecular Biochemicals, Indianapolis, 1N, USA). Medium (100 μL) was transferred from culture wells to 96-well plates and mixed with 100 μL reaction solution provided by the kit. Optical density was measured at 492 nm 30 min later, utilizing a microplate reader (Spectra Max Plus, Molecular Devices, Sunnyvale, Calif. USA). Background absorbance at 620 was subtracted. The maximal releasable LDH was obtained in each well by 15 min incubation with 1% Triton X-100 at the end of each experiment.

As shown in FIG. 7A, reducing $Ca^{2+}$ from 1.3 to 0.2 mM inhibited acid-induced LDH release (from 40.0%±4.1% to 21.9%±2.5%), as did ASIC1a blockade with PcTX venom (n=11-12, p<0.01; FIG. 7A). $Ca^{2+}$-free solution was not tested, as a complete removal of $[Ca^{2+}]_e$ may activate large inward currents through a $Ca^{2+}$-sensing cation channel, which may otherwise complicate data interpretation (Xiong et al., 1997). Inhibition of acid injury by both amiloride and PcTX, nonspecific and specific ASIC1a blockers, and by reducing $[Ca^{2+}]_c$ suggests that activation of $Ca^{2+}$-permeable ASIC1a may be involved in acid-induced neuronal injury.

Example VIII

Effect of Activation of ASIC1a Cells in Acid Injury

To provide additional evidence that activation of ASIC1a is involved in acid injury, acid injury of nontransfected and ASIC1a transfected COS-7 cells as described above was studied. Following confluence (36-48 hr after plating), cells were treated with either pH 7.4 or 6.0 ECF for 1 hr.

LDH release was measured 24 hr after acid incubation. Cells were washed three times with ECF and randomly divided into treatment groups. LDH release was measured in culture medium using the LDH assay kit (Roche Molecular Biochemicals). Medium (100 µL) was transferred from culture wells to 96-well plates and mixed with 100 µL reaction solution provided by the kit. Optical density was measured at 492 nm 30 min later, utilizing a microplate reader (Spectra Max Plus, Molecular Devices). Background absorbance at 620 was subtracted. The maximal releasable LDH was obtained in each well by 15 min incubation with 1% Triton X-100 at the end of each experiment.

Treatment of nontransfected COS-7 cells with pH 6.0 ECF did not induce increased LDH release when compared with pH 7.4-treated cells (10.3%±0.8% for pH 7.4, and 9.4%±0.7% for pH 6.0, N=19 and 20 wells; p>0.05, FIG. 7B). However, in COS-7 cells stably transfected with ASIC1a, 1 hr incubation at pH 6.0 significantly increased LDH release from 15.5%±2.4% to 24.0%±2.9% (n=8 wells, p<0.05). Addition of amiloride (100 µM) inhibited acid-induced LDH release in these cells (FIG. 7B). (*p<0.05 for 7.4 versus 6.0 and 6.0 versus 6.0+amiloride)

Example IX

Acid Injury in CHO Cells

We also studied acid injury of Chinese Hamster ovary (CHO) cells transiently transfected with cDNAs encoding GFP alone or GFP plus ASIC1a. After the transfection (24-36 hr), cells were incubated with either a solution at pH 7.0 or an acidic solution (pH 6.0 ECF) for 1 hr, and cell injury was assayed 24 hr following the acid incubation by counting relative number of surviving GFP-positive cells. Since dying cells gradually lose their green fluorescence, the relative number of remaining GFP-positive cells can be used as an estimation of cell injury.

Figure 35A:
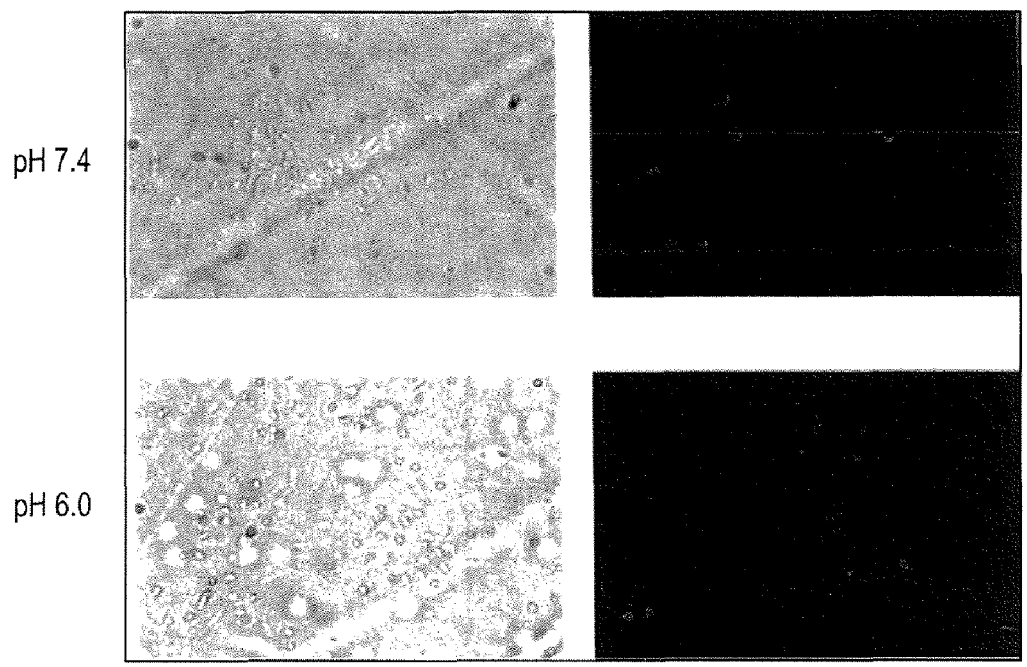
Figure 35B:
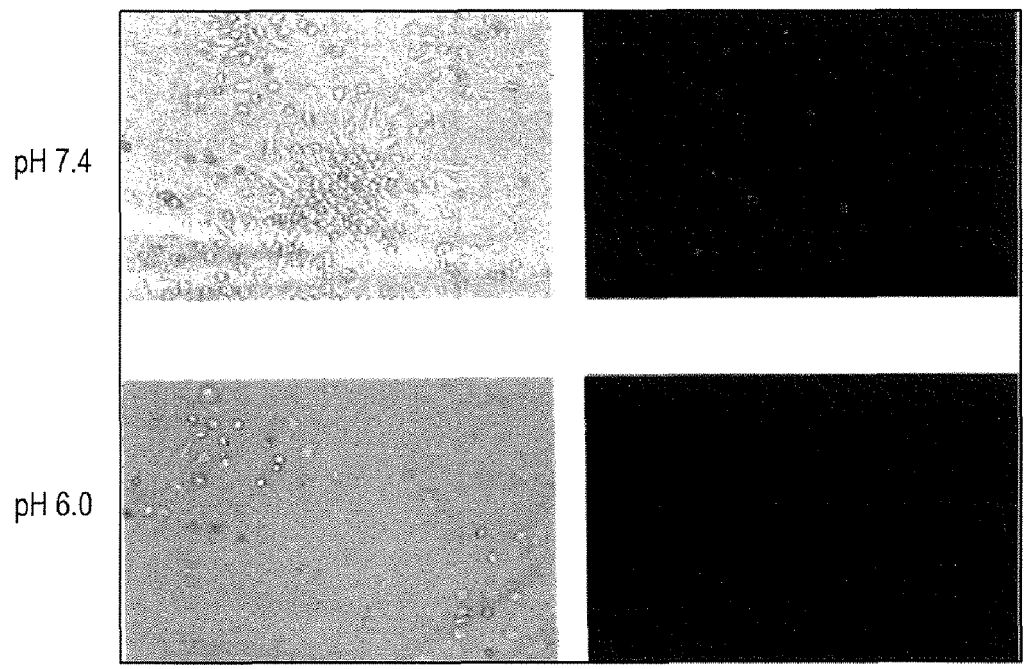

As shown in FIG. 35, in the comparison of CHO cells incubated with a neutral solution (FIG. 35, upper panels in A and B) and CHO cells after 1 hr acid incubation (FIG. 35, lower panels in A and B), the acid treatment largely reduced surviving GFP-positive cells in GFP/ASIC1a group but not in the group transfected with GFP alone (n=3 dishes in each group).

Example X

Cell Toxicity Experiments

To further demonstrate an involvement of ASIC1a in acidosis-induced neuronal injury, cell toxicity experiments were performed on cortical neurons cultured from $ASIC^{+/+}$ and $ASIC1^{-/-}$ mice (Wemmie et al., 2002). Following anesthesia with halothane, cerebral cortices were dissected from PI $ASIC1^{+/+}$ and $ASIC1^{-/-}$ mice and incubated with 0.05% trypsin-EDTA for 10 min at 37° C. Tissues were then triturated with fire-polished glass pipettes and plated on poly-L-ornithine-coated 24-well plates or 25×25 mm glass coverslips at a density of 2.5×10$^5$ cells per well or 10$^6$ cells per coverslip. Neurons were cultured with MEM supplemented with 10% horse serum (for E16 cultures) or Neurobasal medium supplemented with B27 (for P1 cultures) and used for electrophysiology and toxicity studies after 12 days. Glial growth was suppressed by addition of 5-fluoro-2-deoxyuridine and uridine, yielding cultured cells with ~90% neurons as determined by NeuN and GFAP staining (data not shown).

Cells were treated with either pH 7.4 or 6.0 ECF for 1 hr. LDH release was measured 24 hr after acid incubation. Cells were washed three times with ECF and randomly divided into treatment groups. LDH release was measured in culture medium using the LDH assay kit (Roche Molecular Biochemicals). Medium (100 µL) was transferred from culture wells to 96-well plates and mixed with 100 µL reaction solution provided by the kit. Optical density was measured at 492 nm 30 min later, utilizing a microplate reader (Spectra Max Plus, Molecular Devices). Background absorbance at 620 was subtracted. The maximal releasable LDH was obtained in each well by 15 min incubation with 1% Triton X-100 at the end of each experiment.

Again, 1 hr acid incubation of $ASIC^{+/+}$ neurons at 6.0 induced substantial LDH release that was reduced by amiloride and PcTX venom (n=8-12). One hour acid treatment of $ASIC1^{-/-}$ neurons, however, did not induce significant increase in LDH release at 24 hr (13.8%±0.9% for pH 7.4 and 14.2%±1.3% for pH 6.0, N=8, p>0.05), indicating resistance of these neurons to acid injury (FIG. 7C). In addition, knockout of the ASIC1 gene also eliminated the effect of amiloride and PcTX venom on acid-induced LDH release (FIG. 7C, n=8 each), further suggesting that the inhibition of acid-induced injury of cortical neurons by amiloride and PcTX venom (FIG. 6C) was due to blockade of ASIC1 subunits. In contrast to acid incubation, 1 hr treatment of $ASIC1^{-/-}$ neurons with 1 mM NMDA+10 µM glycine (in $Mg^{2+}$-free [pH 7.4] ECF) induced 84.8%±1.4% of maximal LDH release at 24 hr (n=4, FIG. 7C), indicating normal response to other cell injury processes.

Example XI

Effect of Oxygen Glucose Deprivation and Acidosis on Neuronal Injury

To determine if activation of ASICs in ischemic conditions produced greater neuronal injury, neurons from P1 $ASIC1^{+/+}$ and $ASIC1^{-/-}$ mice were subjected to 1 hr acid treatment under oxygen and glucose deprivation.

Following anesthesia with halothane, cerebral cortices were dissected from PI $ASIC1^{+/+}$ and $ASIC1^{-/-}$ mice and incubated with 0.05% trypsin-EDTA for 10 min at 37° C. Tissues were then triturated with fire-polished glass pipettes and plated on poly-L-ornithine-coated 24-well plates or 25×25 mm glass coverslips at a density of 2.5×10$^5$ cells per well or 10$^6$ cells per coverslip. Neurons were cultured with MEM supplemented with 10% horse serum (for E16 cultures) or Neurobasal medium supplemented with B27 (for P1 cultures) and used for electrophysiology and toxicity studies after 12 days. Glial growth was suppressed by addition of 5-fluoro-2-deoxyuridine and uridine, yielding cultured cells with ~90% neurons as determined by NeuN and GFAP staining (data not shown).

Neurons were then washed three times and incubated with glucose-free ECF at pH 7.4 or 6.0 in an anaerobic chamber (Model 1025, Form a Scientific) with an atmosphere of 85%

$N_2$, 10% $H_2$, and 5% $CO_2$ at 35° C. MK801, CNQX, and nimodipine were added to all solutions to inhibit voltage-gated $Ca^{2+}$ channels and glutamate receptor-mediated cell injury associated with oxygen-glucose deprivation (Kaku et al., 1991). Oxygen-glucose deprivation was terminated after 1 hr by replacing the glucose-free ECF with Neurobasal medium and incubating the cultures in a normal cell culture incubator.

One hour incubation with pH 7.4 ECF under oxygen-glucose deprivation conditions induced only 27.1%±3.5% of maximal LDH release at 24 hr (n=5, FIG. 7D). This finding is in agreement with a previous report that 1 hr oxygen-glucose deprivation does not induce substantial cell injury with the blockade of glutamate receptors and voltage-gated $Ca^{2+}$ channels (Aarts et al., 2003). However, 1 hr oxygen-glucose deprivation, combined with acidosis (pH 6.0), induced 73.9%±4.3% of maximal LDH release (n=5, FIG. 7D, p<0.01), significantly larger than acid-induced LDH release in the absence of oxygen-glucose deprivation (see FIG. 8A, p<0.05).

In contrast, 1 hr treatment with combined oxygen-glucose deprivation and acid only slightly increased LDH release in ASIC1$^{-/-}$ neurons (from 26.1%±2.7% to 30.4%±3.5%, N=10-12, FIG. 7D). This finding suggests that potentiation of acid-induced injury by oxygen-glucose deprivation may be due largely to oxygen-glucose deprivation potentiation of ASIC1-mediated toxicity.

Addition of the ASIC1a blocker PcTX venom (100 ng/mL) significantly reduced acid/oxygen-glucose deprivation-induced LDH release to 44.3%±5.3% (n=5, p<0.05, FIG. 7D).

Example XII

Mechanism of Neuronal Injury in Oxygen-Glucose Deprivation and Acidosis Model

Aarts et al. (2003) have recently studied ischemia molded by prolonged oxygen-glucose deprivation (2 hr) but without acidosis. In this model system, they demonstrated activation of a $Ca^{2+}$-permeable nonselective cation conductance activated by reactive oxygen/nitrogen species resulting in glutamate receptor-independent neuronal injury. The prolonged oxygen-glucose deprivation-induced cell injury modeled by Aarts et al. may be reduced dramatically by agents either scavenging free radicals directly (e.g., trolox) or reducing the production of free radicals (e.g., L-NAME) (Aarts et al., 2003). To determine whether combined short duration oxygen-glucose deprivation and acidosis induced neuronal injury may involve a similar mechanism, we tested the effect of trolox and L-NAME on oxygen-glucose deprivation/acid-induced LDH release.

Following anesthesia with halothane, cerebral cortices were dissected from P1 ASIC1$^{+/+}$ and ASIC1$^{-/-}$ mice and incubated with 0.05% trypsin-EDTA for 10 min at 37° C. Tissues were then triturated with fire-polished glass pipettes and plated on poly-L-ornithine-coated 24-well plates or 25×25 mm glass coverslips at a density of 2.5×10$^5$ cells per well or 10$^6$ cells per coverslip. Neurons were cultured with MEM supplemented with 10% horse serum (for E16 cultures) or Neurobasal medium supplemented with B27 (for P1 cultures) and used for electrophysiology and toxicity studies after 12 days. Glial growth was suppressed by addition of 5-fluoro-2-deoxyuridine and uridine, yielding cultured cells with ~90% neurons as determined by NeuN and GFAP staining (data not shown).

Neurons were then washed three times and incubated with glucose-free ECF at pH 7.4 or 6.0 in an anaerobic chamber (Model 1025, Form a Scientific) with an atmosphere of 85% $N_2$, 10% $H_2$, and 5% $CO_2$ at 35° C. MK801, CNQX, and nimodipine were added to all solutions to inhibit voltage-gated $Ca^{2+}$ channels and glutamate receptor-mediated cell injury associated with oxygen-glucose deprivation (Kaku et al., 1991). Oxygen-glucose deprivation was terminated after 1 hr by replacing the glucose-free ECF with Neurobasal medium and incubating the cultures in a normal cell culture incubator As shown in FIG. 9D, neither trolox (500 μM) nor L-NAME (300 μM) had significant effect on combined 1 hr oxygen-glucose deprivation/acidosis-induced neuronal injury (n=8-11). Additionally, as can be seen in FIG. 36, the ASIC blockers amiloride and PcTX venom had no effect on the conductance of TRPM7 channels reported to be responsible for prolonged oxygen-glucose deprivation-induced neuronal injury by Aarts et al. (2003). In FIG. 36, after a stable current-voltage relationship (I-V curve) was recorded, amiloride at either 100 μM or 500 μM was perfused to the cell for ~10 min. The I-V curve in the presence of amilolide was then generated (FIG. 36 A). Similarly in FIG. 36B, after a stable I-V curve was recorded, PcTX venom at 300 ng/ml was perfused to the cell for ~10 min. The I-V curve in the presence of PcTX venom was then generated.

Together, these findings strongly suggest that activation of ASICs but not TRPM7 channels may be largely responsible for combined 1 hr oxygen-glucose deprivation/acidosis-induced neuronal injury in our studies.

Example XIII

Effect of PcTX in Animal Model of Focal Ischemia

To provide evidence that activation of ASIC1a may be involved in ischemic brain injury in vivo, the protective effect of amiloride and PcTX venom in a rat model of transient focal ischemia (Longa et al., 1989) was tested.

A total of 6 μL artificial cerebrospinal fluid (aCSF) alone, aCSF-containing amiloride (1 mM), or PcTX venom (500 ng/mL) was injected intracerebroventricularly 30 min before and after the ischemia. Transient focal ischemia was induced for 100 minutes by suture occlusion of the middle cerebral artery (middle cerebral artery occlusion) in male rats (SD, 250-300 g) and mice (with congenic C57B16 background, ~25 g) anesthetized using 1.5% isoflurane, 70% $N_2O$, and 28.5% $O_2$ with intubation and ventilation. Rectal and temporalis muscle temperature was maintained at 37° C.±0.5° C. with a thermostatically controlled heating pad and lamp. Cerebral blood flow was monitored by transcranical LASER doppler. Animals with blood flow not reduced below 20% were excluded.

Animals were killed with chloral hydrate 24 hr after ischemia. Brains were rapidly removed, sectioned coronally at r 2 mm (rats) intervals, and stained by immersion in vital dye (2%) 2,3,5-triphenyltetrazolium hydrochloride (TTC). Infarction area was calculated by subtracting the normal area stained with TTC in the ischemic hemisphere from the area of the nonischemic hemisphere. Infarct volume was calculated by summing infarction areas of all sections and multiplying by slice thickness. Rat intraventricular injection was performed by stereotaxic technique using a microsyringe pump with cannula inserted stereotactically at 0.8 mm posterior to bregma, 1.5 mm lateral to midline, and 3.8 mm ventral to the dura. All manipulations and analyses were performed by individuals blinded to treatment groups.

Based on the study by Westergaard (1969), the volume for cerebral ventricular and spinal cord fluid for 4-week-old rats is estimated to be ~60 μL. Assuming that the infused amiloride and PcTX were uniformly distributed in the CSF, a concentration of ~100 μM for amiloride and ~50 ng/mL for PcTX was expected and found in the cell culture experiments. Infarct volume was determined by TTC staining (Bederson et al., 1986) at 24 hr following ischemia.

Figure 8A:
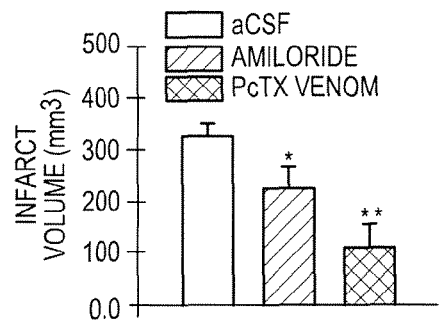
FIG. 8 A-D shows a series of graphs depicting infarct volume in TTC-stained brain sections in (A) rats injected with artificial cerebrospinal fluid (aCSF) (n=7), amiloride (n=11), or PcTX venom (n=5) 30 minutes before and after induction of 100 minutes of transient middle cerebral artery occlusion. $*p<0.05$ and $**p<0.01$ compared with aCSF injected group; (B) male ASIC1$^{+/+}$, ASIC1$^{+/-}$, and ASIC1$^{-/-}$ mice subjected to 60 minutes of mid-cerebral artery occlusion (n=6 for each group). $*p<0.05$ and $p<0.01$ compared with +/+ group; (C) C57Bl/6 mice intraperitoneally injected with 10 mg/kg memantine (Mem) or intraperitoneal injection of memantine accompanied by intracerebroventricularly injection of PcTX venom (500 ng/mL). $p<0.01$ compared with aCSF injection and between memantine and memantine plus PcTX venom (n=5 in each group); (D) male ASIC1$^{+/+}$ (wt) and ASIC1$^{-/-}$ mice subjected to 60 minutes of mid-cerebral artery occlusion and intraperitoneally injected with memantine (n=5 in each group). $*p<0.05$, and $**p<0.01$.

Ischemia (100 min) produced an infarct volume of 329.5±25.6 mm$^3$ in aCSF-injected rats (n=7) but only 229.7±41.1 mm$^3$ in amiloride-injected (n=11, *p<0.05) and 130.4±55.0 mm$^3$ (60% reduction) in PcTX venom-injected rats (n=5, **p<0.01) (FIG. 8A).

Example XIV

Involvement of ASIC1a in Ischemic Brain Injury

ASIC1$^{-/-}$ mice were used to further demonstrate the involvement of ASIC1a in ischemic brain injury in vivo. Male ASIC1$^{+/+}$, ASIC1H$^{+/-}$, and ASIC1$^{-/-}$ mice (~25 g, with congenic C57B16 background) were subjected to 60 min middle cerebral artery occlusion as previously described (Stenzel-Poore et al., 2003).

Animals were killed with chloral hydrate 24 hr after ischemia. Brains were rapidly removed, sectioned coronally at 1 mm (mice) intervals, and stained by immersion in vital dye (2%) 2,3,5-triphenyltetrazolium hydrochloride (TTC). Infarction area was calculated by subtracting the normal area stained with TTC in the ischemic hemisphere from the area of the nonischemic hemisphere. Infarct volume was calculated by summing infarction areas of all sections and multiplying by slice thickness. All manipulations and analyses were performed by individuals blinded to treatment groups.

Figure 8B:
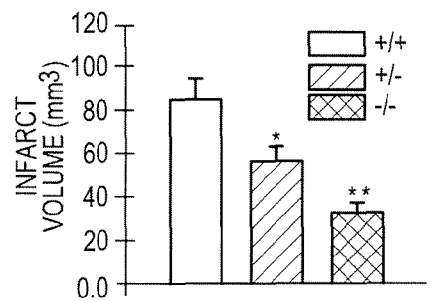

Consistent with the protection by pharmacological blockade of ASIC1a (above), −/− mice displayed significantly smaller (~61% reduction) infarct volumes (32.9±4.7 mm$^3$, N=6) as compared to +/+ mice (84.6±10.6 mm$^3$, N=6, **p<0.01). +/−mice also showed reduced infarct volume (56.9±6.7 mm$^3$, N=6, *p<0.05) (FIG. 8B).

Example XV

Protective Effect of Blockade or Absence of ASIC1a in a Glutamate Cascade

In order to determine whether blockade of ASIC1a channels or knockout of the ASIC1 gene could provide additional protection in vivo in the setting of a glutamate cascade.

The uncompetitive NMDA receptor antagonist memantine was selected, as it has been recently used in successful clinical trials (Tariot et al., 2004). Memantine (10 mg/kg) was injected intraperitoneally (intraperitoneal) into Male ASIC1$^{+/+}$, ASIC1$^{+/-}$, and ASIC1$^{-/-}$ mice (~25 g, with congenic C57B16 background) immediately following 60 min middle cerebral artery occlusion as previously described (Stenzel-Poore et al., 2003) and accompanied by intracerebroventricular injection (intracerebroventricularly) of a total volume of 0.4 μL aCSF alone or aCSF containing PcTX venom (500 ng/mL) 15 min before and following ischemia.

Figure 8C:
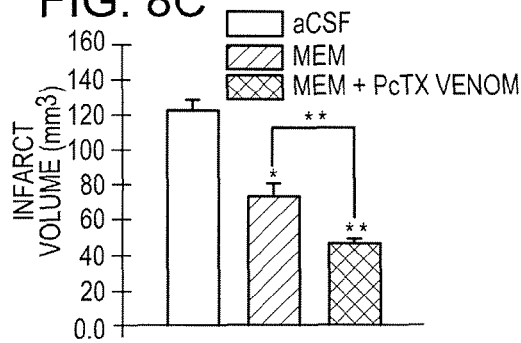
Figure 8D:
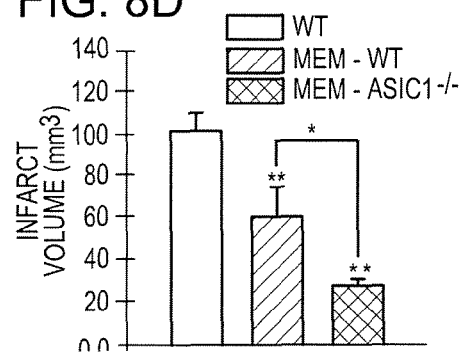

In control mice with intraperitoneal injection of saline and intracerebroventricularly injection of aCSF, 60 min middle cerebral artery occlusion induced an infarct volume of 123.6±5.3 mm$^3$ (n=5, FIG. 8C). In mice with intraperitoneal injection of memantine and intracerebroventricularly injection of aCSF, the same duration of ischemia induced an infarct volume of 73.8±6.9 mm$^3$ (n=5, p<0.01). However, in mice injected with memantine and PcTX venom, an infarct volume of only 47.0±1.1 mm$^3$ was induced (n=5, p<0.01 compared with both control and memantine groups, FIG. 8C). These data suggest that blockade of homomeric ASIC1a may provide additional protection in in vivo ischemia in the setting of NMDA receptor blockade. Additional protection was also observed in ASIC1$^{-/-}$ mice treated with pharmacologic NMDA blockade (FIG. 8D). In ASIC$^{+/+}$ mice intraperitoneal injected with saline or 10 mg/kg memantine, 60 min middle cerebral artery occlusion induced an infarct volume of 101.4±9.4 mm$^3$ or 61.6±12.7 mm$^3$, respectively (n=5 in each group, FIG. 8D). However, in ASIC1$^{-/-}$ mice injected with memantine, the same ischemia duration induced an infarct volume of 27.7±1.6 mm$^3$ (n=5), significantly smaller than the infarct volume in ASIC1$^{+/+}$ mice injected with memantine (p<0.05).

Example XVI

Time Window of PcTX Neuroprotection

Figure 9:
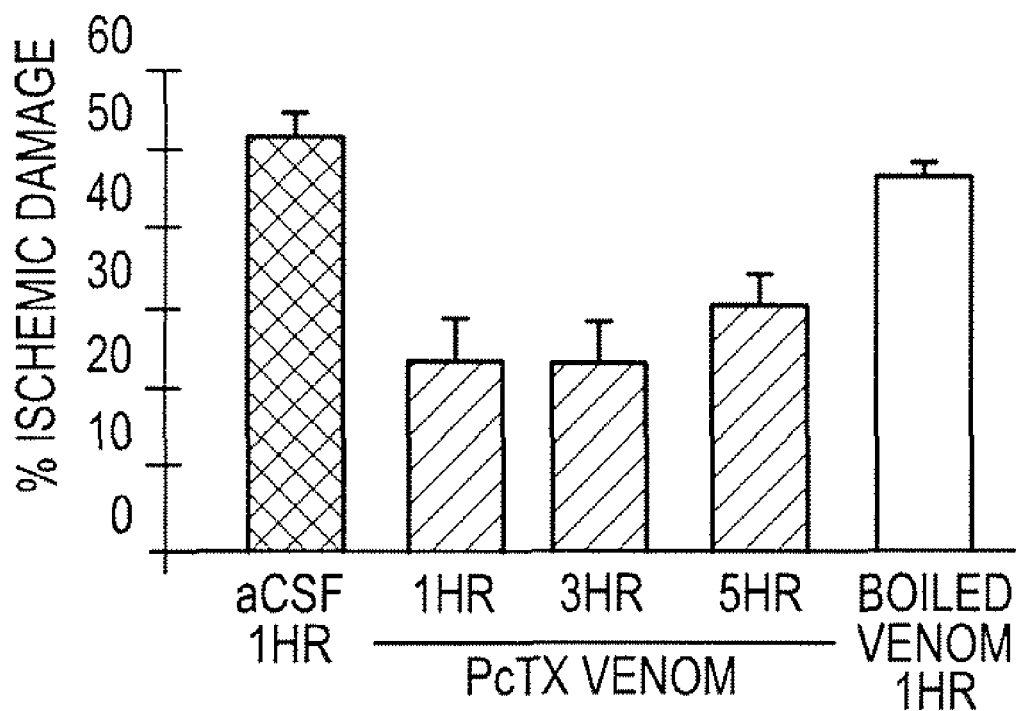
FIG. 9 is a graph showing the neuroprotective effect of infusion into the lateral ventricles of each rodent of 0.5 µL, 500 ng/mL PcTX venom at 1, 3 and 5 hours after a middle cerebral artery occlusion in comparison to infusion of aCSF and boiled venom.

This example describes exemplary experiments that measure the neuroprotective effect of PcTX venom at different times after onset of stroke in rodents; see FIG. 9. Brain ischemia (stroke) was induced in rodents by mid-cerebral artery occlusion (middle cerebral artery occlusion). Transient focal ischemia was induced for 100 minutes by suture occlusion of the middle cerebral artery (middle cerebral artery occlusion) in male rats (SD, 250-300 g) and mice (with congenic C57B16 background, ~25 g) anesthetized using 1.5% isoflurane, 70% N$_2$O, and 28.5% O$_2$ with intubation and ventilation. Rectal and temporalis muscle temperature was maintained at 37° C.±0.5° C. with a thermostatically controlled heating pad and lamp. Cerebral blood flow was monitored by transcranical LASER doppler. Animals with blood flow not reduced below 20% were excluded. At 1, 3, and 5 hours after induction, artificial cerebrospinal fluid (aCSF), PcTX venom (0.5 μL, 500 ng/mL total protein), or inactivated (boiled) venom was infused into the lateral ventricles of each rodent.

Animals were killed with chloral hydrate 24 hr after ischemia. Brains were rapidly removed, sectioned coronally at 1 mm (mice) or 2 mm (rats) intervals, and stained by immersion in vital dye (2%) 2,3,5-triphenyltetrazolium hydrochloride (TTC). Infarction area was calculated by subtracting the normal area stained with TTC in the ischemic hemisphere from the area of the nonischemic hemisphere. Infarct volume was calculated by summing infarction areas of all sections and multiplying by slice thickness. Rat intraventricular injection was performed by stereotaxic technique using a microsyringe pump with cannula inserted stereotactically at 0.8 mm posterior to bregma, 1.5 mm lateral to midline, and 3.8 mm ventral to the dura. All manipulations and analyses were performed by individuals blinded to treatment groups.

Administration of PcTX venom provided a 60% reduction in stroke volume both at one hour and at three hours after stroke onset. Furthermore, substantial stroke volume reduction still may be maintained if treatment is withheld for five hours after the onset of the middle cerebral artery occlusion. Accordingly, neuroprotection due to ASIC inhibition may have an extended therapeutic time window after stroke onset, allowing stroke subjects to benefit from treatment performed hours after the stroke began. This effect of ASIC blockade on stroke neuroprotection is far more robust than that of calcium channel blockade of the NMDA receptor (a major target for experimental stroke therapeutics) using a glutamate antagonist. No glutamate antagonist, thus far, has such a favorable profile as shown here for ASIC1a-selective inhibition.

Example XVII

Selectivity of PcTX Venom for ASIC1a

Figure 12:
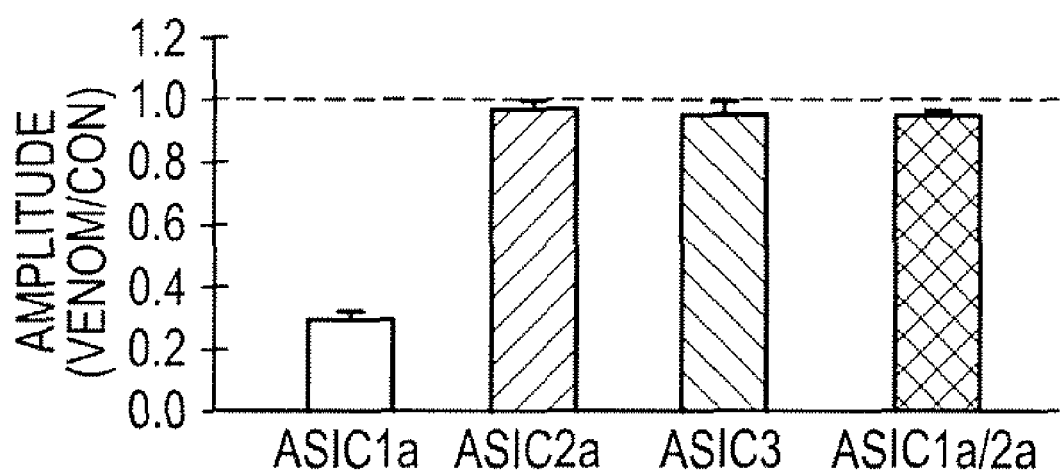
FIG. 12 is a graph showing the amplitude of the current in COS-7 cells expressing the indicated ASIC proteins and treated with PcTX venom (25 ng/mL on ASIC1a expressing cells and 500 ng/mL on ASIC2a, ASIC3 or ASIC1a+2a expressing cells).

This example describes experiments that measure the selectivity of PcTX venom (and thus PcTx1 toxin) for ASIC1a alone, relative to other ASIC proteins or combinations of ASIC proteins expressed in cultured cells as well as other voltage and ligand gated channels; see FIG. 12. COS-7 cells expressing the indicated ASIC proteins prepared as in Example VI were treated with PcTX venom (25 ng/mL on ASIC1a expressing cells and 500 ng/mL on ASIC2a, ASIC3 or ASIC1a+2a expressing cells).

ASIC currents were recorded with whole-cell patch-clamp and fast-perfusion techniques. The normal extracellular solution (ECF) contained (in mM) 140 NaCl, 5.4 KCl, 25 HEPES, 20 glucose, 1.3 $CaCl_2$, 1.0 $MgCl_2$, 0.0005 TTX (pH 7.4), 320-335 mOsm. For low pH solutions, various amounts of HCl were added. For solutions with pH<6.0, MES instead of HEPES was used for more reliable pH buffering. Patch electrodes contained (in mM) 140 CsF, 2.0 $MgCl_2$, 1.0 $CaCl_2$, 10 HEPES, 11 EGTA, 4 MgATP (pH 7.3), 300 mOsm. The $Na^+$-free solution consisted of 10 mM $CaCl_2$, 25 mM HEPES with equiosmotic NMDG or sucrose substituting for NaCl (Chu et al., 2002). A multi-barrel perfusion system (SF-77B, Warner Instrument Co.) was employed for rapid exchange of solutions.

Figure 32:
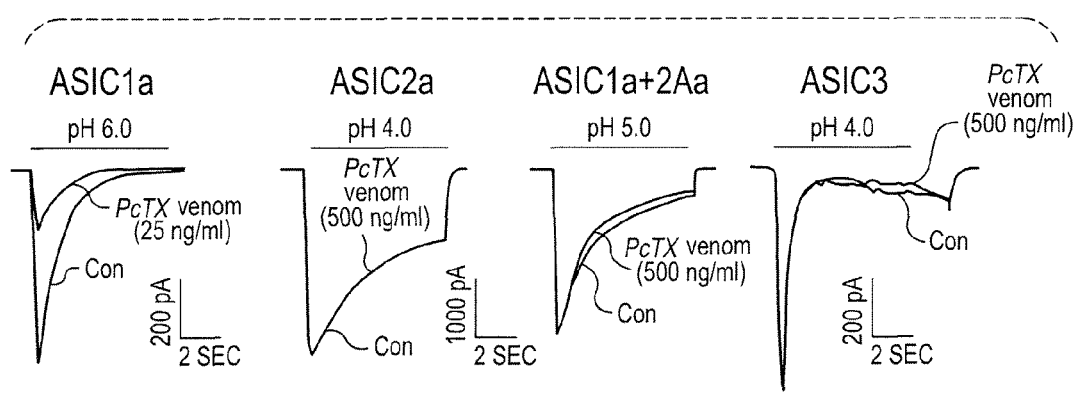
FIG. 32 is representative current traces showing the specificity of PcTX venom for currents mediated by homomeric ASIC1a expressed in COS-7 cells.

Currents were activated by lowering pH from 7.4 to indicated values according to the $pH_{50}$ of different subunit combinations. Channel currents were measured at the pH of half maximal channel activation (pH 0.5). As can be seen in FIG. 32 and FIG. 12, PcTX venom blocked the currents mediated by ASIC1a homomeric channels by about by ~70% at protein concentration of 25 ng/mL, with no effect on the currents mediated by homomeric ASIC2a, ASIC3, or heteromeric ASIC1a/ASIC2a at 500 ng/mL (n=3-6, FIG. 12). In addition, as described below, at 500 ng/mL, PcTX venom also did not affect the currents mediated by other ligand-gated channels (e.g. NMDA and GABA receptor-gated channels) and voltage-gated channels (e.g. Na+, Ca2+, and K+ channels) (n=4-5; FIG. 33 A-E).

Figure 33A:
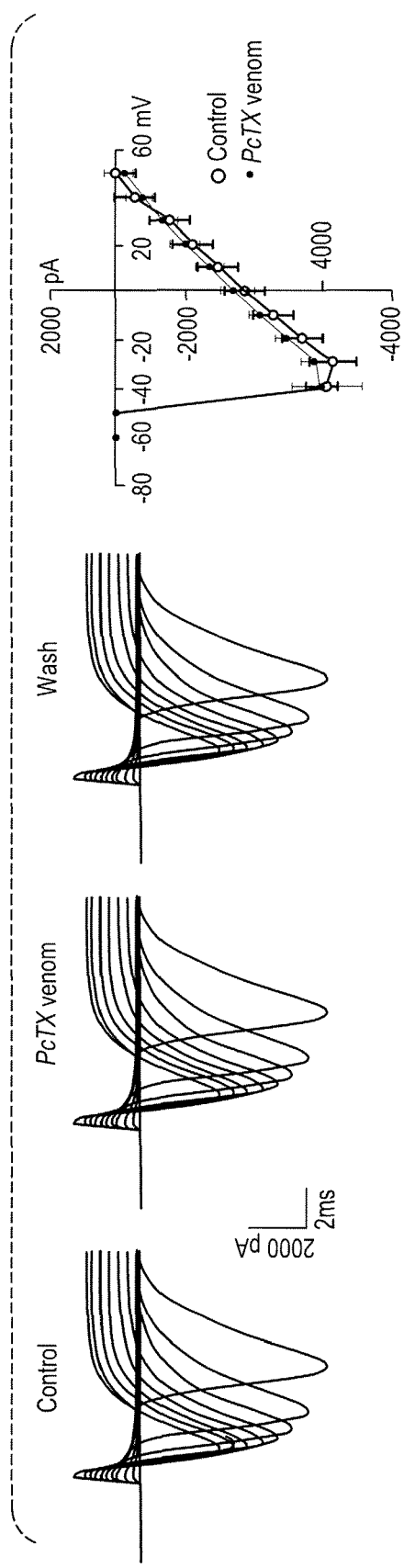
FIG. 33 A-E are representative current traces and summary bar graphs demonstrating the lack of effect of PcTX venom (500 ng/ml) on (A) voltage gated $Na^+$ channel currents; (B) voltage-gated $K^+$ channel currents; (C) voltage-gated $Ca^{2+}$ channel currents; (D) NMDA channel currents; and (E) GABA channel currents.

$Na^+$ currents were activated by depolarizing voltage pulses ranging from −60 to +50 mV with increment of +10 mV from a holding potential of −80 mV. Outward $K^+$ currents were suppressed by adding 5 mM TEA into the extracellular solution and by using a pipette solution containing 150 mM $Cs^+$. Following recording of stable $Na^+$ current, 500 ng/ml of PcTX venom was added into bath solution for 5 min. After recording the $Na^+$ current in the presence of venom, venom was completely washed out for 3-5 min and the $Na^+$ currents were rerecorded in the absence of PcTX venom. As shown in FIG. 33A, with the right panel showing the current-voltage relationship of the $Na^+$ channels before and after PcTX venom (n=5), the addition of PcTX venom did not effect the voltage gated $Na^+$ channels.

Figure 33B:
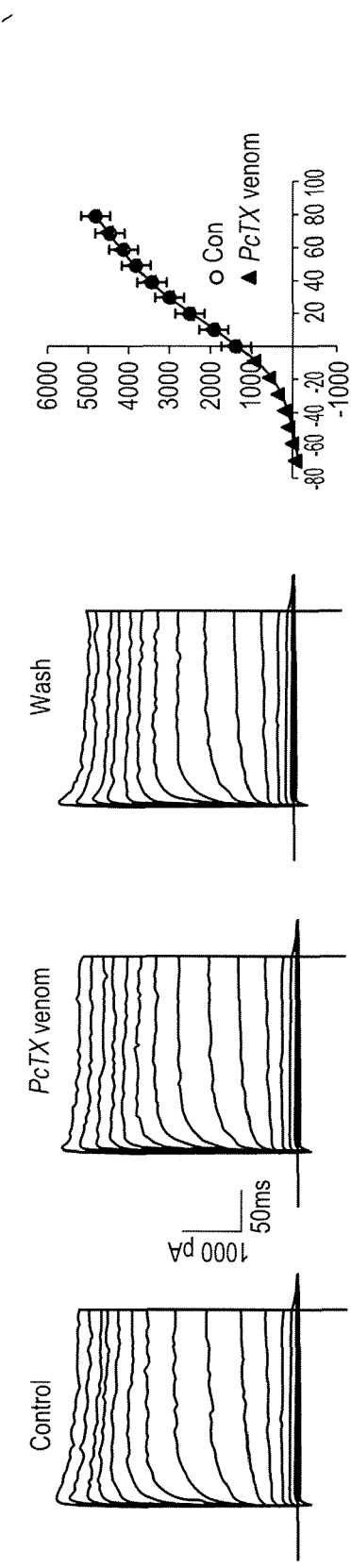
Figure 33C:
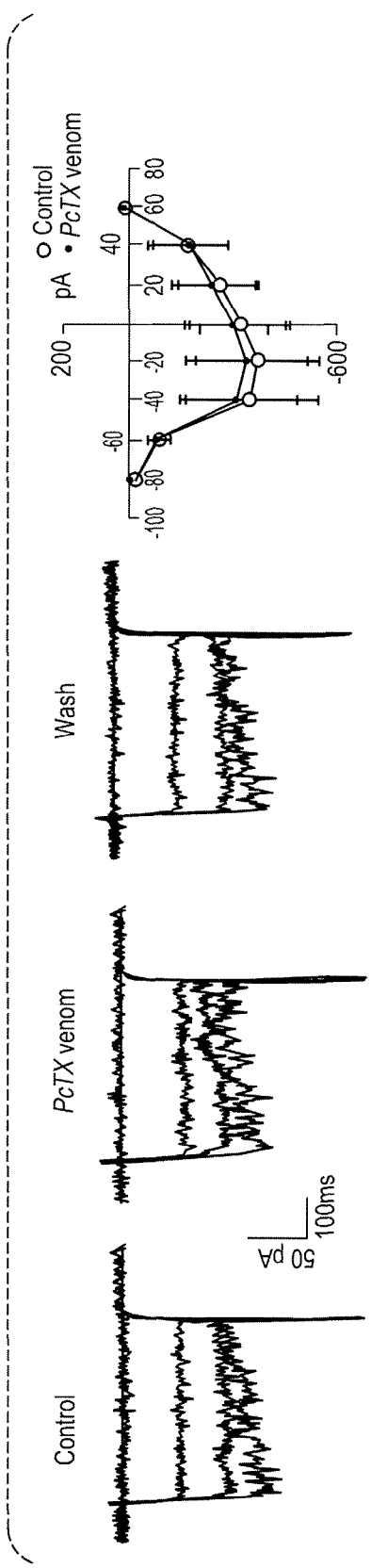
Figure 33D:
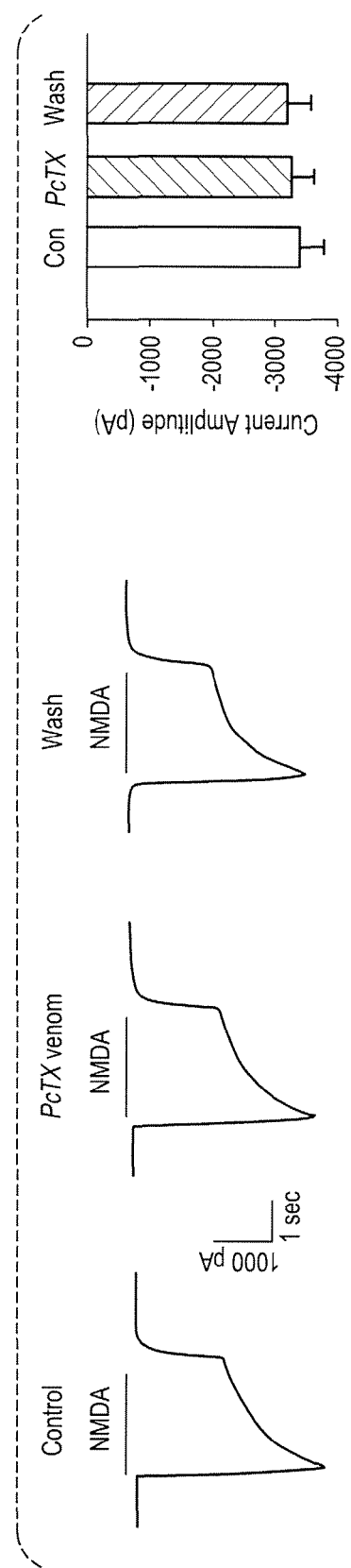

$K^+$ currents were activated by depolarizing voltage pulses ranging from −70 to +80 mV from a holding potential of −80 mV. Inward $Na^+$ currents were suppressed by adding 300 nM TTX into the extracellular solution. Pipette solution contained 150 mM $K^+$. As shown in FIG. 33B, with the right panel shows the current-voltage relationship of the $K^+$ channels before and after PcTX venom (n=5), PcTX venom had no effect on voltage-gated $K^+$ channel currents.

$Ca^{2+}$ channel currents were recorded using $Ba^{2+}$ as the charge carrier and were activated by depolarizing voltage pulses ranging from −60 to +60 mV with increments of +20 mV from a holding potential of −80 mV. Bath solution contained the following (in mM): 10 $BaCl_2$, 135 TEA-Cl, 10 glucose, 10 HEPES (pH 7.3) adjusted with Tris. Pipette solution contained the following: 120 CsCl, 20 TEA-Cl, 4 EGTA, 2 ATP-Mg, 10 HEPES (pH 7.2) adjusted with Tris. The effect of PcTX venom on $Ca^{2+}$ currents was studied 10 min after formation of whole-cell configuration when initial run down of the current reached its minimal. As shown in FIG. 33 C in which the right panel shows the current-voltage relationship of the $Ca^{2+}$ channels before and after PcTX venom (n=4), PcTX venom had no effect on voltage-gated $Ca^{2+}$ channel currents.

NMDA currents were activated by fast perfusion of NMDA (100 μM) in the presence of coagonist glycine (3 μM) with no added $Mg^{2+}$ in the extracellular solution. Holding potential was −60 mV. Pipette solution contained 150 mM CsF. As shown in FIG. 33 D in which the right panel is a summary data from five different neurons demonstrating the lack of effect on the amplitude of NMDA current by 5 min perfusion of PcTX venom (500 ng/ml), the addition of PcTX venom had no effect on NMDA channel currents.

Figure 33E:
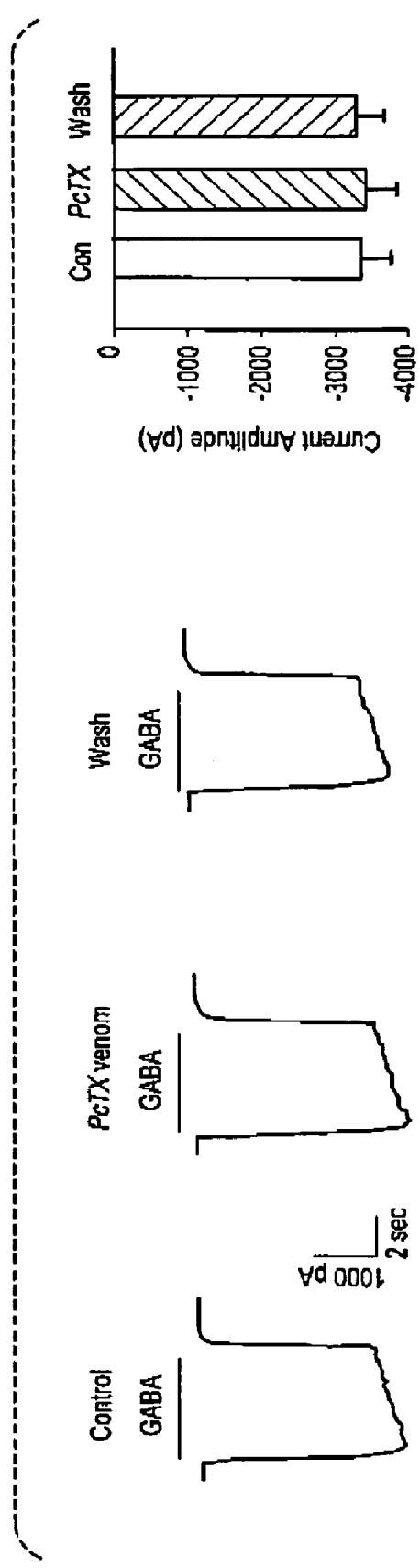

GABA currents were activated by fast perfusion of neurons with the extracellular solution containing 5 μM GABA. Holding potential was −60 mV. Pipette solution contained 150 mM CsCl. As shown in FIG. 33E in which the right panel is a summary data from four different neurons demonstrating the lack of effect on the amplitude of GABA current by PcTX venom (500 ng/ml), PcTX had no effect on GABA channel currents.

These experiments indicate that PcTX venom and thus PcTx1 peptide is a specific blocker for homomeric ASIC1a. Using this cell-based assay system, the potency and selectivity of ASIC inhibition may be measured for various synthetic peptides or other candidate inhibitors.

Example XVIII

Effect of Nasal Administration of PcTX Venom

This example describes exemplary data indicating the efficacy of nasally administered PcTX venom for reducing ischemia-induced injury in an animal model system of stroke; see FIG. 13.

Cerebral ischemia was induced for 60 minutes in male mice by suture occlusion of the middle cerebral artery (middle cerebral artery occlusion) in male rats (SD, 250-300 g) and mice (with congenic C57Bl6 background, ~25 g) anesthetized using 1.5% isoflurane, 70% $N_2O$, and 28.5% $O_2$ with intubation and ventilation. Rectal and temporalis muscle temperature was maintained at 37° C.±0.5° C. with a thermostatically controlled heating pad and lamp. Cerebral blood flow was monitored by transcranical LASER doppler. Animals with blood flow not reduced below 20% were excluded.

One hour after occlusion was initiated animals were treated as controls or were treated with PcTX venom (50 μL of 500 ng/mL (total protein) PcTX venom introduced intranasally). Animals were sacrificed 24 hours after middle cerebral artery occlusion. As shown in FIG. 13, nasal administration of PcTX venom resulted in a 55% reduction in ischemia-induced injury (ischemic damage), as defined by infarct volume, relative to control treatment.

Example XIX

Neuroprotective Time Window of PcTX in Focal Cerebral Ischemia

Male C57B mice (Charles River) weighing 25-30 g were housed under diurnal lighting conditions (12 h darkness and 12 h light). Experiments were performed according to the international guidelines for animal research. All experiments were performed in accordance with the American animal protection legislation and approved by the Institutional Animal Care and Use Committee of Legacy Research.

Transient focal ischemia was induced by suture occlusion of the middle cerebral artery in male mice anaesthetized using 1.5% isoflurane, 70% $N_2O$ and 28.5% $O_2$ (1). Ischemia was induced by introducing a coated filament (6.0; Doccol) from the external carotid artery into the internal carotid artery and advancing it into the arterial Will's Circle, thereby occluding the middle cerebral artery (Longa, E. Z., et al. Stroke 20:84-91 (1989)). Rectal and temporalis muscle temperature was maintained at 37° C.±0.5° C. with a thermostatically controlled heating pad and lamp. Cerebral blood flow was monitored by transcranial laser doppler. All surgical procedures were performed under an operating stereomicroscope.

For the mouse ischemia model, the left middle cerebral artery was occluded for 60 minutes, followed by 24 h of reperfusion. Achievement of ischemia was confirmed by monitoring regional cerebral blood flow in the area of the left middle cerebral artery. To determine the protective time window for ASIC1a blockade, PcTX venom, inactivated PcTX venom or vehicle was infused intracerebroventricularly 15 min, 1 h, 2 h, 2.5 h, 3 h, 5 h, and 6 h after middle cerebral artery occlusion. All mice were euthanized 24 hours after middle cerebral artery occlusion.

Figure 14A:
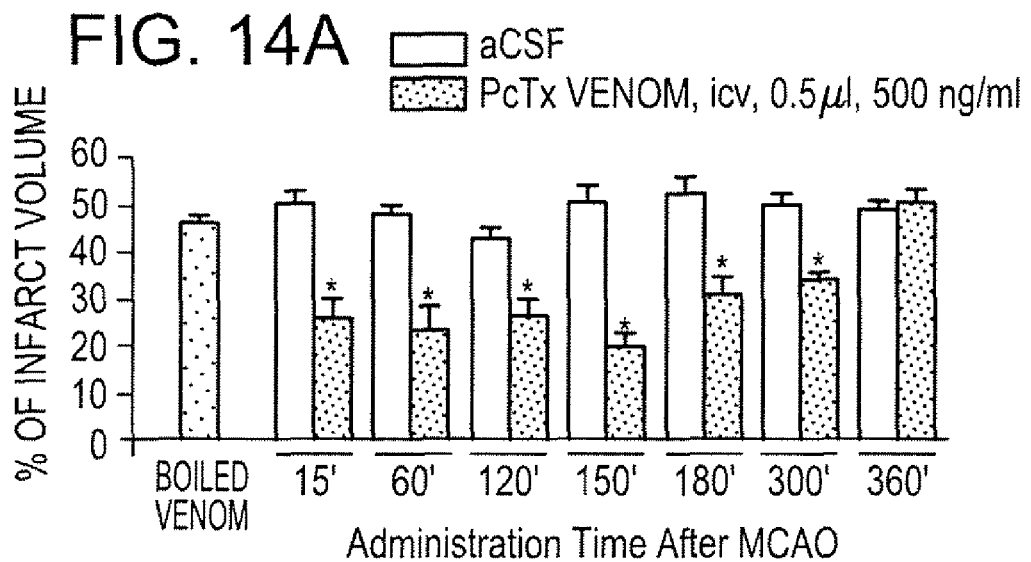
FIG. 14 is bar graphs showing (A) the effect of intracerebroventricular infusion of either boiled venom or PcTX venom 15 minutes, 1 hour, 2 hours, 2.5 hours, 3 hours, 5 hours, and 6 hours after middle cerebral artery occlusion and (B) of the dose dependent effect of PcTX venom administered intracerebroventricularly after mid-cerebral artery occlusion.

The percentage of infarct volume in the vehicle injected animals was 50.57±2.35, 48.09±1.72, 42.69±1.72, 50.89±3.13, 50.57±2.35, 50.59±2.14, 50.64±3.14 of the ipsilateral hemisphere, respectively (n=5 for each group, FIG. 14A). However, intracerebroventricularly injection of PcTX (0.5 μl, 500 ng/mL total protein, ~10 ng/kg) at 15 min (n=6), 1 h (n=5), 2 h (n=10), 2.5 h (n=5), 3 h (n=11) or 5 h (n=8) after middle cerebral artery occlusion significantly reduced the percentage of the infarct volume to 25.79±4.23, 23.18±5.36, 19.77±3.09, 26.42±3.84, 30.95±4.05, or 34.22±1.64, respectively (FIG. 14A). In contrast, inactivated (boiled) PcTX venom (0.5 μl, 500 ng/mL total protein, n=5) was not protective even when it was injected at 1 h (infarct volume: 46.4±1.4%, n=5) (FIG. 14A). Also, PcTX injection at 6 h did not reduce the infarct volume (n=5, infarct volume: 51.02±4.28%) (FIG. 14A). *P<0.05 vs. boiled PcTX treated mice and vehicle-treated group.

Example XX

Effect of PcTX on Cell Death in Ischemic Model

To determine whether PcTX indeed prevented the cell death or only delayed it, observations of infarct volume to 7 days after the ischemia.

Transient focal ischemia was induced by suture occlusion of the middle cerebral artery in male mice anaesthetized using 1.5% isoflurane, 70% $N_2O$ and 28.5% $O_2$ (1). Ischemia was induced by introducing a coated filament (6.0; Doccol) from the external carotid artery into the internal carotid artery and advancing it into the arterial Will's Circle, thereby occluding the middle cerebral artery (32). Rectal and temporalis muscle temperature was maintained at 37° C.±0.5° C. with a thermostatically controlled heating pad and lamp. Cerebral blood flow was monitored by transcranial laser doppler. All surgical procedures were performed under an operating stereomicroscope. To induce permanent middle cerebral occlusion (MCAO) the same procedure was used except that the coated filament was not removed until the animal was killed.

1 hour after middle cerebral artery occlusion, 0.5 μL, 500 ng/mL PcTX, or vehicle (0.5 μL, n5) was administered intracerebroventricularly. All mice were euthanized one day after middle cerebral artery occlusion.

Figure 15A:
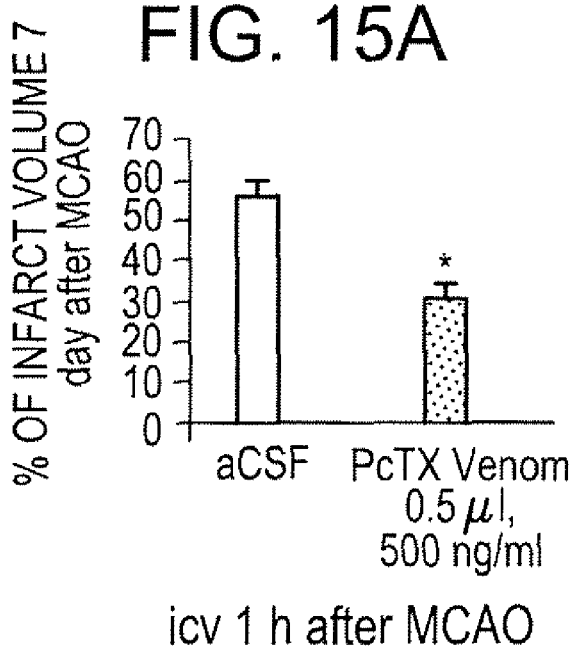
FIGS. 15 A and B are graphs of infract volume 7 days after treatment with PcTX in (A) transient and (B) permanent middle cerebral artery occlusion.
Figure 15B:
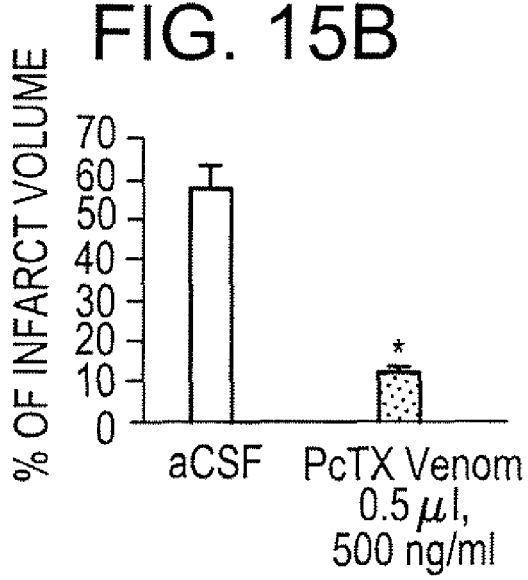

Although shrinkage of the ischemic hemisphere was observed in both treated and control animals, PcTX still decreased infarct volume by ~50% (23.9±3.5 v.s. 53.4±2.4%, n=6, FIG. 15A) at 7 days. Interestingly, more pronounced reduction of infarct volume by PcTX (injected 1 h after occlusion) was obtained in a permanent model of cerebral ischemia (12.3±1.7 v.s. 57.6±5.1%, n=5, FIG. 15B). *P<0.05 vs. vehicle treated groups.

Figure 14B:
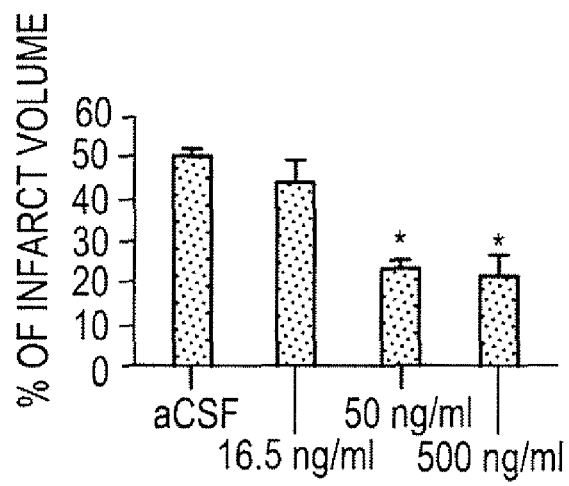

To evaluate the dose-dependent effective of PcTX, ten and thirty times diluted PcTX were also used. PcTX venom (0.5 μL) at concentrations of 500 ng/ml, 50 ng/ml and 16.5 ng/ml was infused intracerebroventricularly 1 hour after mid-cerebral arter occlusion. All mice were euthanized 24 hours after occlusion. As can be seen in FIG. 14B, a significant reduction of infarct volume (by ~40%) was observed when PcTX venom was used at a total protein concentration of 1 ng/kg (0.5 μl@50 ng/mL, n=5, % of infarct: 23.6±2.3), while further decrease of dose to 0.3 ng/kg (0.5 μl@16.5 ng/mL, n=5) didn't show significant protection (n=5, % of infarct: 43.9±3.1) P<0.05 vs. vehicle treated group.

Example XXI

Effect of Systemic Administration of PcTX

Although intracerebroventricularly administration of ASIC1 blocker provided prolonged protective time window, this routine of delivery may be difficult to achieve clinically. For this reason, we have determined whether this peptide is still effective if administered systemically.

Transient focal ischemia was induced by suture occlusion of the middle cerebral artery in male mice anaesthetized using 1.5% isoflurane, 70% $N_2O$ and 28.5% $O_2$ (1). Ischemia was induced by introducing a coated filament (6.0; Doccol) from the external carotid artery into the internal carotid artery and advancing it into the arterial Will's Circle, thereby occluding the middle cerebral artery (32). Rectal and temporalis muscle temperature was maintained at 37° C.±0.5° C. with a thermostatically controlled heating pad and lamp. Cerebral blood flow was monitored by transcranial laser doppler. All surgical procedures were performed under an operating stereomicroscope. To induce permanent middle cerebral occlusion (MCAO) the same procedure was used except that the coated filament was not removed until the animal was killed.

PcTX was administered through the femoral vein (IV) and through the nasal cavity 1 hour after occlusion. Unfortunately, IV administration of PcTX venom 1 h after ischemia was not able to modify the infarct volume (% of infarct volume: 49.1±5.5 with PcTx1 injection v.s. 47.9±1.7 with saline injection, n=5 in each group), probably due to the metabolism or breakdown of the peptide (not shown). By contrast, intranasal administration of PcTX was able to reduce the infarct volume by 50% when it was administered 1 h after middle cerebral artery occlusion (n=5, infarct volume: 21.4±2.4%). Same protection was recorded when PcTX was intranasal administered 4 h after middle cerebral artery occlusion (n=5, infarct volume: 23.8±1.8%). In vehicle treated animals, the percentage of the infarct volume was 53.4±3.6 (n=5) (FIG. 16). P<0.05 vs vehicle treated ischemic mice.

Example XXII

Combinatorial Formulations of PcTX

To investigate the potential interaction between NMDA and ASIC1a blockade on infarct volume, memantine was administered before or after PcTX administration in rodents subjected to 60 min of middle cerebral artery occlusion and evaluated one day after ischemia induction.

Transient focal ischemia was induced by suture occlusion of the middle cerebral artery in male mice anaesthetized using 1.5% isoflurane, 70% $N_2O$ and 28.5% $O_2$ (1). Ischemia was induced by introducing a coated filament (6.0; Doccol) from the external carotid artery into the internal carotid artery and advancing it into the arterial Will's Circle, thereby occluding the middle cerebral artery (32). Rectal and temporalis muscle temperature was maintained at 37° C.±0.5° C. with a thermostatically controlled heating pad and lamp. Cerebral blood flow was monitored by transcranial laser doppler. All surgical procedures were performed under an operating stereomicroscope.

Rodents were treated with saline, PcTX and/or memantine according to the following schedule: Saline IP administered 30 min after middle cerebral artery occlusion; PcTX 15: (0.5 µL, 500 ng/mL) administered 15 min after middle cerebral artery occlusion; Memantine 30 (1 mL, 10 mg/kg) administered 30 min after middle cerebral artery occlusion; PcTx15 min/Memantine 30, 60 120; PcTX (0.5 µL, 500 ng/mL) administration 15 min after middle cerebral artery occlusion followed by IP Memantine (1 mL, 10 mg/kg) administration 30 min, 60 min, or 120 min after PcTX. Memantine1 5/PcTx 180, 300, 360: Memantine (1 mL, 10 mg/kg) administration IP 15 min after middle cerebral artery occlusion followed by intracerebraventricular PcTX (0.5 µL, 500 ng/mL) 180 min, 300 min, or 360 min after Memantine. N=5 animals per group. All mice were euthanized 24 h after middle cerebral artery occlusion. *P<0.05 vs. control group; **P<0.05 vs. control group, PcTX treated mice and Memantine-treated mice.

Figure 17:
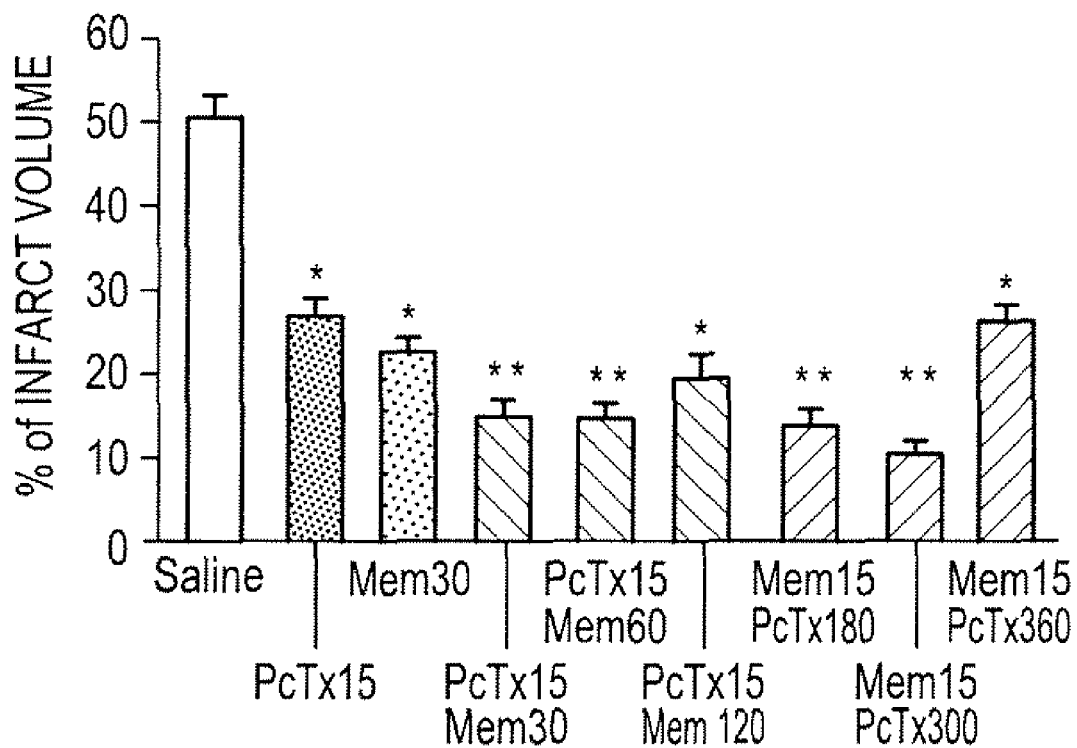
FIG. 17 is a graph presenting exemplary data from experiments measuring the percentage of brain infarct volume as a function of the time (in minutes) of administration of PcTX venom and/or of the NMDA receptor antagonist memantine (Mem) after mid-cerebral artery occlusion.

A reduction of the infarct volume greater than that observed from PcTX alone was observed when memantine (10 mg/kg) was administered intraperitoneally 30 minutes (n=5, infarct volume: 15.9±2.2%) and 1 h (n=5, 15.6±1.8%) after middle cerebral artery occlusion, in PcTX (10 ng/kg, injected 15 min after middle cerebral artery occlusion) treated mice. Similarly, an additional protection was observed when PcTX was administered 3 h (n=5, infarct volume 16.1±1.9%) or 5 h after middle cerebral artery occlusion (n=5, infarct volume 10.8±1.2%), in memantine (10 mg/kg, 15 min after middle cerebral artery occlusion) treated mice (FIG. 17).

Interestingly, a prolonging of the memantine therapeutic time window was also observed when it was administered following the PcTX administration. FIG. 18 is a graph presenting exemplary data from experiments measuring the percentage of brain infarct volume as a function of the time (in minutes) of administration of memantine after mid-cerebral artery occlusion, in accordance with aspects of the present teachings. Memantine's time window (1 mL, 10 mg/kg). Memantine (0.1 mL, 10 mg/kg) or saline solution (1 mL) was IP-administered 15 minutes, 1 h, or 3 h after ischemia induction. All mice were euthanized 24 h after middle cerebral artery occlusion. Each column represents the mean±SE of the percentage of the infarct compared to the ipsilateral hemisphere. Each experimental group consisted of 5 animals. *P<0.05 vs. vehicle-treated ischemic mice.

Memantine alone administered intraperitoneally 1 h after middle cerebral artery occlusion was not able to produce a neuroprotective effect (infarct volume: 40.3±4.3% with memantine v.s. 50.6±2.3% with saline, n=5 in each group) (FIG. 18). This finding is consistent with various published studies (19). To verify if the limited therapeutic time window is due to the memantine concentration used, the effect of different dosages of the memantine, 1 mg/kg, 30 mg/kg, and 100 mg/kg, were evaluated. In all cases, when memantine was administered 1 h after middle cerebral artery occlusion, we didn't observe any significant reduction of the infarct volume. In the vehicle treated animals (n=5), the percentage of the infarct volume was 50.6±2.3, while in animals treated with 1 mg/kg (n=5), 10 mg/kg (n=5), or 30 mg/kg (n=5) memantine the infarct volume was 55.4±5.2, 41.0±3.4, and 43.4±3.8, respectively. Surprisingly, all the mice treated with the highest dosage of memantine (100 mg/kg, n=5) died (not shown).

By contrast, intrperitoneal administration of 10 mg/kg memantine 1 h after middle cerebral artery occlusion provided an additional neuroprotection when administered in PcTX treated animals (15.6±1.8, as compared to 41.0±3.4 for memantine alone or to 23.18±5.36 for PcTX alone, FIG. 18).

Example XXIII

Neuroprotection by Intracerebroventricularly Injection of Bicarbonate

To determine if alkalinization of the ischemic brain tissue is able to attenuate brain damage, a sodium bicarbonate solution was intracerebroventricularly infused at different concentrations and at different times (1 h, 4 h, or 5 h) following middle cerebral artery occlusion.

Transient focal ischemia was induced by suture occlusion of the middle cerebral artery in male mice anaesthetized using 1.5% isoflurane, 70% $N_2O$ and 28.5% $O_2$ (1). Ischemia was induced by introducing a coated filament (6.0; Doccol) from the external carotid artery into the internal carotid artery and advancing it into the arterial Will's Circle, thereby occluding the middle cerebral artery (32). Rectal and temporalis muscle temperature was maintained at 37° C.±0.5° C. with a thermostatically controlled heating pad and lamp. Cerebral blood flow was monitored by transcranial laser doppler. All surgical procedures were performed under an operating stereomicroscope.

Mice were treated with aCSF or bicarbonate (0.5 µL) at three different concentrations, 0.025 mg/kg, 0.25 mg/kg, or 2.5 mg/kg, intracerebroventricularly-infused 1 h after ischemia induction. All mice were euthanized 24 h after MCAO.

Figure 19A:
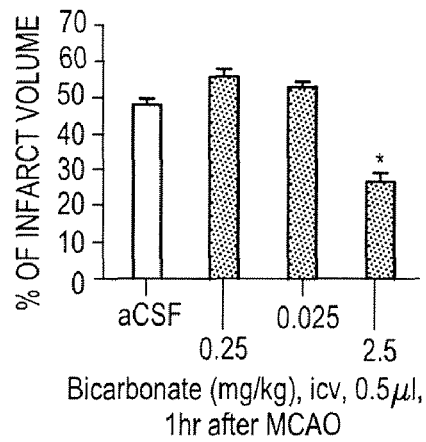
FIGS. 19A-C are a series of graphs showing (A) the effect of sodium bicarbonate on infarct volume induced by 60 min of middle cerebral artery occlusion; (B) the effect of intracerebroventricular bicarbonate administration on infarct volume induced by 60 min of middle cerebral artery occlusion, evaluated 1 day after ischemia induction; (C) shows the combined effect of intracerebroventricular PcTX and intracerebroventricular $NaHCO_3$ on infarct volume induced by 60 min of middle cerebral artery occlusion, evaluated 1 day after ischemia induction.

The effective concentration of bicarbonate was established to be 2.5 mg/kg (n=5, infarct volume 26.2±2.6%). Lower concentrations, for example, 0.25 mg/kg (n=5, infarct volume 52.4±1.5%) or 0.025 (n=5, infarct volume 54.1±2.1%) didn't have any effect on the infarct volume, compared to the vehicle injected mice (n=5, infarct volume: 48.1±1.7%) (FIG. 19A). (*P<0.05 vs. vehicle-treated ischemic mice; mean±SE of the percentage of the infarct compared to the ipsilateral hemisphere).

In a second experiment, bicarbonate (0.5 µL, 2.5 mg/kg) or aCSF (0.5 µL) were intracerebroventricularly-administered 1 h or 4 h after ischemia induction. All mice were euthanized 24 h after middle cerebral artery occlusion. Each experimental group consisted of 5 animals. *P<0.05 versus vehicle treated ischemic mice.

Figure 19B:
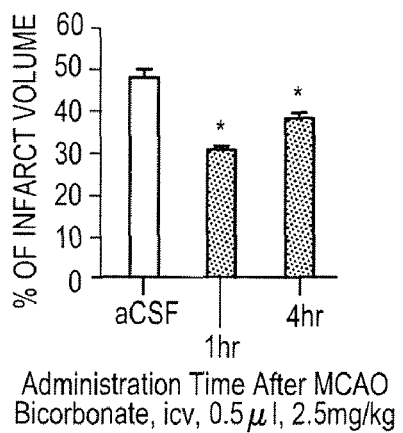

Similarly to PcTX injection, the neuroprotective effect by bicarbonate was still present with delayed administration. For example, when bicarbonate (2.5 mg/kg) was administered 4 h after middle cerebral artery occlusion, a significant protection was still present. The relative infarct volume was 48.9±1.72% in aCSF-injected mice (n=5), but only 34.5±1.27% in animals treated with bicarbonate 4 h after middle cerebral artery occlusion (n=6) (FIG. 19B).

In contrast to intracerebroventricularly, intravenous injection of bicarbonate was not effective. The percentage of the infarct were 60.44±4.75% for saline, 61.51±5.03% and 55.4±7.89% for 2.5 mg/kg and 5 mg/kg bicarbonate treated mice, respectively (n=5 for all groups, not shown). The failure to see neuroprotective effect by intravenously injected bicarbonate may be explained by the finding that intravenous injection of bicarbonate is less effective in modifying brain pH. By contrast, when bicarbonate was intracerebroventricularly administered 2 h after reperfusion, a marked and sustained increase in the brain pH value from 6.60±0.60 to 7.25±0.25 was observed (n=3, FIG. 20B).

Figure 19C:
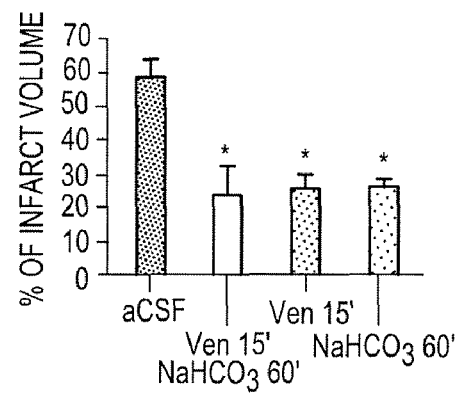

That bicarbonate acts avoiding the activation of ASIC1A is proved by the fact that the administration of bicarbonate (intracerebroventricularly, 0.5 μl, 2.5 mg/kg) 60' after middle cerebral artery occlusion in ischemic mice treated with PcTX venom 15' (icv, 0.5 μl, 500 ng/mL) after middle cerebral artery occlusion does not induce a further reduction of the infarct volume (24.4±7.5, n=5) if compared with the effect of PcTX venom alone (25.8±4.2) or bicarbonate alone (26.2±2.6) (FIG. 19C).

Example XXIV

Alteration of Brain Tissue pH after Ischemia

A prolonged neuroprotective time window with ASIC1a blockade suggests that there is persistent acidosis in ischemic brain which activates the ASIC channels. We have, therefore, measured brain pH continuously with a fiber optic pH sensor in the ipsilateral and contralateral parietal cortex of mice immediately after the removal of the middle cerebral artery suture, to determine the degree, distribution, and the time course of acidosis following focal ischemia. Cerebral pH was evaluated in sham-operated animals, in vehicle-treated animals, in PcTX venom-treated animals, and in sodium bicarbonate treated animals. Values are mean±SE (n=3 for each group).

Transient focal ischemia was induced in rodents by suture occlusion of the middle cerebral artery in male mice anaesthetized using 1.5% isoflurane, 70% $N_2O$ and 28.5% $O_2$ (1). Ischemia was induced by introducing a coated filament (6.0; Doccol) from the external carotid artery into the internal carotid artery and advancing it into the arterial Will's Circle, thereby occluding the middle cerebral artery (32). Rectal and temporalis muscle temperature was maintained at 37° C.±0.5° C. with a themostatically controlled heating pad and lamp. Cerebral blood flow was monitored by transcranial laser doppler. All surgical procedures were performed under an operating stereomicroscope.

For continuous measurement of pH in the brain, a fiber optic pH micro system (pHOptica, WPI) was used. This system has a pH range between 5 and 9, and the resolution is ±0.003 units. A glass-fiber with its pH-sensitive tip (140 μM OD) was stereotaxically implanted into the brain immediately after the middle cerebral artery occlusion at the following coordinates from the bregma: 2.4 mm laterally, 0.1 posteriorly and 2.2 mm deep. pH was continuously measured for 6 h. The instrument was calibrated with standard solutions (pH 4.0, 5.0, 6.0, 7.0, 8.0, and 9.0) before and after the experiments. To mimic the brain environment the standard solutions were pre-warmed at 37.0 C and the calibration was performed in the absence of light. Changes in pH values were evaluated after PcTX and $NaHCO_3$ intracerebroventricularly or intravenous administration 2 hours after occlusion.

To correlate pH values and ischemic damage, mice were sacrificed 1 h, 2 h and 4 h after reperfusion. Brains were quickly removed, sectioned coronally at 1 mm intervals, and stained by immersion in the vital dye (2%) 2,3,5-triphenyltetrazolium hydrochloride (TTC) (Bederson, J. B. et al., Stroke 17: 1304-1308 (1986). The infarct volume was calculated by summing infarction areas of all sections and multiplying by slice thickness. The percentage of the infarct was calculated by dividing the infarct volume by the total ipsilateral hemispheric volume (Pignataro, G., Stroke 35:2566-2570 (2004).

Figures 20A, 20B:
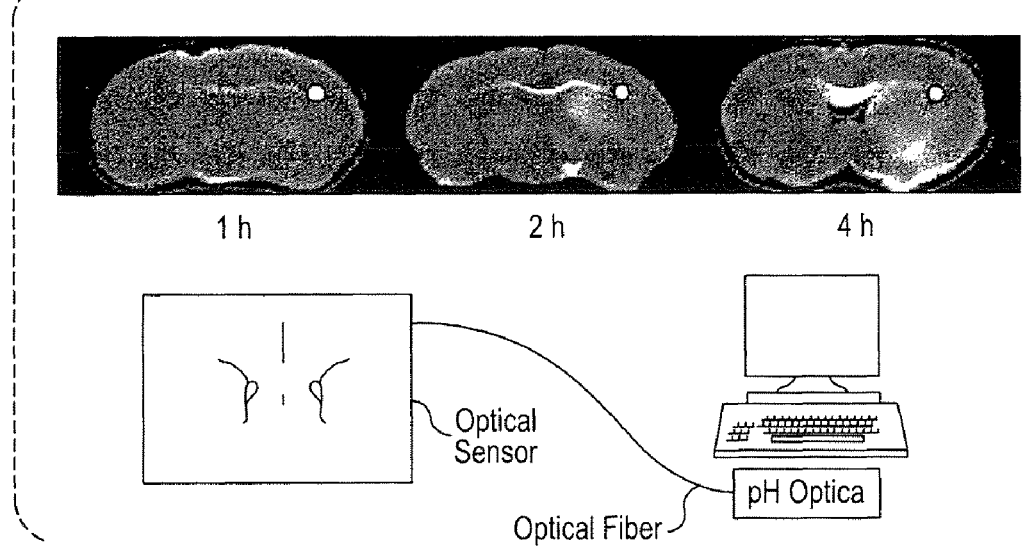
FIGS. 20 A and B is data on pH measurement from ischemic mice sacrificed at the indicated time after reperfusion displayed in (A) as a series of photographs of TTC-stained brain sections, with the circle indicating the point at which a pH measurement was taken with the optical measurement system (microfiber optic pH system) shown below the photographs, and (B) a table of the pH data obtained using the optical measurement system of FIG. 20A at the indicated times after mid-cerebral artery occlusion and with the indicated treatments performed two hours after occlusion FIG. 21 A-D is a series of graphs showing (A) patch-clamp recordings of ASIC1a-mediated ion currents measured in Chinese hamster ovary (CHO) cells expressing exogenous ASIC1a protein in the presence or absence of synthetic PcTx1; (B) patch-clamp recordings of acid-induced ion currents in cultured mouse cortical neurons in the presence or absence of various concentrations of synthetic PcTx1; (C) a summary bar graph plotting inhibition of ASIC1a-mediated current in CHO cells by different concentrations of synthetic PcTx1 peptide added six minutes prior to acidification and (D) exemplary dose-response curve for blockade of the acid-induced ion current in CHO cells by synthetic PcTx1 peptide.

Tissue pH of the parietal cortex (coordinates from bregma: 2.4 mm laterally, 0.1 posteriorly and 2.2 mm deep) measured immediately after reperfusion was 7.17±0.03 (n=5, FIG. 20B). Interestingly, an increase of pH to 7.50±0.08 was observed in this area during the first hour of reperfusion. After this, pH dropped gradually and a markedly acidic pH value was observed at 3 h (6.74±0.06), 4 h (6.60±0.04) and 5 h (6.43±0.04) after the reperfusion (FIG. 20A). No significant changes in pH values were observed in sham-operated animals, and the intracerebroventricularly injection of PcTX had no effect on pH changes (FIG. 20B)

Interestingly, the alkalizing pH was detected when the damage was close to the area in which pH was measured (the circle in the photographs in 20 A indicates the point at which a pH measurement was taken with the optical measurement system). In other words an alkalinization is observed in the so-called penumbra area where the damage develops later. When this area is damaged and becomes ischemic core, a sustained reduction of pH values was observed.

Example XXV

Effect of Synthetic PcTx1 on ASIC Currents of Cultured Cells

This example describes exemplary effects of synthetic PcTx1 peptide on ASIC currents recorded in CHO cells and in cultured mouse cortical neurons, with or without exposure to a synthetic PcTx1 peptide.

Following anesthesia with halothane, cerebral cortices were dissected from E16 Swiss mice or P1 $ASIC1^{+/+}$ and $ASIC1^{-/-}$ mice and incubated with 0.05% trypsin-EDTA for 10 min at 37° C. Tissues were then triturated with fire-polished glass pipettes and plated on poly-L-ornithine-coated 24-well plates or 25×25 mm glass coverslips at a density of $2.5×10^5$ cells per well or $10^6$ cells per coverslip. Neurons were cultured with MEM supplemented with 10% horse serum (for E16 cultures) or Neurobasal medium supplemented with B27 (for P1 cultures) and used for electrophysiology and toxicity studies after 12 days. Glial growth was suppressed by addition of 5-fluoro-2-deoxyuridine and uridine, yielding cultured cells with ~90% neurons as determined by NeuN and GFAP staining (data not shown).

ASIC currents were recorded with whole-cell patch-clamp and fast-perfusion techniques. The normal extracellular solution (ECF) contained (in mM) 140 NaCl, 5.4 KCl, 25 HEPES, 20 glucose, 1.3 $CaCl_2$, 1.0 $MgCl_2$, 0.0005 TTX (pH 7.4), 320-335 mOsm. For low pH solutions, various amounts of HCl were added. For solutions with pH<6.0, MES instead of HEPES was used for more reliable pH buffering. Patch electrodes contained (in mM) 140 CsF, 2.0 $MgCl_2$, 1.0 $CaCl_2$, 10

HEPES, 11 EGTA, 4 MgATP (pH 7.3), 300 mOsm. The Na$^+$-free solution consisted of 10 mM $CaCl_2$, 25 mM HEPES with equiosmotic NMDG or sucrose substituting for NaCl (Chu et al., 2002). A multi-barrel perfusion system (SF-77B, Warner Instrument Co.) was employed for rapid exchange of solutions.

In the cortical neurons, synthetic PcTx1 peptide at a concentration of 200 nM inhibited the majority of the acid-induced ion current, indicating that ASIC1a was responsible for at least a majority of the acid-induced ion current. (FIG. 21 B)

Chinese hamster ovary (CHO) cells expressing exogenous ASIC1a protein were acidified to pH 6.0 in the absence or presence of various concentrations of chemically synthesized PcTx1 peptide, or acidified to pH 6.5 for various times of pretreatment with PcTx1 peptide at 200 nM. As shown in FIGS. 21A and C, PcTx1 peptide at 200 nM inhibited the majority of the ASIC1a current after exposure of the cells to the peptide for about five minutes.

Figure 21B:
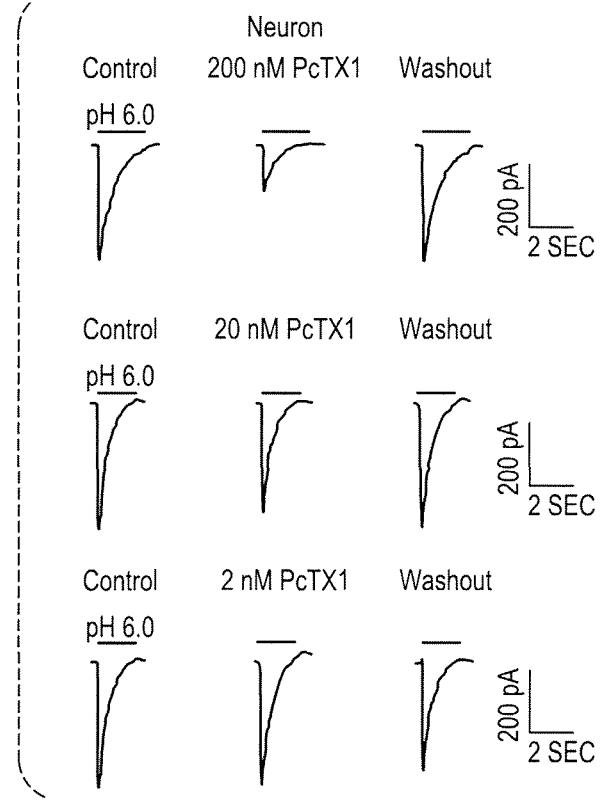
Figure 21C:
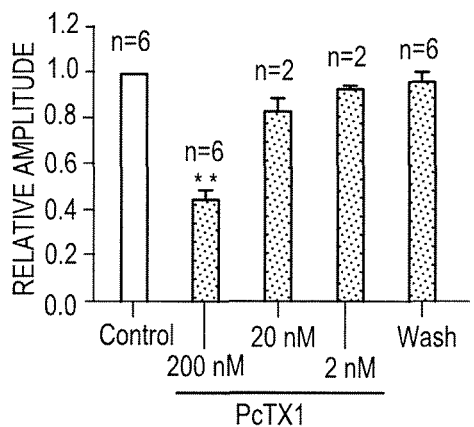
Figure 21D:
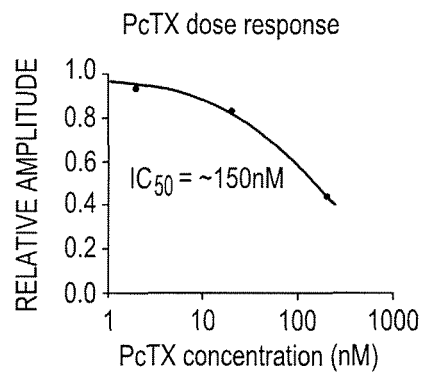

As shown in FIG. 21 D, the dose-response curve for blockade of the acid-induced ion current in CHO cells by synthetic PcTx1 peptide indicates a half-maximal inhibitory concentration ($IC_{50}$) of ~150 nM for inhibition of the ion current by the synthetic peptide. However, this half-maximal inhibitory concentration may be affected substantially by the tertiary structure of the peptide and thus by the procedure used for folding the peptide after peptide synthesis. For example, another preparation of the peptide of comparable purity produced an $IC_{50}$ of about 2 nM. Accordingly, the activity of the peptide may be dependent upon the percentage of peptide that is in an active conformation.

Example XXVI

In Vivo Neuroprotection by Synthetic PcTx1 after Stroke

Mice were used to compare the efficacy of synthetic PcTx1 peptide for reduction of ischemic damage resulting from stroke. Stroke was induced experimentally in the mice by mid-cerebral artery occlusion.

Transient focal ischemia was induced in rodents by suture occlusion of the middle cerebral artery in male mice anaesthetized using 1.5% isoflurane, 70% $N_2O$ and 28.5% $O_2$ (1). Ischemia was induced by introducing a coated filament (6.0; Doccol) from the external carotid artery into the internal carotid artery and advancing it into the arterial Will's Circle, thereby occluding the middle cerebral artery (32). Rectal and temporalis muscle temperature was maintained at 37° C.±0.5° C. with a thermostatically controlled heating pad and lamp. Cerebral blood flow was monitored by transcranial laser doppler. All surgical procedures were performed under an operating stereomicroscope.

The mice were treated by intracerebroventricular infusion of artificial cerebrospinal fluid (aCSF), with or without synthetic PcTx1 peptide (sPcTX), 15 minutes after occlusion (i.e., 15 minutes after stroke). The synthetic PcTx1 peptide was infused to achieve a dose of 10 nM in the brain of each mouse. The mice were sacrificed 24 hours later and then were analyzed for the percentage of ischemic damage to their brains. The graph of FIG. 22 plots the percentage of ischemic damage for 10 mice treated with aCSF or with sPcTX. * $P<0.05$ vs. vehicle treated group. As shown in FIG. 22, infusion of synthetic PcTx1 peptide produces about a 70% decrease in the amount of brain damage relative to control vehicle (aCSF).

Example XXVII

Treatment of Seizure-Like Activity and Seizures with ASIC-Blockers

This example describes exemplary data showing the ability of an ASIC1a-selective inhibitor (PcTX venom) and/or a non-selective sodium channel/ASIC blocker (amiloride) to reduce seizure-like activity in cultured hippocampal neurons and hippocampal explants, and to reduce seizure-induced injury in the mouse brain; see FIGS. 23-27.

Hippocampal slices were bathed in magnesium-free artificial cerebrospinal fluid (aCSF). The absence of magnesium in the fluid makes neurons in the slice susceptible to seizure-like electrical activity. Accordingly, the hippocampal slice maintained in magnesium-free fluid provides a model system for epilepsy. Electrical potential was measured prior to addition of any compounds, after treatment with PcTX venom followed by electrical stimulation, after PcTX venom was removed, with amiloride, during transient removal of kyneuric acid, and kainic acid to promote seizure activity in the mice with or without injection of PcTX venom.

The three graphs in panel 23A show the electrical potential measured from the same hippocampal slice after electrical stimulation near the beginning of each voltage trace, to promote depolarization followed by re-polarization (a peak(s) in the voltage trace). Electrical stimulation of a control hippocampal slice, bathed in fluid with a physiological magnesium level, produced a single peak in the voltage trace (not shown here). In contrast, as shown here in the first graph of panel 23A, electrical stimulation of a hippocampal slice maintained in aCSF without magnesium produced a series of individual peaks, indicative of seizure-like activity. The second graph of panel A shows a voltage trace measured after incubation of the hippocampal slice in PcTX venom (200 ng/mL) for 23 minutes and then followed by a pulse of electrical stimulation near the beginning of the trace. Here, the smaller individual peaks are no longer present, demonstrating that PcTX venom blocked the seizure-like activity. The third graph of panel 23A shows a voltage trace measured after removal of the PcTX venom, namely, replacement of the venom with a magnesium-free fluid for 19 minutes and then followed by a pulse of electrical stimulation near the beginning of the voltage trace. Here, the smaller individual peaks are present again, demonstrating that the inhibition of seizure-like activity exhibited by PcTX venom is reversible. Panel B shows the three voltage traces from panel A superimposed in a single graph.

Figure 23A:
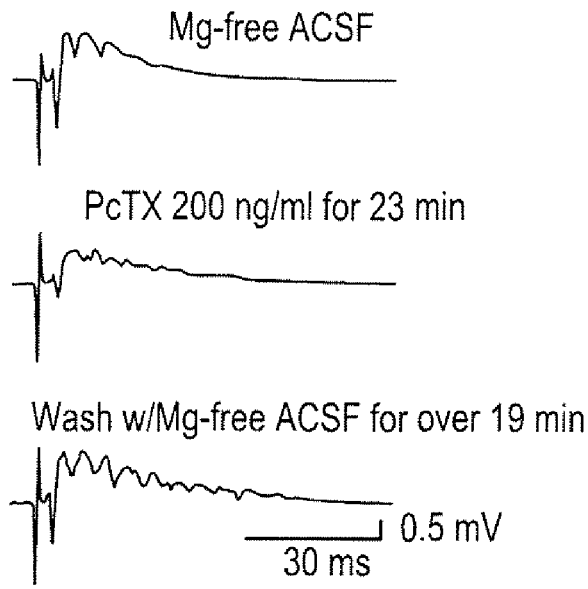
FIG. 23 is a series of graphs presenting exemplary data for electrical potential measured over time from a hippocampal slice incubated in magnesium-free fluid (to provide a model system for epilepsy), with or without PcTX venom.
Figure 23B:
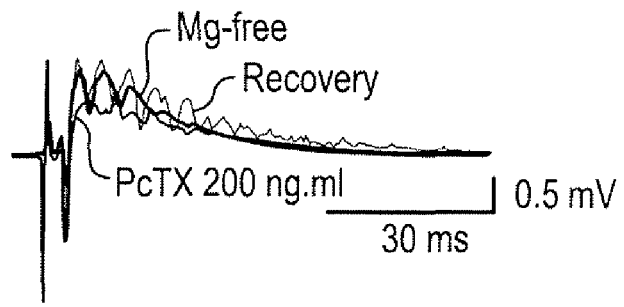
Figure 24A:
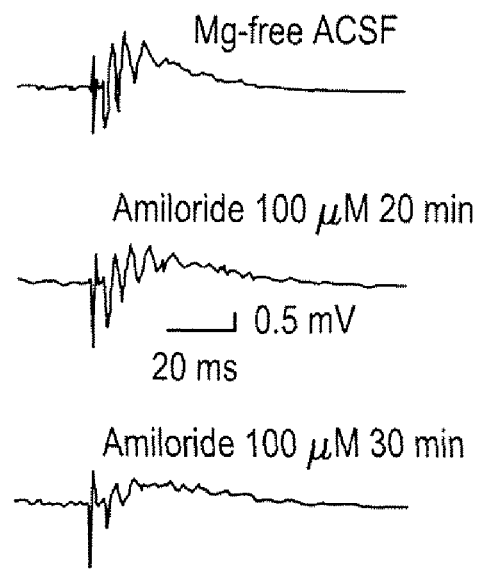
FIG. 24 is a series of graphs presenting exemplary data for electrical potential measured from a hippocampal slice treated as in FIG. 23, but with exposure of the slice to amiloride instead of PcTX venom.
Figure 24B:
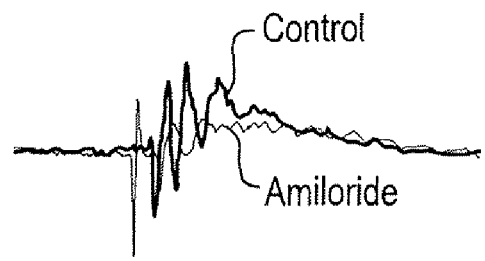

FIG. 24 shows a series of graphs presenting exemplary data for electrical potential measured from a hippocampal slice treated generally as in FIG. 23, but with exposure of the slice to amiloride (100 μM for twenty or thirty minutes prior to electrical stimulation) instead of PcTX venom. Panel 24A of the figure shows three separate graphs of individual voltage traces. Incubation of the hippocampal slice in amiloride for thirty minutes reduced both the number and amplitude of peaks produced in the voltage trace after electrical stimulation of the slice, indicating a similar effect of PcTX venom and amiloride in reducing seizure-like activity in hippocampal explants. Panel 24B of the figure shows a graph with the control trace and the thirty-minute amiloride trace superimposed.

Figure 25:
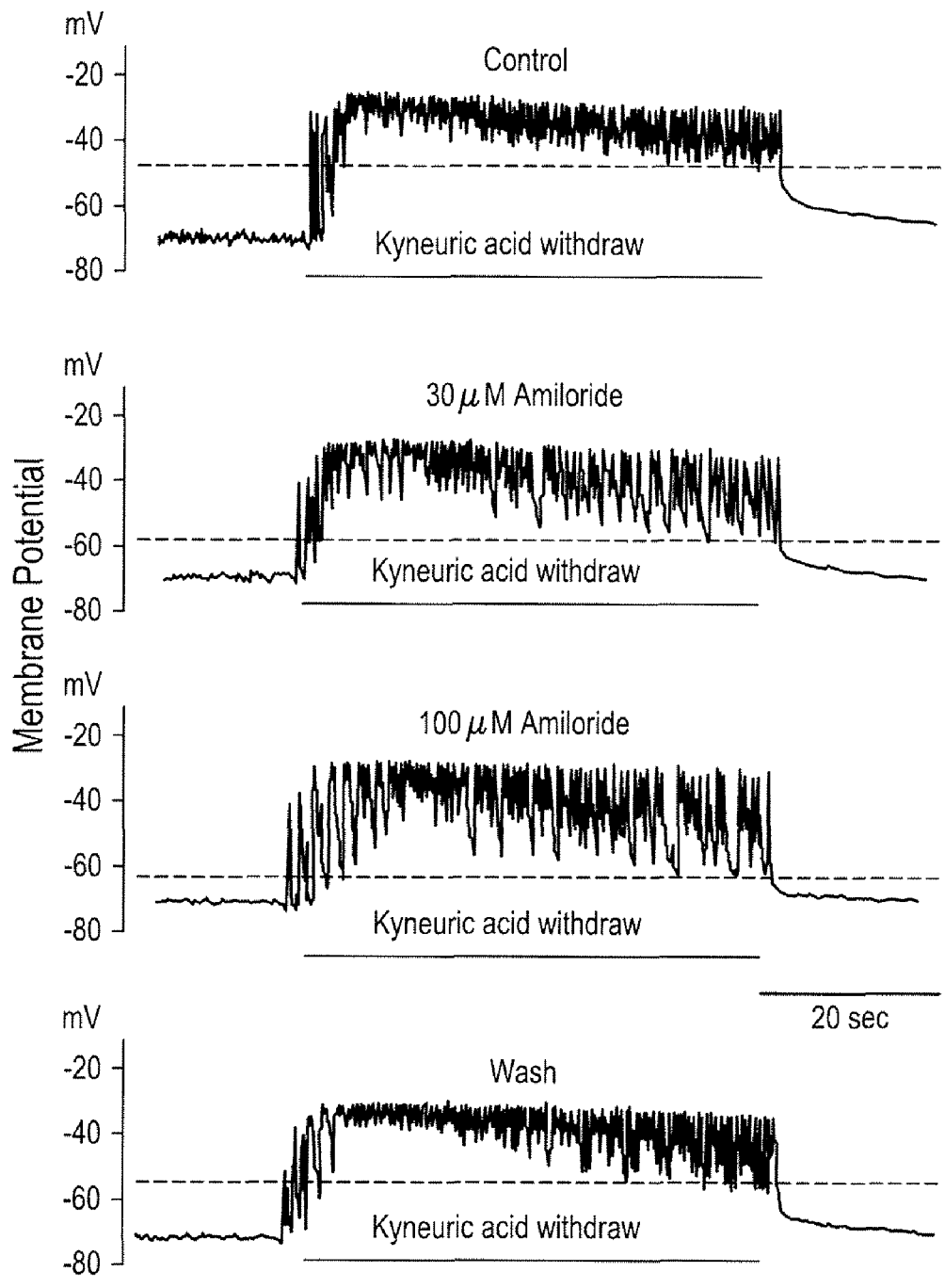
FIG. 25 is a series of graphs presenting exemplary data for the membrane potential of cultured hippocampal neurons measured during transient removal of kyneuric acid from contact with the neurons (to promote seizure-like activity), in the presence or absence of amiloride.

FIG. 25 shows a series of graphs presenting exemplary data for membrane potential of cultured hippocampal neurons measured under seizure-promoting conditions, in the presence or absence of amiloride. The neurons were grown in the presence of kyneuric acid. Removal of the kyneuric acid promoted spontaneous, sustained electrical activity by the neurons.

Figure 26:
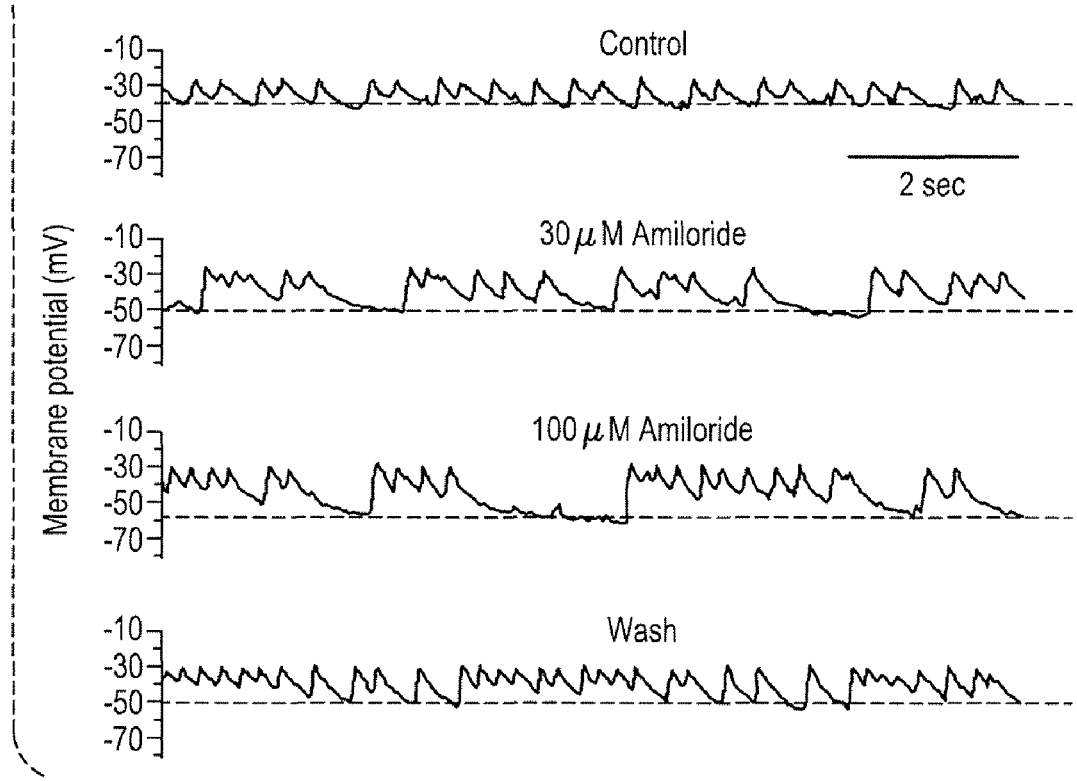
FIG. 26 is a series of graphs that expand pertinent portions of the graphs of FIG. 25 along the time axis, to resolve the electrical activity measured during kyneuric acid removal into individual spikes.

FIG. 26 shows a series of graphs that expand pertinent portions of the graphs of FIG. 25 along the time axis, to resolve the electrical activity measured during kyneuric acid removal into a voltage trace with resolved individual peaks. The magnitude and periodicity of the peaks in the voltage traces changed upon exposure to amiloride. In particular, amiloride reduced the frequency and regularity of the peaks and increased their magnitude. Accordingly, the amiloride blocked the seizure-like electrical activity of the neurons, thereby promoting less synchronized (more normal) electrical activity.

Figure 27:
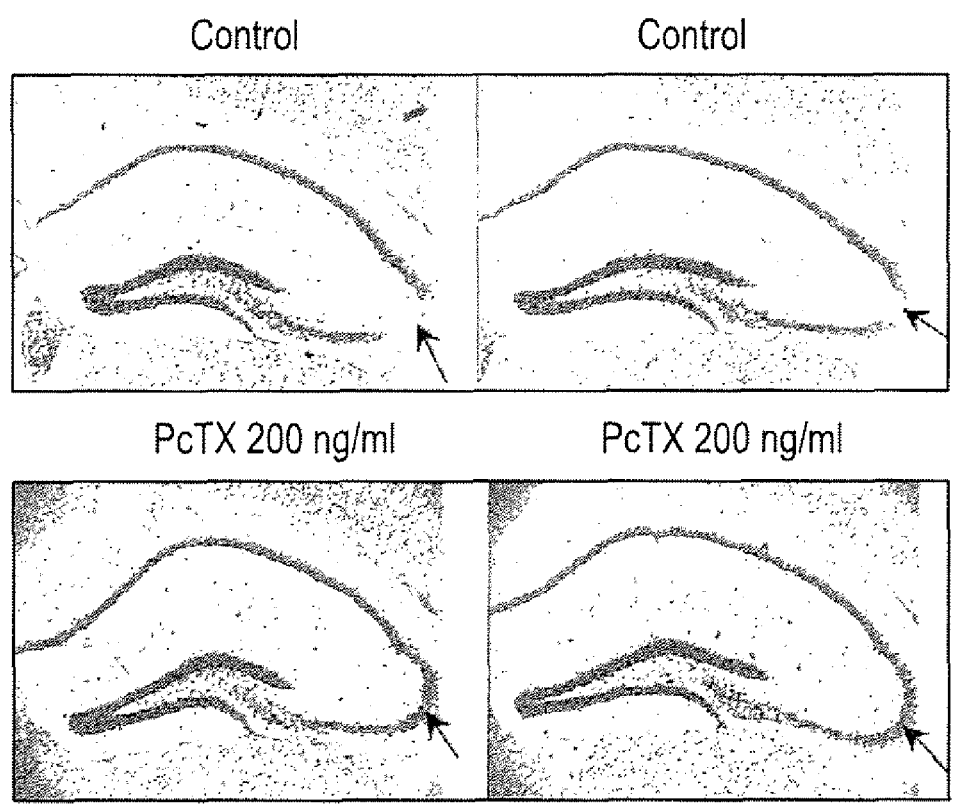
FIG. 27 is a series of photographs of brain sections from mice injected with kainic acid to promote seizure activity in the mice, with or without injection of PcTX venom, with the brain sections stained with cresyl violet to indicate regions of neuron viability, in accordance with aspects of the present teachings.
Figure 28A:
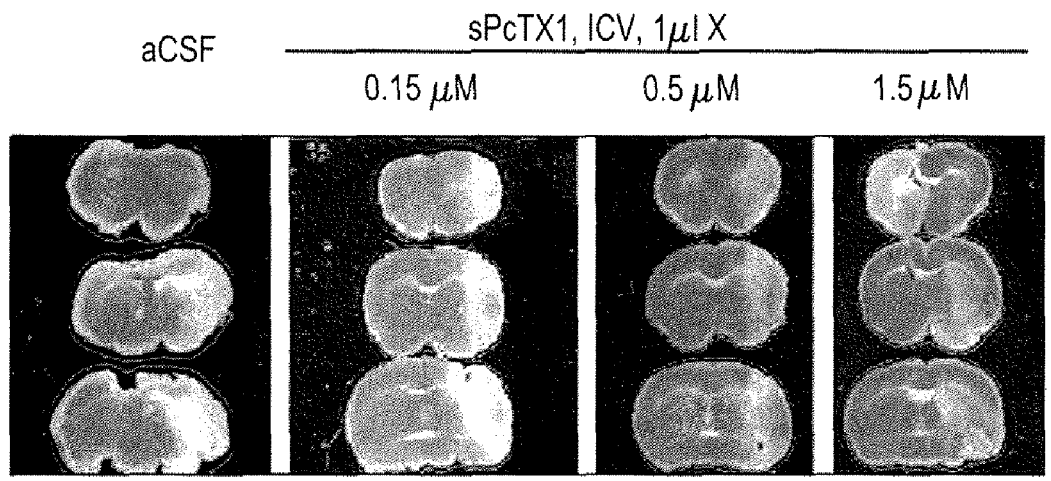
FIG. 28 shows (A) photographs of (B) a graph of dose dependent differences in infarct volume in the cortical tissue of C57B16 mice after 60 minutes of middle cerebral artery occlusion when treated by intracerebroventricular injection with aCSF and varying concentrations of synthetic PcTX1.
Figure 28B:
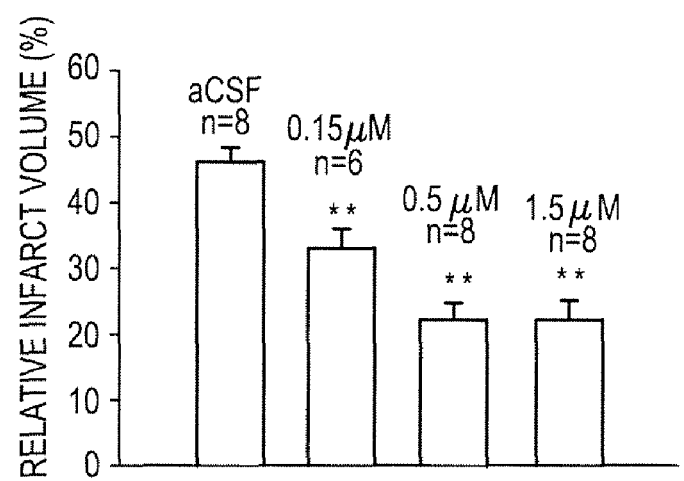
Figure 29A:
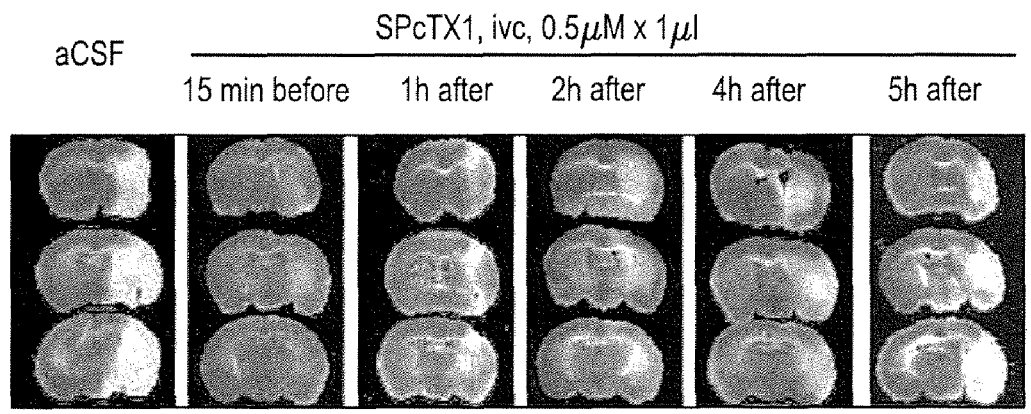
FIG. 29 shows (A) photographs of and (B) a graph of differences in infarct volume in the cortical tissue of C57B16 mice after 60 minutes of middle cerebral artery occlusion treated at different time points prior to and after occlusion by intracerebroventricular injection with aCSF and varying concentrations of synthetic PcTX1.
Figure 29B:
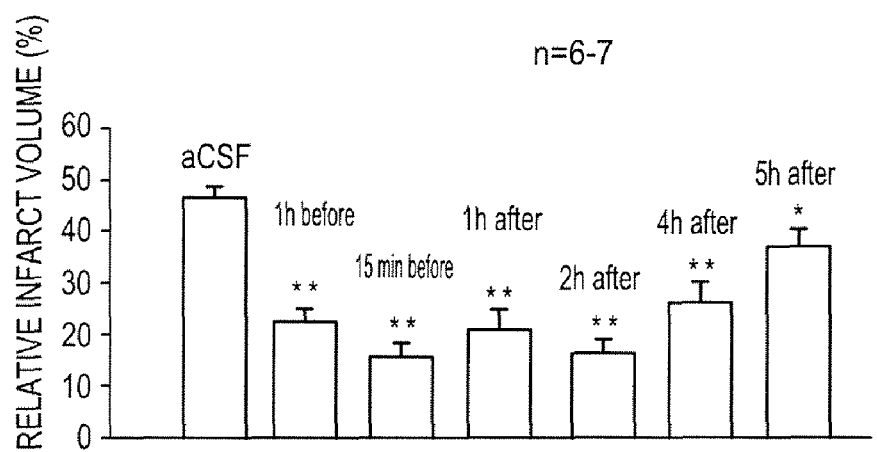
Figure 30A:
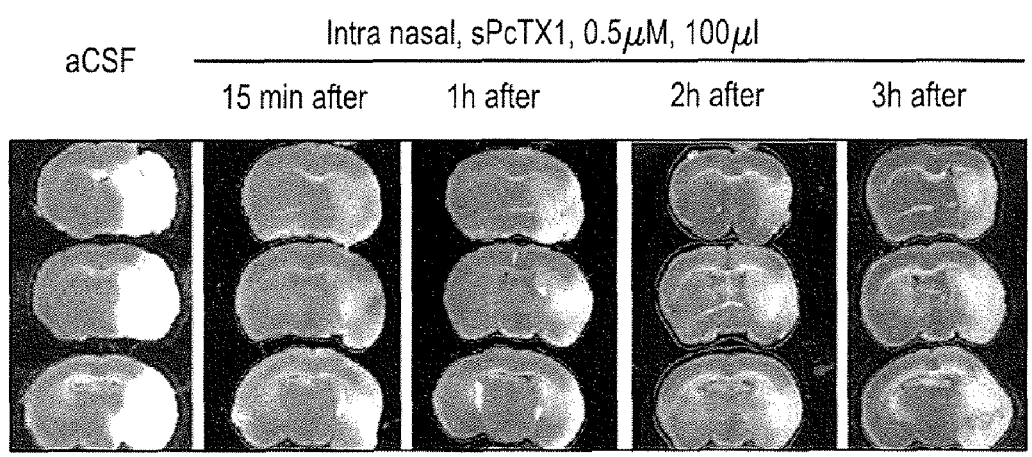
FIG. 30 shows (A) photographs of and (B) a graph of differences in infarct volume in the cortical tissue of C57B16 mice after 60 minutes of middle cerebral artery occlusion treated at different time points prior to and after occlusion with intranasal administration of aCSF and synthetic PcTX1.
Figure 30B:
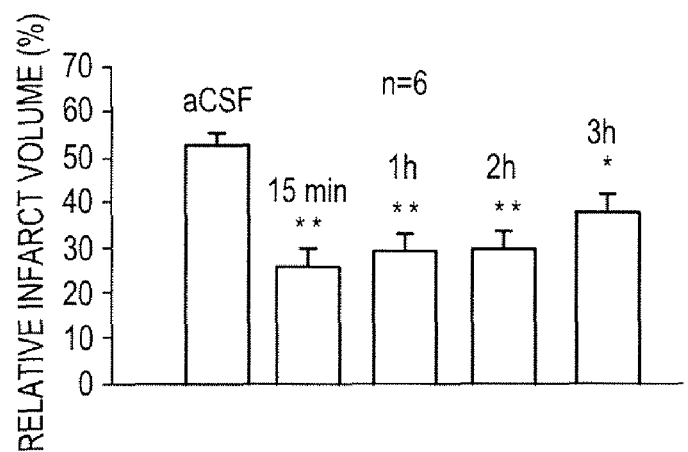

FIG. 27 shows a series of photographs of brain sections from mice injected with kainic acid to promote seizure activity in the mice. Each mouse was injected intra-amygdally with kainic acid (KA), with or without intracerebroventricular injection of PcTX venom one hour prior to kainic acid injection. After injection of kainic acid, control mice suffered seizures, whereas mice that were administered PcTX venom did not suffer seizures. Twenty-four hours after kainic acid injection, the mice were sacrificed and sections of their brains were stained with cresyl violet to mark regions of cell viability (at the time of sacrifice) in blue. An arrow in each photograph points to the expected position of CA3 neurons in the hippocampus. Kainic acid treatment produced substantial death of CA3 neurons, as indicated by loss of staining in the CA3 region of the brains, while administration of PcTX venom protected the CA3 neurons from seizure-induced death. Accordingly, PcTX venom has a neuroprotective effect in an animal model system for epilepsy.

Example XXVIII

Effect of Synthetic PcTX1

Male C57B mice (Charles River) weighing 25-30 g were housed under diurnal lighting conditions (12 h darkness and 12 h light). Experiments were performed according to the international guidelines for animal research. All experiments were performed in accordance with the American animal protection legislation and approved by the Institutional Animal Care and Use Committee of Legacy Research.

Transient focal ischemia was induced by suture occlusion of the middle cerebral artery in male mice anaesthetized using 1.5% isoflurane, 70% $N_2O$ and 28.5% $O_2$ (1). Ischemia was induced by introducing a coated filament (6.0; Doccol) from the external carotid artery into the internal carotid artery and advancing it into the arterial Will's Circle, thereby occluding the middle cerebral artery (32). Rectal and temporalis muscle temperature was maintained at 37° C.±0.5° C. with a thermostatically controlled heating pad and lamp. Cerebral blood flow was monitored by transcranial laser doppler. All surgical procedures were performed under an operating stereomicroscope.

After 60 minutes of occlusion, the mice were reperfused for 24H. Achievement of ischemia was confirmed by monitoring regional cerebral blood flow in the area of the left middle cerebral artery. Mice were treated intracerebroventricularly (icv), intranasally (in) and intravenously (iv) with varying concentrations of synthetic pcTX1 or 1 µl aCSF administered either before or after occlusion. As can be seen in FIGS. 28 A and B, administration of 0.15 μM, 0.5 μM and 1.5 μM of synthetic PcTX1 reduced infarct volume in a dose dependent manner. With icv injection of aCSF (1 μl), 1 h after occlusion produced an average infarct volume of 46.4±2.3% (n=6). Injection with 1 μl of 0.15 μM, 0.5 μM, or 1.5 μM sPcTX1 1 h before occlusion reduced infarct volume to 33.3±3.4%, 22.4±2.7%, and 22.3±3.3%, respectively (n=5-7, p<0.01, FIGS. 28A and B).

The therapeutic time window for administration of synthetic PcTX1 was determined by administering either aCSF or synthetic PcTX1 (0.5 μM, 1 μl) 1 h-before, 15 min-before, 1 h-after, 2 h-after, 4 h-after, or 5 h-after middle cerebral artery occlusion. As shown in FIGS. 29A and B, icv injection of sPcTX1 has more than 5 h protective time window. The relative infarct volume for control (aCSF), 1 h-before, 15 min-before, 1 h-after, 2 h-after, 4 h-after, and 5 h-after was 46.4±2.3%, 22.4±2.7% (p<0.01), 15.7±2.6% (p<0.01), 20.8±3.8% (p<0.01), 16.3±2.4% (p<0.01), 26.3±4.2% (p<0.01), and 37.0±3.4% (p<0.05), respectively.

Absorption of intra nasal application of synthetic PcTX1 (0.5 μM, 100 μl) at different time point following middle cerebral artery occlusion was also examined. Either aCSF or synthetic PcTX1 (0.5 μM, 1 μl) was administered intra nasally 15 minutes 1 h, 2 h or 3 h after the 60 minute middle cerebral artery occlusion. As shown in FIG. 30, intra nasal administration of sPcTX1 has more than 3 h protective time window. With aCSF as a control, the relative infarct volume was 52.7±2.5% (n=6). Intranasal application of synthetic PcTX1 at 15 min, 1 h, 2 h, or 3 h after 1 h middle cerebral artery occlusion significantly reduced the infarct volume to 25.5±41. % (p<0.01), 28.7±3.8% (p<0.01), 29.1±4.2% (p<0.01), and 37.9±3.9% (p<0.05), respectively (FIG. 30).

The effect of intravenous administration of synthetic PcTX1 was also determined. As shown in FIG. 31, intravenous injection of synthetic PcTX1 (0.5 mM, 100 μl) 1 h before middle cerebral artery occlusion reduced the infarct volume from 51.7±3.0% to 33.6±4.6% (n=5 in each group, p<0.01).

Although the foregoing invention has been described in detail by way of example for purposes of clarity of understanding, it will be apparent to the artisan that certain changes and modifications may be practiced within the scope of the appended claims which are presented by way of illustration not limitation. Additionally, as used herein, the singular forms "a", "an", and "the" include plural reference unless the context clearly dictates otherwise.

Various publications and other references have been cited within the foregoing disclosure for economy of description. Each of these references is incorporated herein by reference in its entirety for all purposes. It is noted, however, that the various publications discussed herein are incorporated solely for their disclosure prior to the filing date of the present application, and the inventors reserve the right to antedate such disclosure by virtue of prior invention.

REFERENCES

Aarts, M., Iihara, K., Wei, W. L., Xiong, Z. G., Arundine, M., Cerwinski, W., MacDonald, J. F. and Tymianski, M., 2003. A key role for TRPM7 channels in anoxic neuronal death. *Cell* 115, pp. 863-877.

Akopian, A. N., Chen, C. C., Ding, Y., Cesare, P. and Wood, J. N., 2000. A new member of the acid-sensing ion channel family. *Neuroreport* 11, pp. 2217-2222.

Allen, N. J. and Attwell, D., 2002. Modulation of ASIC channels in rat cerebellar Purkinje neurons by ischemia-related signals. *J. Physiol.* 543, pp. 521-529.

Alvarez de la *Rosa*, D., Zhang, P., Shao, D., White, F. and Canessa, C. M., 2002. Functional implications of the localization and activity of acid-sensitive channels in rat peripheral nervous system. *Proc. Natl. Acad. Sci. USA* 99, pp. 2326-2331.

Alvarez de la Rosa, D., Krueger, S. R., Kolar, A., Shao, D., Fitzsimonds, R. M. and Canessa, C. M., 2003. Distribution, subcellular localization and ontogeny of ASIC1 in the mammalian central nervous system. *J. Physiol.* 546, pp. 77-87.

Bassilana, F., Champigny, G., Waldmann, R., De Weille, J. R., Heurteaux, C. and Lazdunski, M., 1997. The acid-sensitive ionic channel subunit ASIC and the mammalian degenerin MDEG form a heteromultimeric H+-gated Na+ channel with novel properties. *J. Biol Chem.* 272, pp. 28819-28822.

Bederson, J. B., Pitts, L. H., Germano, S. M., Nishimura, M. C., Davis, R. L. and Bartkowski, H. M., 1986. Evaluation of 2,3,5-triphenyltetrazolium chloride as a stain for detection and quantification of experimental cerebral infarction in rats. *Stroke* 17, pp. 1304-1308.

Benos, D. J. and Stanton, B. A., 1999. Functional domains within the degenerin/epithelial sodium channel (Deg/ENaC) superfamily of ion channels. *J. Physiol.* 520, pp. 631-644.

Benson, C. J., Eckert, S. P. and McCleskey, E. W., 1999. Acid-evoked currents in cardiac sensory neurons: a possible mediator of myocardial ischemic sensation. *Circ. Res.* 84, pp. 921-928.

Bevan, S, and Yeats, J., 1991. Protons activate a cation conductance in a sub-population of rat dorsal root ganglion neurones. *J. Physiol.* 433, pp. 145-161.

Bianchi, L. and Driscoll, M., 2002. Protons at the gate: DEG/ENaC ion channels help us feel and remember. *Neuron* 34, pp. 337-340.

Chen, C. C., England, S., Akopian, A. N. and Wood, J. N., 1998. A sensory neuron-specific, proton-gated ion channel. *Proc. Natl. Acad. Sci. USA* 95, pp. 10240-10245.

Chen, C. C., Zimmer, A., Sun, W. H., Hall, J., Brownstein, M. J. and Zimmer, A., 2002. A role for ASIC3 in the modulation of high-intensity pain stimuli. *Proc. Natl. Acad. Sci. USA* 99, pp. 8992-8997.

Choi, D. W., 1988. Calcium-mediated neurotoxicity: relationship to specific channel types and role in ischemic damage. *Trends Neurosci.* II, pp. 465-469 a.

Choi, D. W., 1988. Glutamate neurotoxicity and diseases of the nervous system. *Neuron* 1, pp. 623-634 b.

Choi, D. W., 1995. Calcium: still center-stage in hypoxic-ischemic neuronal death. *Trends Neurosci.* 18, pp. 58-60.

Chu, X. P., Miesch, J., Johnson, M., Root, L., Zhu, X. M., Chen, D., Simon, R. P. and Xiong, Z. G., 2002. Proton-gated channels in PC12 cells. *J. Neurophysiol* 87, pp. 2555-2561.

Dingledine, R., Borges, K., Bowie, D. and Traynelis, S. F., 1999. The glutamate receptor ion channels. *Pharmacol. Rev.* 51, pp. 7-61.

Escoubas, P., De Weille, J. R., Lecoq, A., Diochot, S., Waldmann, R., Champigny, G., Moinier, D., Menez, A. and Lazdunski, M., 2000. Isolation of a tarantula toxin specific for a class of proton-gated Na+ channels. *J. Biol. Chem.* 275, pp. 25116-25121.

Giffard, R. G., Monyer, H., Christine, C. W. and Choi, D. W., 1990. Acidosis reduces NMDA receptor activation, glutamate neurotoxicity, and oxygen-glucose deprivation neuronal injury in cortical cultures. *Brain Res.* 506, pp. 339-342.

Goldberg, M. P. and Choi, D. W., 1993. Combined oxygen and glucose deprivation in cortical cell culture: calcium-dependent and calcium-independent mechanisms of neuronal injury. *J. Neurosci.* 13, pp. 3510-3524.

Grunder, S., Geissler, H. S., Bassler, E. L. and Ruppersberg, J. P., 2000. A new member of acid-sensing ion channels from pituitary gland. *Neuroreport* 11, pp. 1607-1611.

Immke, D. C. and McCleskey, E. W., 2001. Lactate enhances the acid-sensing Na+ channel on ischemia-sensing neurons. *Nat. Neurosci.* 4, pp. 869-870.

Jia, Z., Agopyan, N., Miu, P., Xiong, Z., Henderson, J., Gerlai, R., Taverna, F. A., Velumian, A., MacDonald, J., Carlen, P. et al., 1996. Enhanced LTP in mice deficient in the AMPA receptor GluR2. *Neuron* 17, pp. 945-956.

Johnson, M. B., Jin, K., Minami, M., Chen, D. and Simon, R. P., 2001. Global ischemia induces expression of acid-sensing ion channel 2a in rat brain. *J. Cereb. Blood Flow Metab.* 21, pp. 734-740.

Kaku, D. A., Goldberg, M. P. and Choi, D. W., 1991. Antagonism of non-NMDA receptors augments the neuroprotective effect of NMDA receptor blockade in cortical cultures subjected to prolonged deprivation of oxygen and glucose. *Brain Res.* 554, pp. 344-347.

Kaku, D. A., Giffard, R. G. and Choi, D. W., 1993. Neuroprotective effects of glutamate antagonists and extracellular acidity. *Science* 260, pp. 1516-1518.

Koh, J. Y. and Choi, D. W., 1987. Quantitative determination of glutamate mediated cortical neuronal injury in cell culture by lactate dehydrogenase efflux assay. *J. Neurosci. Methods* 20, pp. 83-90.

Krishtal, O., 2003. The ASICs: signaling molecules?. Modulators? *Trends Neurosci.* 26, pp. 477-483.

Krishtal, O. A. and Pidoplichko, V. I., 1981. A receptor for protons in the membrane of sensory neurons may participate in nociception. *Neuroscience* 6, pp. 2599-2601.

Lee, J. M., Zipfel, G. J. and Choi, D. W., 1999. The changing landscape of ischaemic brain injury mechanisms. *Nature Suppl.* 399, pp. A7-14.

Lingueglia, E., De Weille, J. R., Bassilana, F., Heurteaux, C., Sakai, H., Waldmann, R. and Lazdunski, M., 1997. A modulatory subunit of acid sensing ion channels in brain and dorsal root ganglion cells. *J. Biol. Chem.* 272, pp. 29778-29783.

Litt, L., Gonzalez-Mendez, R., Severinghaus, J. W., Hamilton, W. K., Shuleshko, J., Murphy-Boesch, J. and James, T. L., 1985. Cerebral intracellular changes during supercarbia: an in vivo 31P nuclear magnetic resonance study in rats. *J. Cereb. Blood Flow Metab.* 5, pp. 537-544.

Longa, E. Z., Weinstein, P. R., Carlson, S, and Cummins, R., 1989. Reversible middle cerebral artery occlusion without craniectomy in rats. *Stroke* 20, pp. 8491.

MacGregor, D. G., Avshalumov, M. V. and Rice, M. E., 2003. Brain edema induced by in vitro ischemia: causal factors and neuroprotection. *J. Neurochem.* 85, pp. 1402-1411.

McDonald, J. W., Bhattacharyya, T., Sensi, S. L., Lobner, D., Ying, H. S., Canzoniero, L. M. and Choi, D. W., 1998. Extracellular acidity potentiates AMPA receptor-mediated cortical neuronal death. *J. Neurosci.* 18, pp. 6290-6299.

McLennan, H., 1983. Receptors for the excitatory amino acids in the mammalian central nervous system. *Prog. Neurobiol.* 20, pp. 251-271.

Meldrum, B. S., 1995. Excitatory amino acid receptors and their role in epilepsy and cerebral ischemia. *Ann. NY Acad. Sci.* 757, pp. 492-505.

Miyamoto, O. and Auer, R. N., 2000. Hypoxia, hyperoxia, ischemia, and brain necrosis. *Neurology* 54, pp. 362-371.

Nedergaard, M., Kraig, R. P., Tanabe, J. and Pulsinelli, W. A., 1991. Dynamics of interstitial and intracellular pH in evolving brain infarct. *Am. J. Physiol.* 260, pp. R581-R588.

Pearigen, P., Gwinn, R. and Simon, R. P., 1996. The effects in vivo of hypoxia on brain injury. *Brain Res.* 725, pp. 184-191.

Price, M. P., Snyder, P. M. and Welsh, M. J., 1996. Cloning and expression of a novel human brain Na+ channel. *J. Biol. Chem.* 271, pp. 7879-7882.

Price, M. P., Lewin, G. R., McIlwrath, S. L., Cheng, C., Xie, J., Heppenstall, P. A., Stucky, C. L., Mannsfeldt, A. G., Brennan, T. J., Drummond, H. A. et al., 2000. The mammalian sodium channel BNC1 is required for normal touch sensation. *Nature* 407, pp. 1007-1011.

Price, M. P., McIlwrath, S. L., Xie, J., Cheng, C., Qiao, J., Tarr, D. E., Sluka, K. A., Brennan, T. J., Lewin, G. R. and Welsh, M. J., 2001. The DRASIC cation channel contributes to the detection of cutaneous touch and acid stimuli in mice. *Neuron* 32, pp. 1071-1083.

Relincrona, S., 1985. Brain acidosis. *Ann. Emerg. Med.* 14, pp. 770-776.

Rothman, S. M. and Olney, J. W., 1986. Glutamate and the pathophysiology of hypoxic-ischemic brain damage. *Ann. Neurol* 19, pp. 105-111.

Sattler, R., Xiong, Z., Lu, W. Y., Hafner, M., MacDonald, J. F. and Tymianski, M., 1999. Specific coupling of NMDA receptor activation to nitric oxide neurotoxicity by PSD-95 protein. *Science* 284, pp. 1845-1848.

Siesjo, B. K., Katsura, K. and Kristian, T., 1996. Acidosis-related damage. *Adv. Neurol.* 71, pp. 209-233.

Simon, R. P., Swan, J. H., Griffiths, T. and Meldrum, B. S., 1984. Blockade of N-methyl-D-aspartate receptors may protect against ischemic damage in the brain. *Science* 226, pp. 850-852.

Simon, R. P., Benowitz, N., Hedlund, R. and Copeland, J., 1985. Influence of the blood-brain pH gradient on brain phenobarbital uptake during status epilepticus. *J. Pharmacol Exp. Ther.* 234, pp. 830-835.

Sluka, K. A., Price, M. P., Breese, N. M., Stucky, C. L., Wemmie, J. A. and Welsh, M. J., 2003. Chronic hyperalgesia induced by repeated acid injections in muscle is abolished by the loss of ASIC3, but not ASIC1. *Pain* 106, pp. 229-239.

Stenzel-Poore, M. P., Stevens, S. L., Xiong, Z., Lessov, N. S., Harrington, C. A., Mori, M., Meller, R., Rosenzweig, H. L., Tobar, E., Shaw, T. E. et al., 2003. Effect of ischaemic preconditioning on genomic response to cerebral ischaemia: similarity to neuroprotective strategies in hibernation and hypoxia-tolerant states. *Lancet* 362, pp. 1028-1037.

Swanson, R. A., Farrell, K. and Simon, R. P., 1995. Acidosis causes failure of astrocyte glutamate uptake during hypoxia. *J. Cereb. Blood Flow Metab.* 15, pp. 417-424.

Tang, C. M., Dichter, M. and Morad, M., 1990. Modulation of the N-methyl-D-aspartate channel by extracellular H+. *Proc. Natl. Acad. Sci. USA* 87, pp. 6445-6449.

Tariot, P. N., Farlow, M. R., Grossberg, G. T., Graham, S. M., McDonald, S, and Gergel, I., 2004. Memantine treatment in patients with moderate to severe Alzheimer disease already receiving donepezil: a randomized controlled trial. *JAMA* 291, pp. 317-324.

Tombaugh, G. C. and Sapolsky, R. M., 1993. Evolving concepts about the role of acidosis in ischemic neuropathology. *J. Neurochem.* 61, pp. 793-803.

Traynelis, S. F. and Cull-Candy, S. G., 1990. Proton inhibition of N-methyl-D-aspartate receptors in cerebellar neurons. *Nature* 345, pp. 347-350.

Ugawa, S., Ueda, T., Ishida, Y., Nishigaki, M., Shibata, Y. and Shimada, S., 2002. Amiloride-blockable acid-sensing ion channels are leading acid sensors expressed in human nociceptors. *J. Clin. Invest.* 110, pp. 1185-1190.

Varming, T., 1999. Proton-gated ion channels in cultured mouse cortical neurons. *Neuropharmacology* 38, pp. 1875-1881.

Wahlgren, N. G. and Ahmed, N., 2004. Neuroprotection in cerebral ischaemia: facts and fancies—the need for new approaches. *Cerebroivasc. Dis. Supp.* 17, pp. 153-166.

Waldmann, R. and Lazdunski, M., 1998. H(+)-gated cation channels: neuronal acid sensors in the NaC/DEG family of ion channels. *Curr. Opin. Neurobiol.* 8, pp. 418-424.

Waldmann, R., Champigny, G., Bassilana, F., Heurteaux, C. and Lazdunski, M., 1997a. A proton-gated cation channel involved in acid-sensing. *Nature* 386, pp. 173-177.

Waldmann, R., Bassilana, F., de Weille, J., Champigny, G., Heurteaux, C. and Lazdunski, M., 1997b. Molecular cloning of a non-inactivating proton-gated $Na^+$ channel specific for sensory neurons. *J. Biol. Chem.* 272, pp. 20975-20978.

Waldmann, R., Champigny, G., Lingueglia, E., De Weille, J., Heurteaux, C. and Lazdunski, M., 1999. H(+)-gated cation channels. *Ann. N Y Acad. Sci.* 868, pp. 67-76.

Wemmie, J. A., Chen, J., Askwith, C. C., Hruska-Hageman, A. M., Price, M. P., Nolan, B. C., Yoder, P. G., Lamani, E., Hoshi, T., Freeman, J. H. and Welsh, M. J., 2002. The acid-activated ion channel ASIC contributes to synaptic plasticity, learning, and memory. *Neuron* 34, pp. 463-477.

Wemmie, J. A., Askwith, C. C., Lamani, E., Cassell, M. D., Freeman Jr., J. H. and Welsh, M. J., 2003. Acid-sensing ion channel 1 is localized in brain regions with high synaptic density and contributes to fear conditioning. *J. Neurosci.* 23, pp. 5496-5502.

Westergaard, E., 1969. The cerebral ventricles of the rat during growth. *Acta Anat.* (Basel) 74, pp. 405-423.

Xiong, Z., Lu, W. and MacDonald, J. F., 1997. Extracellular calcium sensed by a novel cation channel in hippocampal neurons. *Proc. Natl. Acad. Sci. USA* 94, pp. 7012-7017.

Yermolaieva, O., Leonard, A. S., Schnizler, M. K., Abboud, F. M. and Welsh, M. J., 2004. Extracellular acidosis increases neuronal cell calcium by activating acid-sensing ion channel 1a. *Proc. Natl. Acad. Sci. USA* 101, pp. 6752-6757.

Ying, W., Han, S. K., Miller, J. W. and Swanson, R. A., 1999. Acidosis potentiates oxidative neuronal death by multiple mechanisms. *J. Neurochem.* 73, pp. 1549-1556.

Xiong, Z. G., Zhu, X. M., Chu, X. P., Minami, M., Hey, J., Wei, W. L., MacDonald, J. F., Wemmie, J. A., Price, M. P., Welsh, M. J., et al. 2004. Neuroprotection in ischemia: blocking calcium-permeable acid-sensing ion channels. *Cell* 118:687-698.

Benveniste, M., and Dingledine, R. 2005. Limiting stroke-induced damage by targeting an acid channel. *N Engl J Med* 352:85-86.

Gao, J., Duan, B., Wang, D. G., Deng, X. H., Zhang, G. Y., Xu, L., and Xu, T. L. 2005. Coupling between NMDA Receptor and Acid-Sensing Ion Channel Contributes to Ischemic Neuronal Death. *Neuron* 48:635-646.

Krishtal, O. 2003. The ASICs: signaling molecules? Modulators? *Trends Neurosci* 26:477-483.

Duggan, A., Garcia-Anoveros, J., and Corey, D. P. 2002. The PDZ domain protein PICK1 and the sodium channel BNaCl interact and localize at mechanosensory terminals of dorsal root ganglion neurons and dendrites of central neurons. *J Biol Chem* 277:5203-5208.

Lingueglia, E., de Weille, J. R., Bassilana, F., Heurteaux, C., Sakai, H., Waldmann, R., and Lazdunski, M. 1997. A modulatory subunit of acid sensing ion channels in brain and dorsal root ganglion cells. *J Biol Chem* 272:29778-29783.

Waldmann, R., Champigny, G., Bassilana, F., Heurteaux, C., and Lazdunski, M. 1997. A proton-gated cation channel involved in acid-sensing. *Nature* 386:173-177.

Waldmann, R., Champigny, G., Voilley, N., Lauritzen, I., and Lazdunski, M. 1996. The mammalian degenerin MDEG, an amiloride-sensitive cation channel activated by mutations causing neurodegeneration in *Caenorhabditis elegans*. *J Biol Chem* 271:10433-10436.

Wu, L. J., Duan, B., Mei, Y. D., Gao, J., Chen, J. G., Zhuo, M., Xu, L., Wu, M., and Xu, T. L. 2004. Characterization of acid-sensing ion channels in dorsal horn neurons of rat spinal cord. *J Biol Chem* 279:43716-43724.

Yermolaieva, O., Leonard, A. S., Schnizler, M. K., Abboud, F. M., and Welsh, M. J. 2004. Extracellular acidosis increases neuronal cell calcium by activating acid-sensing ion channel 1a. *Proc Natl Acad Sci USA* 101:6752-6757.

Wemmie, J. A., Askwith, C. C., Lamani, E., Cassell, M. D., Freeman, J. H., Jr., and Welsh, M. J. 2003. Acid-sensing ion channel 1 is localized in brain regions with high synaptic density and contributes to fear conditioning. *J Neurosci* 23:5496-5502.

Wemmie, J. A., Chen, J., Askwith, C. C., Hruska-Hageman, A. M., Price, M. P., Nolan, B. C., Yoder, P. G., Lamani, E., Hoshi, T., Freeman, J. H., Jr., et al. 2002. The acid-activated ion channel ASIC contributes to synaptic plasticity, learning, and memory. *Neuron* 34:463-477.

Wemmie, J. A., Coryell, M. W., Askwith, C. C., Lamani, E., Leonard, A. S., Sigmund, C. D., and Welsh, M. J. 2004. Overexpression of acid-sensing ion channel 1a in transgenic mice increases acquired fear-related behavior. *Proc Natl Acad Sci U S A* 101:3621-3626.

Allen, N. J., and Attwell, D. 2002. Modulation of ASIC channels in rat cerebellar Purkinje neurons by ischaemia-related signals. *J Physiol* 543:521-529.

Diarra, A., Sheldon, C., Brett, C. L., Baimbridge, K. G., and Church, J. 1999. Anoxia-evoked intracellular pH and Ca2+ concentration changes in cultured postnatal rat hippocampal neurons. *Neuroscience* 93:1003-1016.

Obrenovitch, T. P., Scheller, D., Matsumoto, T., Tegtmeier, F., Holler, M., and Symon, L. 1990. A rapid redistribution of hydrogen ions is associated with depolarization and repolarization subsequent to cerebral ischemia reperfusion. *J Neurophysiol* 64:1125-1133.

Deitmer, J. W., and Rose, C. R. 1996. pH regulation and proton signalling by glial cells. *Prog Neurobiol* 48:73-103.

Li, P. A., and Siesjo, B. K. 1997. Role of hyperglycaemia-related acidosis in ischaemic brain damage. *Acta Physiol Scand* 161:567-580.

Wahligren, N. G., and Ahmed, N. 2004. Neuroprotection in cerebral ischaemia: facts and fancies—the need for new approaches. *Cerebrovase Dis* 17 Suppl 1: 153-166.

Culmsee, C., Junker, V., Kremers, W., Thal, S., Plesnila, N., and Krieglstein, J. 2004. Combination therapy in ischemic stroke: synergistic neuroprotective effects of memantine and clenbuterol. *Stroke* 35:1197-1202.

Group, T.N.I.o.N.D.a.S.r.-P.S.S. 1995. Tissue plasminogen activator for acute ischemic stroke. *N Engl J Med* 333:1581-1587.

Astrup, J., Symon, L., Branston, N. M., and Lassen, N. A. 1977. Cortical evoked potential and extracellular K+ and H+ at critical levels of brain ischemia. *Stroke* 8:51-57.

Siesjo, B. K. 1992. Pathophysiology and treatment of focal cerebral ischemia. Part II: Mechanisms of damage and treatment. *J Neurosurg* 77:337-354.

Back, T., Hoehn, M., Mies, G., Busch, E., Schmitz, B., Kohno, K., and Hossmann, K. A. 2000. Penumbral tissue alkalosis in focal cerebral ischemia: relationship to energy metabolism, blood flow, and steady potential. *Ann Neurol* 47:485-492.

Waldmann, R. 2001. Proton-gated cation channels—neuronal acid sensors in the central and peripheral nervous system. *Adv Exp Med Biol* 502:293-304.

Illum, L. 2000. Transport of drugs from the nasal cavity to the central nervous system. *Eur J Pharm Sci* 11:1-18.

Thorne, R. G., and Frey, W. H., 2nd. 2001. Delivery of neurotrophic factors to the central nervous system: pharmacokinetic considerations. *Clin Pharmacokinet* 40:907-946.

Liu, X. F., Fawcett, J. R., Thorne, R. G., DeFor, T. A., and Frey, W. H., 2nd. 2001. Intranasal administration of insulin-like growth factor-I bypasses the blood-brain barrier and protects against focal cerebral ischemic damage. *J Neurol Sci* 187:91-97.

Liu, X. F., Fawcett, J. R., Thorne, R. G., and Frey, W. H., 2nd. 2001. Non-invasive intranasal insulin-like growth factor-I reduces infarct volume and improves neurologic function in rats following middle cerebral artery occlusion. *Neurosci Lett* 308:91-94.

Capsoni, S., Giannotta, S., and Cattaneo, A. 2002. Nerve growth factor and galantamine ameliorate early signs of neurodegeneration in anti-nerve growth factor mice. *Proc Natl Acad Sci USA* 99:12432-12437.

Dirnagl, U., Iadecola, C., and Moskowitz, M. A. 1999. Pathobiology of ischaemic stroke: an integrated view. *Trends Neurosci* 22:391-397.

Longa, E. Z., Weinstein, P. R., Carlson, S., and Cummins, R. 1989. Reversible middle cerebral artery occlusion without craniectomy in rats. *Stroke* 20:84-91.

Bederson, J. B., Pitts, L. H., Germano, S. M., Nishimura, M. C., Davis, R. L., and Bartkowski, H. M. 1986. Evaluation of 2,3,5-triphenyltetrazolium chloride as a stain for detection and quantification of experimental cerebral infarction in rats. *Stroke* 17:1304-1308.

Pignataro, G., Gala, R., Cuomo, O., Tortiglione, A., Giaccio, L., Castaldo, P., Sirabella, R., Matrone, C., Canitano, A., Amoroso, S., et al. 2004. Two sodium/calcium exchanger gene products, NCX1 and NCX3, play a major role in the development of permanent focal cerebral ischemia. *Stroke* 35:2566-2570.

Pignataro G, Simon R P, Xiong Z G (2007) Prolonged activation of ASIC1a and the time window for neuroprotection in cerebral ischaemia. Brain 130: 151-158

We claim:

1. A method of treating ischemic brain injury or seizures in a mammalian subject comprising administering a neuroprotective effective amount of an acid sensing ion channel peptide inhibitor comprising a cystine knot motif selected from the group consisting of SEQ ID NO: 1, SEQ ID NO: 2, SEQ ID NO:3, SEQ ID NO: 4, and SEQ ID NO: 5.

2. The method of claim 1, wherein the inhibitor is PcTx1 identified as SEQ ID NO: 1.

3. The method of claim 1, wherein the inhibitor consists of the peptide of SEQ ID NO: 2.

4. The method of claim 1, wherein the inhibitor consists of the peptide of SEQ ID NO: 3.

5. The method of claim 1, wherein the inhibitor consists of the peptide of SEQ ID NO: 4.

6. The method of claim 1, wherein the inhibitor consists of the peptide of SEQ ID NO: 5.

7. The method of claim 2, wherein the PcTx1 of SEQ ID NO: 1 is synthetic.

8. The method of claim 1, wherein the method comprises treatment of ischemic brain injury.

9. The method of claim 1, wherein the method comprises treatment of seizure.

10. The method of claim 9, wherein the seizure is caused by epilepsy.

11. The method of claim 1 further comprising a secondary therapeutic agent.

12. The method of claim 11, wherein the secondary neuroprotective therapeutic or adjunctive therapeutic agent is administered to said subject in a coordinate administration protocol, simultaneously with, prior to, or after, administration of said inhibitor of an acid sensing ion channel.

13. The method of claim 11, wherein the secondary neuroprotective therapeutic or adjunctive therapeutic agent is administered to said subject by a different method than the administration of the inhibitor or an acid sensing ion channel.

14. The method of claim 1, wherein the inhibitor is administered intranasally.

15. The method of claim 11, wherein the secondary neuroprotective therapeutic agent or other adjunctive therapeutic agent is an antagonist selective for a glutamate receptor, an alkalinizing agent, an anticoagulant, tissue plasminogen activator, aspirin, or an anti-platelet agent.

16. The method of claim 15, wherein the antagonist selective for a glutamate receptor is memantine.

17. The method of claim 15, wherein the alkalizing agent is sodium bicarbonate.

18. The method of claim 11, wherein the inhibitor of an acid sensing ion channel and a secondary neuroprotective therapeutic agent are administered less than five hours after the occurrence of an event that causes brain injury.

19. The method of claim 11, wherein the inhibitor of an acid sensing ion channel and a secondary neuroprotective therapeutic agent are administered less than three hours after the occurrence of an event that causes brain injury.

20. The method of claim 1, wherein the inhibitor is administered intracerebroventricularly.

21. The method of claim 8, wherein the ischemic brain injury is caused by a stroke.

22. A method of treating stroke in a mammalian subject comprising administering a neuroprotective effective amount of PcTx1 identified as SEQ ID NO: 1.

* * * * *